US007129342B1

(12) United States Patent
Bukh et al.

(10) Patent No.: US 7,129,342 B1
(45) Date of Patent: Oct. 31, 2006

(54) INFECTIOUS CDNA CLONE OF GB VIRUS B AND USES THEREOF

(75) Inventors: **

GB Virus-B (pGBB)

Hepatitis C Virus (pCV-H77C)

|  | 10 | 20 | 30 | 40 | 50 |  |
|---|---|---|---|---|---|---|
|  | 1234567890 | 1234567890 | 1234567890 | 1234567890 | 1234567890 |  |
|  | GCCAGCCCCC | TGATGGGGGC | GACACTCCAC | CATGAATCAC | TCCCCTGTGA | 50 |
|  | GGAACTACTG | TCTTCACGCA | GAAAGCGTCT | AGCCATGGCG | TTAGTATGAG | 100 |
|  | TGTCGTGCAG | CCTCCAGGAC | CCCCCCTCCC | GGAGAGCCA | TAGTGGTCTG | 150 |
|  | CGGAACCGGT | GAGTACACCG | GAATTGCCAG | GACGACCGGG | TCCTTTCTTG | 200 |
|  | GATAAACCCG | CTCAATGCCT | GGAGATTTGG | GCGTGCCCCC | GCAAGACTGC | 250 |
|  | TAGCCGAGTA | GTGTTGGGTC | GCGAAAGGCC | TTGTGGTACT | GCCTGATAGG | 300 |
|  | GTGCTTGCGA | GTGCCCCGGG | AGGTCTCGTA | GACCGTGCAC | CATGAGCACG | 350 |
|  | AATCCTAAAC | CTCAAAGAAA | AACCAAACGT | AACACCAACC | GTCGCCCACA | 400 |
|  | GGACGTCAAG | TTCCCGGGTG | GCGGTCAGAT | CGTTGGTGGA | GTTACTTGT | 450 |
|  | TGCCGCGCAG | GGCCCTAGA | TTGGGTGTGC | GCGCGACGAG | GAAGACTTCC | 500 |
|  | GAGCGGTCGC | AACCTCGAGG | TAGACGTCAG | CCTATCCCCA | AGGCACGTCG | 550 |
|  | GCCCGAGGGC | AGGACCTGGG | CTCAGCCCGG | GTACCCTTGG | CCCCTCTATG | 600 |
|  | GCAATGAGGG | TTGCGGGTGG | GCGGGATGGC | TCCTGTCTCC | CCGTGGCTCT | 650 |
|  | CGGCCTAGCT | GGGGCCCCAC | AGACCCCCGG | CGTAGGTCGC | GCAATTTGGG | 700 |
|  | TAAGGTCATC | GATACCCTTA | CGTGCGGCTT | CGCCGACCTC | ATGGGGTACA | 750 |
|  | TACCGCTCGT | CGGCGCCCCT | CTTGGAGGCG | CTGCCAGGGC | CCTGGCGCAT | 800 |
|  | GGCGTCCGGG | TTCTGGAAGA | CGGCGTGAAC | TATGCAACAG | GGAACCTTCC | 850 |
|  | TGGTTGCTCT | TTCTCTATCT | TCCTTCTGGC | CCTGCTCTCT | TGCCTGACTG | 900 |
|  | TGCCCGCTTC | AGCCTACCAA | GTGCGCAATT | CCTCGGGCT | TTACCATGTC | 950 |
|  | ACCAATGATT | GCCCTAACTC | GAGTATTGTG | TACGAGGCGG | CCGATGCCAT | 1000 |
|  | CCTGCACACT | CCGGGGTGTG | TCCCTTGCGT | TGCGAGGGT | AACGCCTCGA | 1050 |
|  | GGTGTTGGGT | GGCGGTGACC | CCCACGGTGG | CCACCAGGGA | CGGCAAACTC | 1100 |
|  | CCCACAACGC | AGCTTCGACG | TCATATCGAT | CTGCTTGTCG | GGAGCGCCAC | 1150 |
|  | CCTCTGCTCG | GCCCTCTACG | TGGGGACCT | GTGCGGGTCT | GTCTTTCTTG | 1200 |
|  | TTGGTCAACT | GTTTACCTTC | TCTCCCAGGC | GCCACTGGAC | GACGCAAGAC | 1250 |
|  | TGCAATTGTT | CTATCTATCC | CGGCCATATA | ACGGGTCATC | GCATGGCATG | 1300 |
|  | GGATATGATG | ATGAACTGGT | CCCCTACGGC | AGCGTTGGTG | GTAGCTCAGC | 1350 |
|  | TGCTCCGGAT | CCCACAAGCC | ATCATGGACA | TGATCGCTGG | TGCTCACTGG | 1400 |
|  | GGAGTCCTGG | CGGGCATAGC | GTATTTCTCC | ATGGTGGGA | ACTGGGCGAA | 1450 |
|  | GGTCCTGGTA | GTGCTGCTGC | TATTTGCCGG | CGTCGACGCG | GAAACCCACG | 1500 |
|  | TCACCGGGG | AAATGCCGGC | CGCACCACGG | CTGGGCTTGT | TGGTCTCCTT | 1550 |
|  | ACACCAGGCG | CCAAGCAGAA | CATCCAACTG | ATCAACACCA | ACGGCAGTTG | 1600 |
|  | GCACATCAAT | AGCACGGCCT | TGAATTGCAA | TGAAAGCCTT | AACACCGGCT | 1650 |
|  | GGTTAGCAGG | GCTCTTCTAT | CAACACAAAT | TCAACTCTTC | AGGCTGTCCT | 1700 |
|  | GAGAGGTTGG | CCAGCTGCCG | ACGCCTTACC | GATTTTGCCC | AGGGCTGGGG | 1750 |
|  | TCCTATCAGT | TATGCCAACG | GAAGCGGCCT | CGACGAACGC | CCCTACTGCT | 1800 |
|  | GGCACTACCC | TCAAGACCT | TGTGGCATTG | TGCCCGCAAA | GAGCGTGTGT | 1850 |
|  | GGCCCGGTAT | ATTGCTTCAC | TCCCAGCCCC | GTGGTGGTGG | GAACGACCGA | 1900 |

FIG. 6A

|  | 10 | 20 | 30 | 40 | 50 |  |
|---|---|---|---|---|---|---|
|  | 1234567890 | 1234567890 | 1234567890 | 1234567890 | 1234567890 |  |
|  | CAGGTCGGGC | GCGCCTACCT | ACAGCTGGGG | TGCAAATGAT | ACGGATGTCT | 1950 |
|  | TCGTCCTTAA | CAACACCAGG | CCACCGCTGG | GCAATTGGTT | CGGTTGTACC | 2000 |
|  | TGGATGAACT | CAACTGGATT | CACCAAAGTG | TGCGGAGCGC | CCCCTTGTGT | 2050 |
|  | CATCGGAGGG | GTGGCAACA | ACACCTTGCT | CTGCCCCACT | GATTGCTTCC | 2100 |
|  | GCAAACATCC | GGAAGCCACA | TACTCTCGGT | GCGGCTCCGG | TCCCTGGATT | 2150 |
|  | ACACCCAGGT | GCATGGTCGA | CTACCCGTAT | AGGCTTTGGC | ACTATCCTTG | 2200 |
|  | TACCATCAAT | TACACCATAT | TCAAAGTCAG | GATGTACGTG | GGAGGGGTCG | 2250 |
|  | AGCACAGGCT | GGAAGCGGCC | TGCAACTGGA | CGCGGGGCGA | ACGCTGTGAT | 2300 |
|  | CTGGAAGACA | GGACAGGTC | CGAGCTCAGC | CCGTTGCTGC | TGTCCACCAC | 2350 |
|  | ACAGTGGCAG | GTCCTTCCGT | GTTCTTTCAC | GACCCTGCCA | GCCTTGTCCA | 2400 |
|  | CCGGCCTCAT | CCACCTCCAC | CAGAACATTG | TGGACGTGCA | GTACTTGTAC | 2450 |
|  | GGGGTAGGGT | CAAGCATCGC | GTCCTGGCC | ATTAAGTGGG | AGTACGTCGT | 2500 |
|  | TCTCCTGTTC | CTTCTGCTTG | CAGACGCGCG | CGTCTGCTCC | TGCTTGTGGA | 2550 |
|  | TGATGTTACT | CATATCCCAA | GCGGAGGCGG | CTTTGGAGAA | CCTCGTAATA | 2600 |
|  | CTCAATGCAG | CATCCCTGGC | CGGGACGCAC | GGTCTTGTGT | CCTTCCTCGT | 2650 |
|  | GTTCTTCTGC | TTTGCGTGGT | ATCTGAAGGG | TAGGTGGGTG | CCCGGAGCGG | 2700 |
|  | TCTACGCCCT | CTACGGGATG | TGCCCTCTCC | TCCTGCTCCT | GCTGGCGTTG | 2750 |
|  | CCTCAGCGGG | CATACGCACT | GGACACGGAG | GTGGCCGCGT | CGTGTGGCGG | 2800 |
|  | CGTTGTTCTT | GTCGGGTTAA | TGGCGCTGAC | TCTGTCGCCA | TATTACAAGC | 2850 |
|  | GCTATATCAG | CTGGTGCATG | TGGTGGCTTC | AGTATTTCT | GACCAGAGTA | 2900 |
|  | GAAGCGCAAC | TGCACGTGTG | GGTTCCCCCC | CTCAACGTCC | GGGGGGGCG | 2950 |
|  | CGATGCCGTC | ATCTTACTCA | TGTGTGTAGT | ACACCCGACC | CTGGTATTTG | 3000 |
|  | ACATCACCAA | ACTACTCCTG | GCCATCTTCG | GACCCTTTG | GATTCTTCAA | 3050 |
|  | GCCAGTTTGC | TTAAAGTCCC | CTACTTCGTG | CGCGTTCAAG | GCCTTCTCCG | 3100 |
|  | GATCTGCGCG | CTAGCGCGGA | AGATAGCCGG | AGGTCATTAC | GTGCAAATGG | 3150 |
|  | CCATCATCAA | GTTAGGGCG | CTTACTGGCA | CCTATGTGTA | TAACCATCTC | 3200 |
|  | ACCCCTCTTC | GAGACTGGGC | GCACAACGGC | CTGCCAGATC | TGCCGTGGC | 3250 |
|  | TGTGGAACCA | GTCGTCTTCT | CCCGAATGGA | GACCAAGCTC | ATCACGTGGG | 3300 |
|  | GGCAGATAC | CGCCGCGTGC | GGTGACATCA | TCAACGGCTT | GCCCGTCTCT | 3350 |
|  | GCCCGTAGGG | GCCAGGAGAT | ACTGCTTGGG | CCAGCCGACG | GAATGGTCTC | 3400 |
|  | CAAGGGGTGG | AGGTTGCTGG | CGCCCATCAC | GGCGTACGCC | CAGCAGACGA | 3450 |
|  | GAGGCCTCCT | AGGGTGTATA | ATCACCAGCC | TGACTGGCCG | GGACAAAAAC | 3500 |
|  | CAAGTGGAGG | GTGAGGTCCA | GATCGTGTCA | ACTGCTACCC | AAACCTTCCT | 3550 |
|  | GGCAACGTGC | ATCAATGGGG | TATGCTGGAC | TCTGTACCAC | GGGCCGGAA | 3600 |
|  | CGAGGACCAT | CGCATCACCC | AAGGGTCCTG | TCATCCAGAT | GTATACCAAT | 3650 |
|  | GTGGACCAAG | ACCTTGTGGG | CTGCCCCGCT | CCTCAAGGTT | CCCGCTCATT | 3700 |
|  | GACACCCTGT | ACCTGCGGCT | CCTCGGACCT | TTACCTGGTC | ACGAGGCACG | 3750 |
|  | CCGATGTCAT | TCCCGTGCGC | CGGCGAGGTG | ATAGCAGGGG | TAGCCTGCTT | 3800 |

FIG. 6B

|  | 10 | 20 | 30 | 40 | 50 | |
|---|---|---|---|---|---|---|
|  | 1234567890 | 1234567890 | 1234567890 | 1234567890 | 1234567890 | |
|  | TCGCCCCGGC | CCATTTCCTA | CTTGAAAGGC | TCCTCGGGGG | GTCCGCTGTT | 3850 |
|  | GTGCCCCGCG | GGACACGCCG | TGGCCCTATT | CAGGGCCGCG | GTGTGCACCC | 3900 |
|  | GTGGAGTGGC | TAAAGCGGTG | GACTTTATCC | CTGTGGAGAA | CCTAGGGACA | 3950 |
|  | ACCATGAGAT | CCCCGGTGTT | CACGGACAAC | TCCTCTCCAC | CAGCAGTGCC | 4000 |
|  | CCAGAGCTTC | CAGGTGGCCC | ACCTGCATGC | TCCCACCGGC | AGCGGTAAGA | 4050 |
|  | GCACCAAGGT | CCCGGCTGCG | TACGCAGCCC | AGGGCTACAA | GGTGTTGGTG | 4100 |
|  | CTCAACCCCT | CTGTTGCTGC | AACGCTGGGC | TTTGGTGCTT | ACATGTCCAA | 4150 |
|  | GGCCCATGGG | GTTGATCCTA | ATATCAGGAC | CGGGGTGAGA | ACAATTACCA | 4200 |
|  | CTGGCAGCCC | CATCACGTAC | TCCACCTACG | GCAAGTTCCT | TGCCGACGGC | 4250 |
|  | GGGTGCTCAG | GAGGTGCTTA | TGACATAATA | ATTGTGACG | AGTGCCACTC | 4300 |
|  | CACGGATGCC | ACATCCATCT | TGGGCATCGG | CACTGTCCTT | GACCAAGCAG | 4350 |
|  | AGACTGCGGG | GGCGAGACTG | GTTGTGCTCG | CCACTGCTAC | CCCTCCGGC | 4400 |
|  | TCCGTCACTG | TGTCCCATCC | TAACATCGAG | GAGGTTGCTC | TGTCCACCAC | 4450 |
|  | CGGAGAGATC | CCCTTTTACG | GCAAGGCTAT | CCCCCTCGAG | GTGATCAAGG | 4500 |
|  | GGGAAGACA | TCTCATCTTC | TGCCACTCAA | AGAAGAAGTG | CGACGAGCTC | 4550 |
|  | GCCGCGAAGC | TGGTCGCATT | GGGCATCAAT | GCCGTGGCCT | ACTACCGCGG | 4600 |
|  | TCTTGACGTG | TCTGTCATCC | CGACCAGCGG | CGATGTTGTC | GTCGTGTCGA | 4650 |
|  | CCGATGCTCT | CATGACTGGC | TTTACCGGCG | ACTTCGACTC | TGTGATAGAC | 4700 |
|  | TGCAACACGT | GTGTCACTCA | GACAGTCGAT | TTCAGCCTTG | ACCCTACCTT | 4750 |
|  | TACCATTGAG | ACAACCACGC | TCCCCCAGGA | TGCTGTCTCC | AGGACTCAAC | 4800 |
|  | GCCGGGCAG | GACTGGCAGG | GGGAAGCCAG | GCATCTATAG | ATTTGTGGCA | 4850 |
|  | CCGGGGGAGC | GCCCCTCCGG | CATGTTCGAC | TCGTCCGTCC | TCTGTGAGTG | 4900 |
|  | CTATGACGCG | GGCTGTGCTT | GGTATGAGCT | CACGCCCGCC | GAGACTACAG | 4950 |
|  | TTAGGCTACG | AGCGTACATG | AACACCCCGG | GGCTTCCCGT | GTGCCAGGAC | 5000 |
|  | CATCTTGAAT | TTTGGGAGGG | CGTCTTTACG | GGCCTCACTC | ATATAGATGC | 5050 |
|  | CCACTTTTTA | TCCAGACAA | AGCAGAGTGG | GGAGAACTTT | CCTTACCTGG | 5100 |
|  | TAGCGTACCA | AGCCACCGTG | TGCGCTAGGG | CTCAAGCCCC | TCCCCATCG | 5150 |
|  | TGGACCAGA | TGTGGAAGTG | TTTGATCCGC | CTTAAACCCA | CCCTCCATGG | 5200 |
|  | GCCAACACCC | CTGCTATACA | GACTGGGCGC | TGTTCAGAAT | GAAGTCACCC | 5250 |
|  | TGACGCACCC | AATCACCAAA | TACATCATGA | CATGCATGTC | GGCCGACCTG | 5300 |
|  | GAGGTCGTCA | CGAGCACCTG | GGTGCTCGTT | GGCGGCGTCC | TGCTGCTCT | 5350 |
|  | GGCCGCGTAT | TGCCTGTCAA | CAGGCTGCGT | GGTCATAGTG | GGCAGGATCG | 5400 |
|  | TCTTGTCCGG | GAAGCCGGCA | ATTATACCTG | ACAGGGAGGT | TCTCTACCAG | 5450 |
|  | GAGTTCGATG | AGATGGAAGA | GTGCTCTCAG | CACTTACCGT | ACATCGAGCA | 5500 |
|  | AGGATGATG | CTCGCTGAGC | AGTTCAAGCA | GAAGGCCCTC | GGCCTCCTGC | 5550 |
|  | AGACCGCGTC | CCGCCATGCA | GAGGTTATCA | CCCCTGCTGT | CCAGACCAAC | 5600 |
|  | TGGCAGAAAC | TCGAGGTCTT | TTGGGCGAAG | CACATGTGGA | ATTTCATCAG | 5650 |
|  | TGGGATACAA | TACTTGGCGG | GCCTGTCAAC | GCTGCCTGGT | AACCCCGCCA | 5700 |

FIG. 6C

|  | 10 | 20 | 30 | 40 | 50 |  |
|---|---|---|---|---|---|---|
|  | 1234567890 | 1234567890 | 1234567890 | 1234567890 | 1234567890 |  |
|  | TTGCTTCATT | GATGGCTTTT | ACAGCTGCCG | TCACCAGCCC | ACTAACCACT | 5750 |
|  | GGCCAAACCC | TCCTCTTCAA | CATATTGGGG | GGGTGGGTGG | CTGCCCAGCT | 5800 |
|  | CGCCGCCCCC | GGTGCCGCTA | CTGCCTTTGT | GGGTGCTGGC | CTAGCTGGCG | 5850 |
|  | CCGCCATCGG | CAGCGTTGGA | CTGGGAAGG | TCCTCGTGGA | CATTCTTGCA | 5900 |
|  | GGGTATGCCG | CGGGCGTGCC | GGGAGCTCTT | GTAGCATTCA | AGATCATGAG | 5950 |
|  | CGGTGAGGTC | CCCTCCACGG | AGGACCTGGT | CAATCTGCTG | CCCGCCATCC | 6000 |
|  | TCTCGCCTGG | AGCCCTTGTA | GTCGGTGTGG | TCTGCGCAGC | AATACTGCGC | 6050 |
|  | CGGCACGTTG | GCCCGGCGGA | GGGGCAGTG | CAATGGATGA | ACCGGCTAAT | 6100 |
|  | AGCCTTCGCC | TCCCGGGGA | ACCATGTTTC | CCCCACGCAC | TACGTGCCGG | 6150 |
|  | AGAGCGATGC | AGCCGCCCGC | GTCACTGCCA | TACTCAGCAG | CCTCACTGTA | 6200 |
|  | ACCCAGCTCC | TGAGGCGACT | GCATCAGTGG | ATAAGCTCGG | AGTGTACCAC | 6250 |
|  | TCCATGCTCC | GGTTCCTGGC | TAAGGACAT | CTGGGACTGG | ATATGCGAGG | 6300 |
|  | TGCTGAGCGA | CTTTAAGACC | TGGCTGAAAG | CCAAGCTCAT | GCCACAACTG | 6350 |
|  | CCTGGGATTC | CCTTTGTGTC | CTGCCAGCGC | GGGTATAGGG | GGGTCTGGCG | 6400 |
|  | AGGAGACGGC | ATTATGCACA | CTCGCTGCCA | CTGTGGAGCT | GAGATCACTG | 6900 |
|  | GACATGTCAA | AAACGGGACG | ATGAGGATCG | TCGTCCTAG | GACCTGCAGG | 6950 |
|  | AACATGTGGA | GTGGACGTT | CCCCATTAAC | GCCTACACCA | CGGCCCCTG | 6550 |
|  | TACTCCCCTT | CCTGCGCCGA | ACTATAAGTT | CGCGCTGTGG | AGGGTGTCTG | 6600 |
|  | CAGAGGAATA | CGTGGAGATA | AGGCGGGTGG | GGACTTCCA | CTACGTATCG | 6650 |
|  | GGTATGACTA | CTGACAATCT | TAAATGCCCG | TGCCAGATCC | CATCGCCCGA | 6700 |
|  | ATTTTTCACA | GAATTGGACG | GGGTGCGCCT | ACACAGGTTT | GCGCCCCCTT | 6750 |
|  | GCAAGCCCTT | GCTGCGGGAG | GAGGTATCAT | TCAGAGTAGG | ACTCCACGAG | 6800 |
|  | TACCCGGTGG | GGTCGCAATT | ACCTTGCGAG | CCCGAACCGG | ACGTAGCCGT | 6850 |
|  | GTTGACGTCC | ATGCTCACTG | ATCCCTCCCA | TATAACAGCA | GAGGCGGCCG | 6900 |
|  | GGAGAAGGTT | GGCGAGAGGG | TCACCCCCTT | CTATGGCCAG | CTCCTCGGCT | 6950 |
|  | AGCCAGCTGT | CCGCTCCATC | TCTCAAGGCA | ACTTGCACCG | CCAACCATGA | 7000 |
|  | CTCCCCTGAC | GCCGAGCTCA | TAGAGGCTAA | CCTCCTGTGG | AGGCAGGAGA | 7050 |
|  | TGGGCGGCAA | CATCACCAGG | GTTGAGTCAG | AGAACAAAGT | GGTGATTCTG | 7100 |
|  | GACTCCTTCG | ATCCGCTTGT | GGCAGAGGAG | GATGAGCGGG | AGGTCTCCGT | 7150 |
|  | ACCTGCAGAA | ATTCTGCCGA | AGTCTCGGAG | ATTCGCCCGG | GCCCTGCCCG | 7200 |
|  | TCTGGGCGCG | GCCGGACTAC | AACCCCCCGC | TAGTAGAGAC | GTGGAAAAAG | 7250 |
|  | CCTGACTACG | AACCACCTGT | GGTCCATGGC | TGCCCGCTAC | CACCTCCACG | 7300 |
|  | GTCCCCTCCT | GTGCCTCCGC | CTCGGAAAAA | GGGTACGGTG | GTCCTCACCG | 7350 |
|  | AATCAACCCT | ATCTACTGCC | TTGCCGAGC | TTGCACCAA | AAGTTTTGGC | 7400 |
|  | AGCTCCTCAA | CTTCCGGCAT | TACGGGCGAC | AATACGACAA | CATCCTCTGA | 7450 |
|  | GCCCGCCCCT | TCTGGCTGCC | CCCCGACTC | CGACGTTGAG | TCCTATTCTT | 7500 |
|  | CCATGCCCCC | CCTGAGGGG | GAGCCTGGGG | ATCCGGATCT | CAGCGACGGG | 7550 |
|  | TCATGGTCGA | CGGTCAGTAG | TGGGCCGAC | ACGGAAGATG | TCTGTGCTG | 7600 |

FIG. 6D

```
           10         20         30         40         50
    1234567890 1234567890 1234567890 1234567890 1234567890
    CTCAATGTCT TATTCCTGGA CAGGCGCACT CGTCACCCCG TGCGCTGCCG   7650
    AAGAACAAAA ACTGCCCATC AACGCACTGA GCAACTCGTT GCTACGCCAT   7700
    CACAATCTGG TGTATTCCAC CACTTCACGC AGTGCTTGCC AAAGGCAGAA   7750
    GAAAGTCACA TTTGACAGAC TGCAAGTTCT GGACAGCCAT TACCAGGACG   7800
    TGCTCAAGGA GGTCAAAGCA GCGGCGTCAA AAGTGAAGGC TAACTTGCTA   7850
    TCCGTAGAGG AAGCTTGCAG CCTGACGCCC CCACATTCAG CCAAATCCAA   7900
    GTTTGGCTAT GGGCAAAAG ACGTCCGTTG CCATCCAGA AAGGCCGTAG     7950
    CCCACATCAA CTCCGTGTGG AAAGACCTTC TGAAGACAG TGTAACACCA    8000
    ATAGACACTA CCATCATGGC CAAGAACGAG GTTTTCTGCG TTCAGCCTGA   8050
    GAAGGGGGGT CGTAAGCCAG CTCGTCTCAT CGTGTTCCCC GACCTGGGCG   8100
    TGCGCGTGTG CGAGAAGATG GCCCTGTACG ACGTGGTTAG CAAGCTCCCC   8150
    CTGCCCGTGA TGGAAGCTC CTACGGATTC CAATACTCAC CAGGACAGCG    8200
    GGTTGAATTC CTCGTGCAAG CGTGGAAGTC CAAGAAGACC CCGATGGGT    8250
    TCTCGTATGA TACCCGCTGT TTTGACTCCA CAGTCACTGA GAGCGACATC   8300
    CGTACGGAGG AGGCAATTTA CCAATGTTGT GACCTGGACC CCCAAGCCCG   8350
    CGTGGCCATC AAGTCCCTCA CTGAGAGGCT TTATGTTGGG GGCCCTCTTA   8400
    CCAATTCAAG GGGGAAAAC TGCGGCTACC GCAGGTGCCG CGCGAGCGGC    8450
    GTACTGACAA CTAGCTGTGG TAACACCCTC ACTTGCTACA TCAAGGCCCG   8500
    GGCAGCCTGT CGAGCCGCAG GCTCCAGGA CTGCACCATG CTCGTGTGTG    8550
    GCGACGACTT AGTCGTTATC TGTGAAAGTG CGGGGTCCA GGAGGACGCG    8600
    GCGAGCCTGA GAGCCTTCAC GGAGGCTATG ACCAGGTACT CCGCCCCCC    8650
    CGGGGACCCC CCACAACCAG AATACGACTT GGAGCTTATA ACATCATGCT   8700
    CCTCCAACGT GTCAGTCGCC CACGACGGCG CTGGAAAGAG GGTCTACTAC   8750
    CTTACCCGTG ACCCTACAAC CCCCCTCGCG AGAGCCGCGT GGGAGACAGC   8800
    AAGACACACT CCAGTCAATT CCTGGCTAGG CAACATAATC ATGTTGCCC    8850
    CCACACTGTG GGCGAGGATG ATACTGATGA CCCATTTCTT TAGCGTCCTC   8900
    ATAGCCAGGG ATCAGCTTGA ACAGGCTCTT AACTGTGAGA TCTACGGAGC   8950
    CTGCTACTCC ATAGAACCAC TGGATCTACC TCCAATCATT CAAAGACTCC   9000
    ATGCCTCAG CGCATTTTCA CTCCACAGTT ACTCTCCAGG TGAAATCAAT    9050
    AGGGTGGCCG CATGCCTCAG AAAACTTGGG GTCCCGCCCT TGCGAGCTTG   9100
    GAGACACCGG GCCCGGAGCG TCCGCGCTAG GCTTCTGTCC AGAGGAGGCA   9150
    GGGCTGCCAT ATGTGGCAAG TACCTCTTCA ACTGGGCAGT AAGAACAAAG   9200
    CTCAAACTCA CTCCAATAGC GGCCGCTGGC CGCTGGACT TGTCCGGTTG    9250
    GTTCACGGCT GGCTACAGCG GGGAGACAT TTATCACAGC GTGTCTCATG    9300
    CCCGGCCCG CTGGTTCTGG TTTTGCCTAC TCCTGCTCGC TGCAGGGGTA    9350
    GGCATCTACC TCCTCCCCAA CCGATGAAGG TGGGGTAAA CACTCCGGCC    9400
    TCTTAAGCCA TTCCTGTTTT TTTTTTTTTT TTTTTTTTTT TTTTTCTTTT   9450
    TTTTTTCTT TCCTTTCCTT CTTTTTTTCC TTTCTTTTTC CCTTCTTTAA    9500
```

FIG. 6E

```
          10         20         30         40         50
 1234567890 1234567890 1234567890 1234567890 1234567890
 TGGTGGCTCC ATCTTAGCCC TAGTCACGGC TAGCTGTGAA AGGTCCGTGA   9550
 GCCGCATGAC TGCAGAGAGT GCTGATACTG GCCTCTCTGC AGATCATGT    9599
```

FIG. 6F

```
           10         20         30         40         50
    1234567890 1234567890 1234567890 1234567890 1234567890
    MSTNPKPQRK TKRNINRRPQ DVKFPGGQI  VGGVYLLPRR GPRLGVRAIR    50
    KTSERSQPRG RRQPIPKARR PEGRIWAQPG YPWPLYGNEG CGWAGWLLSP   100
    RGSRPSWGPT DPRRRSRNLG KVIDTLTCGF ADLMGYIPLV GAPLGGAARA   150
    LAHGVRVLED GVNYATGNLP GCSFSIFLLA LLSCLTVPAS AYQVRNSSGL   200
    YHVINDCPNS SIVYEAADAI LHTPGCVPCV REGNASRCWV AVTPTVAIRD   250
    GKLPTTQLRR HIDLLVGSAT LCSALYVGDL CGSVFLVGQL FIFSPRRHWT   300
    TQDCNCSIYP GHITGHRMAW IMMMNWSPTA ALVVAQLLRI PQAIMDMIAG   350
    AHWGVLAGIA YFSMVGNWAK VLVVLLLFAG VDAEIHVTGG NAGRTTAGLV   400
    GLLTPGAKQN IQLININGSW HINSTALNCN ESLNTGWLAG LFYQHKFNSS   450
    GCPERLASCR RLTDFAQGWG PISYANGSGL DERPYCWHYP PRPCGIVPAK   500
    SVCGPVYCFT PSPVVVGTTD RSGAPTYSWG ANDIDVFVLN NTRPPLGNWF   550
    GCTWMNSTGF TKVCGAPPCV IGGVGNNTLL CPIDCFRKHP EATYSRCGSG   600
    PWITPRCMVD YPYRLWHYPC TINYTIFKVR MYVGGVEHRL EAACNWIRGE   650
    RCDLEDRDRS ELSPLLLSTT QWQVLPCSFT TLPALSTGLI HLHQNIVDVQ   700
    YLYGVGSSIA SWAIKWEYVV LLFLLLADAR VCSCLWMMLL ISQAEAALEN   750
    LVILNAASLA GIHGLVSFLV FFCFAWYLKG RWVPGAVYAL YGMWPLLLLL   800
    LALPQRAYAL DTEVAASCGG VVLVGLMALT LSPYYKRYIS WCMWWLQYFL   850
    TRVEAQLHVW VPPLNVRGGR DAVILLMCVV HPTLVFDITK LLLAIFGPLW   900
    ILQASLLKVP YFVRVQGLLR ICALARKIAG GHYVQMAIIK LGALTGTYVV   950
    NHLTPLRDWA HNGLRDLAVA VEPVVFSRME TKLITWGADT AACGDIINGL  1000
    PVSARRGQEI LLGPADGMVS KGWRLLAPIT AYAQQTRGLL GCIITSLTGR  1050
    DKNQVEGEVQ IVSTATQIFL ATCINGVCWT VYHGAGTRIT ASPKGPVIQM  1100
    YTNVDQDLVG WPAPQGSRSL TPCTCGSSDL YLVTRHADVI PVRRRGDSRG  1150
    SLLSPRPISY LKGSSGGPLL CPAGHAVGLF RAAVCTRGVA KAVDFIPVEN  1200
    LGTIMRSPVF TDNSSPPAVP QSFQVAHLHA PTGSGKSTKV PAAYAAQGYK  1250
    VLVLNPSVAA TLGFGAYMSK AHGVDPNIRT GVRTITTGSP ITYSTYGKFL  1300
    ADGGCSGGAY DIIICDECHS TDATSILGIG TVLDQAETAG ARLVVLATAT  1350
    PPGSVTVSHP NIEEVALSTT GEIPFYGKAI PLEVIKGGRH LIFCHSKKKC  1400
    DELAAKLVAL GINAVAYYRG LDVSVIPTSG DVVVVSTDAL MTGFTGDFDS  1450
    VIDCNTCVTQ TVDFSLDPTF TIETTTLPQD AVSRTQRRGR TGRGKPGIYR  1500
    FVAPGERPSG MFDSSVLCEC YDAGCAWYEL TPAETTVRLR AYMNTPGLPV  1550
    CQDHLEFWEG VFTGLTHIDA HFLSQTKQSG ENFPYLVAYQ ATVCARAQAP  1600
    PPSWDQMWKC LIRLKPTLHG PTPLLYRLGA VQNEVTLTHP ITKYIMTCMS  1650
    ADLEVVTSTW VLVGGVLAAL AAYCLSTGCV VIVGRIVLSG KPAIIPDREV  1700
    LYQEFDEMEE CSQHLPYIEQ GMMLAEQFKQ KALGLLQTAS RHAEVITPAV  1750
    QTNWQKLEVF WAKHMWNFIS GIQYLAGLST LPGNPAIASL MAFTAAVTSP  1800
    LTTGQTLLFN ILGGWVAAQL AAPGAATAFV GAGLAGAAIG SVGLGKVLVD  1850
    ILAGYGAGVA GALVAFKIMS GEVPSTEDLV NLLPAILSPG ALVVGVVCAA  1900
```

FIG. 6G

```
            10          20          30          40          50
     1234567890  1234567890  1234567890  1234567890  1234567890
     ILRRHVGPGE  GAVQWMNRLI  AFASRGNHVS  PIHYVPESDA  AARVIAILSS   1950
     LIVIQLLRRL  HQWISSECTT  PCSGSWLRDI  WDWICEVLSD  FKIWLKAKLM   2000
     PQLPGIPFVS  CQRGYRGVWR  GDGIMHIRCH  CGAEITGHVK  NGIMRIVGPR   2050
     TCRNMWSGIF  PINAYTIGPC  TPLPAPNYKF  ALWRVSAEEY  VEIRRVGDFH   2100
     YVSGMTIDNL  KCPCQIPSPE  FFTELDGVRL  HRFAPPCKPL  LREEVSFRVG   2150
     IHEYPVGSQL  PCEPEPDVAV  LTSMLTDPSH  ITAEAAGRRL  ARGSPPSMAS   2200
     SSASQLSAPS  LKATCTANHD  SPDAELIEAN  LLWRQEMGGN  ITRVESENKV   2250
     VILDSFDPLV  AEEDEREVSV  PAEILRKSRR  FARALPVWAR  PDYNPPLVET   2300
     WKKPDYEPPV  VHGCPLPPPR  SPPVPPPRKK  RIVVLTESTL  STALAELATK   2350
     SFGSSSTSGI  TGINTTTSSE  PAPSGCPPDS  DVESYSSMPP  LEGEPGDPDL   2400
     SDGSWSTVSS  GADTEDVVCC  SMSYSWIGAL  VTPCAAEEQK  LPINALSNSL   2450
     LRHHNLVYST  TSRSACQRQK  KVTFDRLQVL  DSHYQDVLKE  VKAAASKVKA   2500
     NLLSVEEACS  LTPPHSAKSK  FGYGAKDVRC  HARKAVAHIN  SWWKDLLEDS   2550
     VTPIDTTIMA  KNEVFCVQPE  KGGRKPARLI  VFPDLGVRVC  EKMALYDVVS   2600
     KLPLAVMGSS  YGFQYSPGQR  VEFLVQAWKS  KKTPMGFSYD  TRCFDSIVTE   2650
     SDIRTEEATY  QCCDLDPQAR  VAIKSLTERL  YVGGPLINSR  GENCGYRRCR   2700
     ASGVLTTSCG  NTLTCYIKAR  AACRAAGLQD  CIMLVCGDDL  VVICESAGVQ   2750
     EDAASLRAFT  EAMIRYSAPP  GDPPQPEYDL  ELITSCSSNV  SVAHDGAGKR   2800
     VYYLTRDPTT  PLARAAWETA  RHTPVNSWLG  NIIMFAPTLW  ARMILMIHFF   2850
     SVLIARDQLE  QALNCEIYGA  CYSIEPLDLP  PIIQRLHGLS  AFSLHSYSPG   2900
     EINRVAACLR  KLGVPPLRAW  RHRARSVRAR  LLSRGGRAAI  CGKYLFNWAV   2950
     RTKLKLTPIA  AAGRLDLSGW  FTAGYSGGDI  YHSVSHARPR  WFWFCLLLLA   3000
     AGVGIYLLPN  R                                               3011
```

FIG. 6H

|  |  |  |  |  |  |
|---|---|---|---|---|---|
| 10 | 20 | 30 | 40 | 50 | |
| 1234567890 | 1234567890 | 1234567890 | 1234567890 | 1234567890 | |
| GCCAGCCCCC | TGATGGGGGC | GACACTCCAC | CATGAATCAC | TCCCCTGTGA | 50 |
| GGAACTACTG | TCTTCACGCA | GAAAGCGTCT | AGCCATGGCG | TTAGTATGAG | 100 |
| TGTCGTGCAG | CCTCCAGGAC | CCCCCCTCCC | GGAGAGCCA | TAGTGGTCTG | 150 |
| CGGAACCGGT | GAGTACACCG | GAATTGCCAG | GACGACCGGG | TCCTTTCTTG | 200 |
| GATCAACCCG | CTCAATGCCT | GGAGATTTGG | GCGTGCCCCC | GCGAGACTGC | 250 |
| TAGCCGAGTA | GTGTTGGGTC | GCGAAAGGCC | TTGTGGTACT | GCCTGATAGG | 300 |
| GTGCTTGCGA | GTGCCCCGGG | AGGTCTCGTA | GACCGTGCAC | CATGAGCACG | 350 |
| AATCCTAAAC | CTCAAAGAAA | AACCAAACGT | AACACCAACC | GCCGCCACA | 400 |
| GGACGTCAAG | TTCCCGGGCG | GTGGTCAGAT | CGTTGGTGGA | GTTTACCTGT | 450 |
| TGCCGCGCAG | GGGCCCCAGG | TTGGGTGTGC | GCGCGACTAG | GAAGGCTTCC | 500 |
| GAGCGGTCGC | AACCTCGTGG | AAGGCGACAA | CCTATCCCAA | AGGCTCGCCG | 550 |
| ACCCGAGGGC | AGGGCCTGGG | CTCAGCCCGG | GTACCCTTGG | CCCCTCTATG | 600 |
| GCAATGAGGG | CCTGGGGTGG | GCAGGATGGC | TCCTGTCACC | CCGCGGCTCC | 650 |
| CGGCCTAGTT | GGGGCCCCAC | GGACCCCGG | CGTAGGTCGC | GTAACTTGGG | 700 |
| TAAGGTCATC | GATACCCTTA | CATGCGGCTT | CGCCGATCTC | ATGGGTACA | 750 |
| TTCCGCTCGT | CGGCGCCCCC | CTAGGGGCG | CTGCCAGGGC | CTTGGCACAC | 800 |
| GGTGTCCGGG | TTCTGGAGGA | CGGCGTGAAC | TATGCAACAG | GGAACTTGCC | 850 |
| CGGTTGCTCT | TTCTCTATCT | TCCTCTTGCC | TCTGCTGTCC | TGTTTGACCA | 900 |
| TCCCAGCTTC | CGCTTATGAA | GTGCGCAACG | TGTCCGGGAT | ATACCATGTC | 950 |
| ACGAACGACT | GCTCCAACTC | AAGCATTGTG | TATGAGGCAG | CGGACGTGAT | 1000 |
| CATGCATACT | CCCGGGTGCG | TGCCCTGTGT | TCAGGAGGGT | AACAGCTCCC | 1050 |
| GTTGCTGGGT | AGCGCTCACT | CCCACGCTCG | CGGCCAGGAA | TGCCAGCGTC | 1100 |
| CCCACTACGA | CAATACGACG | CCACGTCGAC | TTGCTCGTTG | GGACGGCTGC | 1150 |
| TTTCTGCTCC | GCTATGTACG | TGGGGATCT | CTGCGGATCT | ATTTTCCTCG | 1200 |
| TCTCCCAGCT | GTTCACCTTC | TGCCTCGCC | GGCATGAGAC | AGTGCAGGAC | 1250 |
| TGCAACTGCT | CAATCTATCC | CGGCCATGTA | TCAGGTCACC | GCATGGCTTG | 1300 |
| GGATATGATG | ATGAACTGGT | CACCTACAAC | AGCCCTAGTG | GTGTCGCAGT | 1350 |
| TGCTCCGGAT | CCCACAAGCT | GTCGTGGACA | TGGTGGCGGG | GCCCACTGG | 1400 |
| GGAGTCCTGG | CGGGCCTTGC | CTACTATTCC | ATGGTAGGGA | ACTGGCTAA | 1450 |
| GGTTCTGATT | GTGGCGCTAC | TCTTTGCCGG | CGTTGACGGG | GAGACCCACA | 1500 |
| CGACGGGGAG | GGTGGCCGGC | CACACCACCT | CGGGTTCAC | GTCCCTTTTC | 1550 |
| TCATCTGGGG | CGTCTCAGAA | AATCCAGCTT | GTGAATACCA | ACGGCAGCTG | 1600 |
| GCACATCAAC | AGGACTGCCC | TAAATTGCAA | TGACTCCCTC | CAAACTGGGT | 1650 |
| TCTTTGCCGC | GCTGTTTTAC | GCACACAAGT | TCAACTCGTC | CGGGTGCCCG | 1700 |
| GAGCGCATGG | CCAGCTGCCG | CCCCATTGAC | TGGTTCGCCC | AGGGGTGGGG | 1750 |
| CCCCATCACC | TATACTAAGC | CTAACAGCTC | GGATCAGAGG | CCTTATTGCT | 1800 |
| GGCATTACGC | GCCTCGACCG | TGTGGTGTCG | TACCCGCGTC | GCAGGTGTGT | 1850 |
| GGTCCAGTGT | ATTGTTTCAC | CCCAAGCCCT | GTTGTGGTGG | GGACCACCGA | 1900 |

FIG. 7A

|  | 10 | 20 | 30 | 40 | 50 |  |
|---|---|---|---|---|---|---|
|  | 1234567890 | 1234567890 | 1234567890 | 1234567890 | 1234567890 |  |
|  | TCGTTCCGGT | GTCCCTACGT | ATAGCTGGGG | GGAGAATGAG | ACAGACGTGA | 1950 |
|  | TGCTCCTCAA | CAACACGCGT | CCGCCACAAG | GCAACTGGTT | CGGCTGTACA | 2000 |
|  | TGGATGAATA | GTACTGGGTT | CACTAAGACG | TGCGGAGGTC | CCCCGTGTAA | 2050 |
|  | CATCGGGGGG | GTCGGTAACC | GCACCTTGAT | CTGCCCCACG | GACTGCTTCC | 2100 |
|  | GGAAGCACCC | CGAGGCTACT | TACACAAAAT | GTGGCTCGGG | GCCCTGGTTG | 2150 |
|  | ACACCTAGGT | GCCTAGTAGA | CTACCCATAC | AGGCTTTGGC | ACTACCCCTG | 2200 |
|  | CACTCTCAAT | TTTCCATCT | TTAAGGTTAG | GATGTATGTG | GGGGCGTGG | 2250 |
|  | AGCACAGGCT | CAATGCCGCA | TGCAATTGGA | CTCGAGGAGA | GCGCTGTAAC | 2300 |
|  | TTGGAGGACA | GGGATAGGTC | AGAACTCAGC | CCGCTGCTGC | TGTCTACAAC | 2350 |
|  | AGAGTGGCAG | ATACTGCCCT | GTGCTTTCAC | CACCCTACCG | GCTTTATCCA | 2400 |
|  | CTGGTTTGAT | CCATCTCCAT | CAGAACATCG | TGGACGTGCA | ATACCTGTAC | 2450 |
|  | GGTGTAGGGT | CAGCGTTTGT | CTCCTTTGCA | ATCAAATGGG | AGTACATCCT | 2500 |
|  | GTTGCTTTTC | CTTCTCCTGG | CAGACGCGCG | CGTGTGTGCC | TGCTTGTGA | 2550 |
|  | TGATGCTGCT | GATAGCCCAG | GCTGAGGCCG | CCTTAGAGAA | CTTGGTGGTC | 2600 |
|  | CTCAATGCGG | CGTCCGTGGC | CGGAGCGCAT | GGTATTCTCT | CCTTTCTTGT | 2650 |
|  | GTTCTTCTGC | GCCGCCTGGT | ACATTAAGGG | CAGGCTGGCT | CCTGGGGCGG | 2700 |
|  | CGTATGCTTT | TTATGGCGTA | TGGCCGCTGC | TCCTGCTCCT | ACTGGCGTTA | 2750 |
|  | CCACCACGAG | CTTACGCCTT | GGACCGGGAG | ATGGCTGCAT | CGTCCGGGGG | 2800 |
|  | TGCGGTTCTT | GTAGGTCTGG | TATTCTTGAC | CTTGTCACCA | TACTACAAAG | 2850 |
|  | TGTTTCTCAC | TAGGCTCATA | TGGTGGTTAC | AATACTTTAT | CACCAGAGCC | 2900 |
|  | GAGGCGCACA | TGCAAGTGTG | GGTCCCCCCC | CTCAACGTTC | GGGGAGGCCG | 2950 |
|  | CGATGCCATC | ATCCTCCTCA | CGTGTGCGGT | TCATCCAGAG | TTAATTTTTG | 3000 |
|  | ACATCACCAA | ACTCCTGCTC | GCCATACTCG | GCCCGCTCAT | GGTGCTCCAG | 3050 |
|  | GCTGGCATAA | CGAGAGTGCC | GTACTTCGTG | CGCGCTCAAG | GCTCATTCG | 3100 |
|  | TGCATGCATG | TTAGTGCGAA | AAGTCGCCGG | GGGTCATTAT | GTCCAAATGG | 3150 |
|  | TCTTCATGAA | GCTGGGCGCG | CTGACAGGTA | CGTACGTTTA | TAACCATCTT | 3200 |
|  | ACCCCACTGC | GGGACTGGGC | CCACGCGGGC | CTACGAGACC | TTGCGGTGGC | 3250 |
|  | GGTAGAGCCC | GTCGTCTTCT | CCGCCATGGA | GACCAAGGTC | ATCACCTGGG | 3300 |
|  | GAGCAGACAC | CGCTGCGTGT | GGGACATCA | TCTTGGGTCT | ACCCGTCTCC | 3350 |
|  | GCCCGAAGGG | GGAAGGAGAT | ATTTTTGGGA | CCGGCTGATA | GTCTCGAAGG | 3400 |
|  | GCAAGGGTGG | CGACTCCTTG | CGCCCATCAC | GGCCTACTCC | CAACAAACGC | 3450 |
|  | GGGGCGTACT | TGGTTGCATC | ATCACTAGCC | TCACAGGCCG | GGACAAGAAC | 3500 |
|  | CAGGTCGAAG | GGAGGTTCA | AGTGGTTTCT | ACCGCAACAC | AATCTTTCCT | 3550 |
|  | GGCGACCTGC | ATCAACGGCG | TGTGCTGGAC | TCTCTACCAT | GGCGCTGGCT | 3600 |
|  | CGAAGACCCT | AGCCGGTCCA | AAAGGTCCAA | TCACCCAAAT | GTACACCAAT | 3650 |
|  | GTAGACCTGG | ACCTCGTCGG | CTGGCAGGCG | CCCCCCGGGG | CGCGCTCCAT | 3700 |
|  | GACACCATGC | AGCTGTGGCA | GCTCGGACCT | TTACTTGGTC | ACGAGACATG | 3750 |
|  | CTGATGTCAT | TCCGGTGCGC | CGGCGAGGCG | ACAGCAGGGG | AAGTCTACTC | 3800 |

FIG. 7B

|   |   |   |   |   |   |
|---|---|---|---|---|---|
| 10 | 20 | 30 | 40 | 50 | |
| 1234567890 | 1234567890 | 1234567890 | 1234567890 | 1234567890 | |
| TCCCCCAGGC | CCGTCTCCTA | CCTGAAAGGC | TCCTCGGGTG | GTCCATTGCT | 3850 |
| TTGCCCTTCG | GGGCACGTCG | TGGCGTCTT | CCGGCTGCT | GTGTGCACCC | 3900 |
| GGGGGTCGC | GAAGGCGGTG | GACTTCATAC | CCGTTGAGTC | TATGGAAACT | 3950 |
| ACCATGCGGT | CTCCGGTCTT | CACAGACAAC | TCAACCCCC | CGGCTGTACC | 4000 |
| GCAGACATTC | CAAGTGGCAC | ATCTGCACGC | TCCTACTGGC | AGCGGCAAGA | 4050 |
| GCACCAAAGT | GCCGGCTGCG | TATGCAGCCC | AAGGGTACAA | GGTGCTCGTC | 4100 |
| CTGAACCCGT | CCGTTGCCGC | CACCTTAGGG | TTTGGGGCGT | ATATGTCCAA | 4150 |
| GGCACACGGT | ATCGACCCTA | ACATCAGAAC | TGGGGTAAGG | ACCATTACCA | 4200 |
| CGGGCGGCTC | CATTACGTAC | TCCACCTATG | GCAAGTTCCT | TGCCGACGGT | 4250 |
| GGCTGTTCTG | GGGGCGCCTA | TGACATCATA | ATATGTGATG | AGTGCCACTC | 4300 |
| AACTGACTCG | ACTACCATCT | TGGGCATCGG | CACAGTCCTG | GACCAAGCGG | 4350 |
| AGACGGCTGG | AGCGCGGCTC | GTCGTGCTCG | CCACCGCTAC | ACCTCCGGA | 4400 |
| TCGGTTACCG | TGCCACACCC | CAATATCGAG | GAAATAGGCC | TGTCCAACAA | 4450 |
| TGGAGAGATC | CCCTTCTATG | GCAAAGCCAT | CCCCATTGAG | GCCATCAAGG | 4500 |
| GGGGAGGCA | TCTCATTTTC | TGCCATTCCA | AGAAGAAATG | TGACGAGCTC | 4550 |
| GCCGCAAAGC | TGACAGGCCT | CGGACTGAAC | GCTGTAGCAT | ATTACCGGGG | 4600 |
| CCTTGATGTG | TCCGTCATAC | CGCCTATCGG | AGACGTCGTT | GTCGTGGCAA | 4650 |
| CAGACGCTCT | AATGACGGGT | TTCACCGGCG | ATTTGACTC | AGTGATCGAC | 4700 |
| TGCAATACAT | GTGTCACCCA | GACAGTCGAC | TTCAGCTTGG | ATCCCACCTT | 4750 |
| CACCATTGAG | ACGACGACCG | TGCCCAAGA | CGCGGTGTCG | CGCTCGCAAC | 4800 |
| GGCGAGGTAG | AACTGGCAGG | GGTAGGAGTG | GCATCTACAG | GTTTGTGACT | 4850 |
| CCAGGAGAAC | GGCCCTCGGG | CATGTTCGAT | TCTTCGGTCC | TGTGTGAGTG | 4900 |
| CTATGACGCG | GGCTGTGCTT | GGTATGAGCT | CACGCCCGCT | GAGACCTCGG | 4950 |
| TTAGGTTGCG | GGCTTACCTA | AATACACCAG | GGTTGCCCGT | CTGCCAGGAC | 5000 |
| CATCTGGAGT | TCTGGGAGAG | CGTCTTCACA | GGCCTCACCC | ACATAGATCC | 5050 |
| CCACTTCCTG | TCCAGACTA | AACAGGCAGG | AGACAACTTT | CCTTACCTGG | 5100 |
| TGGCATATCA | AGCTACAGTG | TGCGCCAGGG | CTCAAGCTCC | ACCTCCATCG | 5150 |
| TGGACCAAA | TGTGGAAGTG | TCTCATACGG | CTGAAACCTA | CACTGCACGG | 5200 |
| GCCAACACCC | CTGCTGTATA | GGCTAGGAGC | CGTCCAAAAT | GAGGTCATCC | 5250 |
| TCACACACCC | CATAACTAAA | TACATCATGG | CATGCATGTC | GGCTGACCTG | 5300 |
| GAGGTCGTCA | CTAGCACCTG | GGTGCTGGTA | GGCGGAGTCC | TTGCAGCTTT | 5350 |
| GGCCGCATAC | TGCCTGACGA | CAGGCAGTGT | GGTCATTGTG | GGCAGGATCA | 5400 |
| TCTTGTCCGG | GAAGCCAGCT | GTCGTTCCCG | ACAGGGAAGT | CCTCTACCAG | 5450 |
| GAGTTCGATG | AGATGGAAGA | GTGTGCCTCA | CAACTTCCTT | ACATCGAGCA | 5500 |
| GGGAATGCAG | CTCGCCGAGC | AATTCAAGCA | AAAGGCGCTC | GGGTTGTTGC | 5550 |
| AAACGGCCAC | CAAGCAAGCG | GAGGCTGCTG | CTCCCGTGGT | GGAGTCCAAG | 5600 |
| TGGCGAGCCC | TTGAGACCTT | CTGGGCGAAG | CACATGTGGA | ATTTCATCAG | 5650 |
| CGGAATACAG | TACCTAGCAG | GCTTATCCAC | TCTGCCTGGA | AACCCCGCGA | 5700 |

FIG. 7C

|  | 10 | 20 | 30 | 40 | 50 | |
|---|---|---|---|---|---|---|
|  | 1234567890 | 1234567890 | 1234567890 | 1234567890 | 1234567890 | |
|  | TAGCATCATT | GATGGCATTT | ACAGCTTCTA | TCACTAGCCC | GCTCACCACC | 5750 |
|  | CAAAACACCC | TCCTGTTTAA | CATCTTGGGG | GGATGGGTGG | CTGCCCAACT | 5800 |
|  | CGCTCCTCCC | AGCGCTGCGT | CAGCTTTCGT | GGGCGCCGGC | ATCGCCGGAG | 5850 |
|  | CGGCTGTTGG | CAGCATAGGC | CTTGGGAAGG | TGCTCGTGGA | CATCTTGGCG | 5900 |
|  | GGCTATGGGG | CAGGGGTAGC | CGGCGCACTC | GTGGCTTTA | AGGTCATGAG | 5950 |
|  | CGGCGAGGTG | CCCTCCACCG | AGGACCTGGT | CAACTTACTC | CCTGCCATCC | 6000 |
|  | TCTCTCCTGG | TGCCCTGGTC | GTCGGGGTCG | TGTGCGCAGC | AATACTGCGT | 6050 |
|  | CGGCACGTGG | GCCCGGGAGA | GGGGCTGTG | CAGTGGATGA | ACCGCTGAT | 6100 |
|  | AGCGTTCGCT | TCGCGGGGTA | ACCACGTCTC | CCCTACGCAC | TATGTGCCTG | 6150 |
|  | AGAGCGACGC | TGCAGCACGT | GTCACTCAGA | TCCTCTCTAG | CCTTACCATC | 6200 |
|  | ACTCAACTGC | TGAAGCGGCT | CCACCAGTGG | ATTAATGAGG | ACTGCTCTAC | 6250 |
|  | GCCATGCTCC | GGCTCGTGGC | TAAGGGATGT | TTGGGATTGG | ATATGCACGG | 6300 |
|  | TGTTGACTGA | CTTCAAGACC | TGGCTCCAGT | CCAAACTCCT | GCCGCGGTTA | 6350 |
|  | CCGGGAGTCC | CTTTCCTGTC | ATGCCAACGC | GGGTACAAGG | GAGTCTGCCG | 6400 |
|  | GGGGACGGC | ATCATGCAAA | CCACCTGCCC | ATGCGGAGCA | CAGATCGCCG | 6450 |
|  | GACATGTCAA | AAACGGTTCC | ATGAGGATCG | TAGGGCCTAG | AACCTGCAGC | 6500 |
|  | AACACGTGGC | ACGGAACGTT | CCCCATCAAC | GCATACACCA | CGGGACCTTG | 6550 |
|  | CACACCCTCC | CCGGCGCCCA | ACTATTCCAG | GCGCTATGG | CGGGTGGCTG | 6600 |
|  | CTGAGGAGTA | CGTGGAGGTT | ACGCGTGTGG | GGATTTCCA | CTACGTGACG | 6650 |
|  | GGCATGACCA | CTGACAACGT | AAAGTGCCCA | TGCCAGGTTC | CGGCCCCGA | 6700 |
|  | ATTCTTCACG | GAGGTGGATG | GAGTGCGGTT | GCACAGGTAC | GCTCCGGCGT | 6750 |
|  | GCAAACCTCT | TCTACGGGAG | GACGTCACGT | TCCAGGTCGG | GCTCAACCAA | 6800 |
|  | TACTTGGTCG | GGTCGCAGCT | CCCATGCGAG | CCCGAACCGG | ACGTAACAGT | 6850 |
|  | GCTTACTTCC | ATGCTCACCG | ATCCCTCCCA | CATTACAGCA | GAGACGGCTA | 6900 |
|  | AGCGTAGGCT | GGCTAGAGGG | TCTCCCCCCT | CTTTAGCCAG | CTCATCAGCT | 6950 |
|  | AGCCAGTTGT | CTGCGCCTTC | TTTGAAGGCG | ACATGCACTA | CCCACCATGA | 7000 |
|  | CTCCCCGGAC | GCTGACCTCA | TCGAGGCCAA | CCTCTTGTGG | CGGCAGGAGA | 7050 |
|  | TGGGCGGAAA | CATCACTCGC | GTGGAGTCAG | AGAATAAGGT | AGTAATTCTG | 7100 |
|  | GACTCTTTCG | AACCGCTTCA | CGCGGAGGGG | GATGAGAGGG | AGATATCCGT | 7150 |
|  | CGCGGCGGAG | ATCCTGCGAA | AATCCAGGAA | GTTCCCCTCA | GCGTTGCCCA | 7200 |
|  | TATGGGCACG | CCCGGACTAC | AATCCTCCAC | TGCTAGAGTC | CTGGAAGGAC | 7250 |
|  | CCGGACTACG | TCCCTCCGGT | GGTACACGGA | TGCCCATTGC | CACCTACCAA | 7300 |
|  | GGCTCCTCCA | ATACCACCTC | CACGGAGAAA | GAGGACGGTT | GTCCTGACAG | 7350 |
|  | AATCCAATGT | GTCTTCTGCC | TTGCGGAGC | TCGCCACTAA | GACCTTCGGT | 7400 |
|  | AGCTCCGGAT | CGTCGGCCGT | TGATAGCGGC | ACGGCGACCG | CCCTTCCTGA | 7450 |
|  | CCTGGCCTCC | GACGACGGTG | ACAAAGGATC | CGACGTTGAG | TGTACTCCT | 7500 |
|  | CCATGCCCCC | CCTTGAAGGG | GAGCCGGGGG | ACCCCGATCT | CAGCGACGGG | 7550 |
|  | TCTTGGTCTA | CCGTGAGTGA | GGAGGCTAGT | GAGGATGTCG | TCTGCTGCTC | 7600 |

FIG. 7D

```
         10         20         30         40         50
1234567890 1234567890 1234567890 1234567890 1234567890
AATGTCCTAT ACGTGGACAG GCGCCCTGAT CACGCCATGC GCTGCGGAGG    7650
AAAGTAAGCT GCCCATCAAC CCGTTGAGCA ACTCTTTGCT GCGTCACCAC    7700
AACATGGTCT ACGCCACAAC ATCCCGCAGC GCAAGCCTCC GGCAGAAGAA    7750
GGTCACCTTT GACAGATTGC AAGTCCTGGA TGATCATTAC CGGGACGTAC    7800
TCAAGGAGAT GAAGGCGAAG GCGTCCACAG TTAAGGCTAA GCTTCTATCT    7850
ATAGAGGAGG CCTGCAAGCT GACGCCCCCA CATTCGGCCA AATCCAAATT    7900
TGGCTATCGG GCAAAGGACG TCCGGAACCT ATCCAGCAGG GCCGTTAACC    7950
ACATCCGCTC CGTGTGGGAG GACTTGCTGG AAGACACTGA AACACCAATT    8000
GACACCACCA TCATGGCAAA AAGTGAGGTT TTCTGCGTCC AACCAGAGAA    8050
GGGAGGCCGC AAGCCAGCTC GCCTTATCGT ATTCCCAGAC CTGGGAGTTC    8100
GTGTATGCGA GAAGATGGCC CTTTACGACG TGGTCTCCAC CCTTCCTCAG    8150
GCCGTGATGG GCTCCTCATA CGGATTTCAA TACTCCCCCA AGCAGCGGGT    8200
CGAGTTCCTG GTGAATACCT GGAAATCAAA GAAATGCCCT ATGGGCTTCT    8250
CATATGACAC CCGCTGTTTT GACTCAACGG TCACTGAGAG TGACATTCGT    8300
GTTGAGGAGT CAATTTACCA ATGTTGTGAC TTGGCCCCCG AGCCAGACA    8350
GGCCATAAGG TGCTCACAG AGCGGCTTTA CATCGGGGT CCCCTGACTA    8400
ACTCAAAAGG GCAGAACTGC GGTTATCGCC GGTGCCGCGC AAGTGGCGTG    8450
CTGACGACTA GCTGCGGTAA TACCCTCACA TGTTACTTGA AGGCCACTGC    8500
AGCCTGTCGA GCTGCAAAGC TCAGGACTG CACGATGCTC GTGAACGGAG    8550
ACGACCTTGT CGTTATCTGT GAAAGCGCGG GAACCCAGGA GGATGCGGCG    8600
GCCCTACGAG CCTTCACGGA GGCTATGACT AGGTATTCCG CCCCCCCCGG    8650
GGATCCGCCC CAACCAGAAT ACGACCTGGA GCTGATAACA TCATGTTCCT    8700
CCAATGTGTC AGTCGCGCAC GATGCATCTG GCAAAAGGGT ATACTACCTC    8750
ACCCGTGACC CCACCACCCC CCTTGCACGG GCTGCGTGGG AGACAGCTAG    8800
ACACACTCCA ATCAACTCTT GGCTAGGCAA TATCATCATG TATGCGCCCA    8850
CCCTATGGGC AAGGATGATT CTGATGACTC ACTTTTTCTC CATCCTTCTA    8900
GCTCAAGAGC AACTTGAAAA AGCCCTGGAT TGTCAGATCT ACGGGCTTG    8950
CTACTCCATT GAGCCACTTG ACCTACCTCA GATCATTGAA CGACTCCATG    9000
GTCTTAGCGC ATTTACACTC CACAGTTACT CTCCAGGTGA GATCAATAGG    9050
GTGGCTTCAT GCCTCAGGAA ACTTGGGGTA CCACCCTTGC GAACCTGGAG    9100
ACATCGGGCC AGAAGTGTCC GCGCTAAGCT ACTGTCCCAG GGGCGGAGGG    9150
CCGCCACTTG TGGCAGATAC CTCTTTAACT GGCAGTAAG GACCAAGCTT    9200
AAACTCACTC CAATCCCGGC CGCGTCCCAG CTGGACTTGT CTGGCTGGTT    9250
CGTCGCTGGT TACAGCGGGG GAGACATATA TCACAGCCTG TCTCGTGCCC    9300
GACCCCGCTG GTTTCCGTTG TGCCTACTCC TACTTTCTGT AGGGGTAGGC    9350
ATTTACCTGC TCCCCAACCG ATGAACGGGG AGCTAACCAC TCCAGGCCTT    9400
AAGCCATTTC CTGTTTTTTT TTTTTTTTTT TTTTTTTTTT TCTTTTTTT    9450
TTTCTTTCCT TTCCTTCTTT TTTTCCTTTC TTTTTCCCTT CTTTAATGGT    9500
```

FIG. 7E

|  10 | 20 | 30 | 40 | 50 | |
|---|---|---|---|---|---|
| 1234567890 | 1234567890 | 1234567890 | 1234567890 | 1234567890 | |
| GGCTCCATCT | TAGCCCTAGT | CACGGCTAGC | TGTGAAAGGT | CCGTGAGCCG | 9550 |
| CATGACTGCA | GAGAGTGCTG | ATACTGGCCT | CTCTGCAGAT | CATGT | 9595 |

FIG. 7F

```
              10         20         30         40         50
         1234567890 1234567890 1234567890 1234567890 1234567890
         MSINPKPQRK TKRNINRRPQ DVKFPGGQI  VGGVYLLPRR GPRLGVRATR    50
         KASERSQPRG RRQPIPKARR PEGRAWAQPG YPWPLYGNEG LGWAGWLLSP   100
         RGSRPSWGPT DPRRRSRNLG KVIDTLTCGF ADLMGYIPLV GAPLGGAARA   150
         LAHGVRVLED GVNYATGNLP GCSFSIFLLA LLSCLTIPAS AYEVRNVSGI   200
         YHVINDCSNS SIVYEAADVI MHTPGCVPCV QEGNSSRCWW ALTPTLAARN   250
         ASVPTTTIRR HVDLLVGTAA FCSAMYVGDL CGSIFLVSQL FTFSPRRHET   300
         VQDCNCSIYP GHVSGHRMAW DMMMNWSPTT ALVVSQLLRI PQAVVDMVAG   350
         AHWGVLAGLA YYSMVGNWAK VLIVALLFAG VDGETHTTGR VAGHITSGFT   400
         SLFSSGASQK IQLVNINGSW HINRTALNCN DSLQTGFFAA LFYAHKFNSS   450
         GCPERMASCR PIDWFAQGWG PITYTKPNSS DQRPYCWHYA PRPCGVVPAS   500
         QVCGPVYCFT PSPVVVGTID RSGVPTYSWG ENEIDVMLLN NIRPPQGWWF   550
         GCIWMNSTGF TKTCGGPPCN IGGVGNRTLI CPTDCFRKHP EATYTKCGSG   600
         PWLTPRCLVD YPYRLWHYPC TLNFSTFKVR MYVGGVEHRL NAACNWTRGE   650
         RCNLEDRDRS ELSPLLLSTT EWQILPCAFT TLPALSTGLI HLHQNIVDVQ   700
         YLYGVGSAFV SFAIKWEYIL LLFLLLADAR VCACLWMMLL IAQAEAALEN   750
         LVVLNAASVA GAHGILSFLV FFCAAWYIKG RLAPGAAYAF YGVWPLLLLL   800
         LALPPRAYAL DREMAASCGG AVLVGLVFLT LSPYYKVFLT RLIWWLQYFI   850
         TRAEAHMQWW VPPLNVRGGR DAIILLTCAV HPELIFDITK LLLAILGPLM   900
         VLQAGITRVP YFVRAQGLIR ACMLVRKVAG GHYVQMVFMK LGALTGTYVY   950
         NHLTPLRDWA HAGLRDLAVA VEPVVFSAME TKVITWGADT AACGDIILGL  1000
         PVSARRGKEI FLGPADSLEG QGWRLLAPTT AYSQQTRGVL GCIITSLTGR  1050
         DKNQVEGEVQ WVSTATQSFL ATCINGVCWT VYHGAGSKTL AGPKGPITQM  1100
         YTNVDLDLVG WQAPPGARSM TPCSCGSSDL YLVTRHADVI PVRRRGDSRG  1150
         SLLSPRPVSY LKGSSGGPLL CPSGHVVGVF RAAVCTRGVA KAVDFIPVES  1200
         METTMRSPVF TDNSTPPAVP QTFQVAHLHA PTGSGKSTKV PAAYAAQGYK  1250
         VLVLNPSVAA TLGFGAYMSK AHGIDPNIRT GVRTTTTGGS ITYSTYGKFL  1300
         ADGGCSGGAY DIIICDECHS TDSTTILGIG TVLDQAETAG ARLVVLATAT  1350
         PPGSVTVPHP NIEEIGLSNN GEIPFYGKAI PIEAIKGGRH LIFCHSKKKC  1400
         DELAAKLTGL GLNAVAYYRG LDVSVIPPIG DVVVVATDAL MTGFTGDFDS  1450
         VIDCNTCVTQ TVDFSLDPTF TIETTIVPQD AVSRSQRRGR TGRGRSGIYR  1500
         FVTPGERPSG MFDSSVLCEC YDAGCAWYEL TPAETSVRLR AYLNTPGLPV  1550
         CQDHLEFWES VFTGLTHIDA HFLSQTKQAG INFPYLVAYQ ATVCARAQAP  1600
         PPSWDQMWKC LIRLKPTLHG PTPLLYRLGA VQNEVILTHP ITKYIMACMS  1650
         ADLEVVTSTW VLVGGVLAAL AAYCLTTGSV VIVGRIILSG KPAVVPDREV  1700
         LYQEFDEMEE CASQLPYIEQ GMQLAEQFKQ KALGLLQTAT KQAEAAAPVV  1750
         ESKWRALETF WAKHMWNFIS GIQYLAGLST LPGNPAIASL MAFTASITSP  1800
         LTTQNTLLFN ILGGWVAAQL APPSAASAFV GAGIAGAAVG SIGLGKVLVD  1850
         ILAGYGAGVA GALVAFKVMS GEVPSTEDLV NLLPAILSPG ALVVGVVCAA  1900
```

FIG. 7G

```
                10         20         30         40         50
         1234567890 1234567890 1234567890 1234567890 1234567890
         ILRRHVGPGE GAVQWMNRLI AFASRGNHVS PIHYVPESDA AARVIQILSS    1950
         LTTTQLLKRL HQWINEDCST PCSGSWLRDV WDWICIVLTD FKIWLQSKLL    2000
         PRLPGVPFLS CQRGYKGWWR GDGIMQTTCP CGAQIAGHVK NGSMRIVGPR    2050
         TCSNIWHGTF PINAYTTGPC TPSPAPNYSR ALWRVAAEEY VEVIRVGDFH    2100
         YVTGMTTDNV KCPCQVPAPE FFTEVDGVRL HRYAPACKPL LREDVTFQVG    2150
         LNQYLVGSQL PCEPEPDVTV LTSMLTDPSH ITAETAKRRL ARGSPPSLAS    2200
         SSASQLSAPS LKATCTTHHD SPDADLIEAN LLWRQEMGGN ITRVESENKV    2250
         VILDSFEPLH AEGDEREISV AAEILRKSRK FPSALPIWAR PDYNPPLLES    2300
         WKDPDYVPPV VHGCPLPPTK APPIPPPRRK RIVVLTESNV SSALAELATK    2350
         TFGSSGSSAV DSGIATALPD LASDDGDKGS DVESYSSMPP LEGEPGDPDL    2400
         SDGSWSTVSE EASEDVVCCS MSYTWTGALI TPCAAEESKL PINPLSNSLL    2450
         RHHNMVYATT SRSASLRQKK VTFDRLQVLD DHYRDVLKEM KAKASTVKAK    2500
         LLSIEEACKL TPPHSAKSKF GYGAKDVRNL SSRAVNHIRS VWEDLLEDTE    2550
         TPIDTTIMAK SEVFCVQPEK GGRKPARLIV FPDLGVRVCE KMALYDVVST    2600
         LPQAVMGSSY GFQYSPKQRV EFLVNIWKSK KCPMGFSYDT RCFDSTVTES    2650
         DIRVEESTYQ CCDLAPEARQ AIRSLTERLY IGGPLTNSKG QNCGYRRCRA    2700
         SGVLTTSCGN TLTCYLKATA ACRAAKLQDC TMLVNGDDLV VICESAGTQE    2750
         DAAALRAFTE AMTRYSAPPG DPPQPEYDLE LITSCSSNVS VAHDASGKRV    2800
         YYLTRDPTTP LARAAWETAR HTPINSWLGN IIMYAPTLWA RMILMTHFFS    2850
         ILLAQEQLEK ALDCQIYGAC YSIEPLDLPQ IIERLHGLSA FTLHSYSPGE    2900
         INRVASCLRK LGVPPLRTWR HRARSVRAKL LSQGGRAATC GRYLFNWAVR    2950
         TKLKLTPIPA ASQLDLSGWF VAGYSGGDIY HSLSRARPRW FPLCLLLLSV    3000
         GVGIYLLPNR                                                3010
```

FIG. 7H

INFECTIOUS CDNA CLONE OF GB VIRUS B AND USES THEREOF

This application is a 371 of international application PCT/US00/15293, filed Jun. 2, 2000, which claims benefit of provisional application 60/137,694, filed Jun. 4, 1999.

FIELD OF INVENTION

The present invention relates to nucleic acid sequence which comprises the genome of an infectious GB virus B (GBV-B) clone. The invention also relates to the use of the nucleic acid sequence of the infectious GB virus B clone to study indirectly the molecular properties of hepatitis C virus (HCV), and in the production of HCV/GBV-B chimeras. The invention further relates to the use of the infectious nucleic acid sequence of the GB virus B clone and the HCV/GBV-B chimeras in the development of vaccines and therapeutics for HCV.

BACKGROUND OF INVENTION

Transmission studies of potential human hepatitis agents were first reported in 1967 (Deinhardt 1967). Four tamarins inoculated with acute phase sera from a surgeon with acute hepatitis (patient GB) developed hepatitis, as did most tamarins inoculated in serial passage studies. Subsequent studies indicated that the etiological agent responsible for the development of hepatitis in these animals was not any of the known human hepatitis viruses (Purcell 1994). In 1995, two related RNA viruses named GB virus-B (GBV-B) and GB virus A (GBV-A) were identified in acute phase sera of a tamarin which developed hepatitis following inoculation with serum of the eleventh tamarin passage of the putative GB agent (Simons 1995a).

GBV-B infection of tamarins resulted in acute resolving hepatitis (Schlauder 1995, Buhk 1997). The natural host of GBV-B is still unknown as the virus has not been detected in uninoculated animals or in humans.

GBV-A, on the other hand, is an indigenous tamarin virus rather than a component of the original GB inoculum (Bukh 1997, Erker 1998). Experimental infection of tamarins with GBV-A did not produce hepatitis (Schlauder 1995). A human agent, GBV-C or hepatitis G virus, most closely related to GBV-A, was later identified (Simons 1995b, Linnen 1996). However, it is still not clear whether this virus actually causes hepatitis (Alter 1998, Bukh 1998a). Thus, of the known GB viruses, GBV-B may be the only true hepatitis virus.

Based on analysis of their genomic sequences, GBV-A, GBV-B and GBV-C were classified as members of the Flaviviridae family of viruses, and among the known viruses, GBV-B is the virus most closely related to hepatitis C virus (HCV) (Muerhoff 1995, Robertson 1998).

The GBV-B virus contains a positive-sense, single-stranded RNA genome of 9143 nucleotides (nts) (Simons 1995a, Muerhoff 1995). The viral genome of GBV-B consists of a 5' untranslated region (UTR), a single long open reading frame (ORF) and a 3' UTR. Based on known motifs, structural proteins were predicted to be encoded in the 5' portion of the ORF and nonstructural (NS) proteins in the 3' portion of the ORF (Muerhoff 1995). The hydropathy plots of the polyproteins of GBV-B and HCV are very similar even though the overall homology of the predicted polyproteins between GBV-B and HCV is only about 25–30% (Muerhoff 1995). The putative envelope proteins (E1 and E2) of GBV-B and HCV share common structural features, and significant homology was observed between the NS3 serine protease, the NS3 RNA helicase, and the NS5 RNA-dependent RNA polymerase regions of GBV-B and HCV (Muerhoff 1995). Furthermore, the function and substrate specificity of the GBV-B and HCV NS3 serine proteases are also similar (Scarselli 1997). The genomic structure and organization of GBV-B and HCV share additional features of interest. First, colinear regions with significant sequence homology were identified in the 5' UTRs (Muerhoff 1995) and the predicted IRES structure of GBV-B is similar to that of HCV (Lemon 1997). Second, both viruses begin the 3' UTR with a short sequence followed by a poly (U) stretch followed by additional nucleotides (50 nucleotides for GBV-B and 98 nucleotides for HCV). However, the 3' terminal sequence of HCV forms a stable stem-loop structure (Kolykhalov 1996) whereas the published 3' terminal sequence of GBV-B does not.

To date, molecular studies of HCV are severely limited by the lack of an efficient cell culture system for the virus and by expense and limited availability of chimpanzees, the sole animal model for HCV. Accordingly, a less expensive and more readily available animal than chimpanzees is necessary as an animal model for the study of HCV.

SUMMARY OF INVENTION

The present invention relates to nucleic acid sequence which comprises the genome of an infectious GB virus B (GBV-B) clone. It is therefore an object of the invention to provide nucleic acid sequence which encodes an infectious GBV-B. Such nucleic acid sequence is referred to throughout the application as “infectious nucleic acid sequence”.

As significant structural homology exists between the genomes of GBV-B and HCV, the invention also relates to the use of infection of tamarins with the infectious nucleic acid sequence of GBV-B or with mutants of the infectious sequence to study indirectly the molecular properties of hepatitis C virus (HCV) or as a preliminary screen to identify agents which have antiviral activity against HCV.

The invention further relates to “chimeric nucleic acid sequences” consisting of portions of the infectious nucleic acid sequence of GBV-B and portions of the nucleic acid sequences of other viruses closely related to GBV-B such as HCV, GBV-C or other members of the Flaviviridae family which do not replicate in tamarins. In a preferred embodiment, the chimeric nucleic acid sequences consist of portions of the infectious nucleic acid sequence of GBV-B and portions of the nucleic acid sequence of HCV. The nucleic acid sequences taken from GBV-B and HCV can be open-reading frame sequences, and/or sequences from the 5' UTR and/or 3' UTR.

In one embodiment, GBV-B/HCV chimeras may be made in which 5' or 3' UTR sequences of the GBV-B infectious clone are replaced with the corresponding sequence from an HCV clone.

In another embodiment, GBV-B/HCV chimeras may be constructed in which the structural or non-structural regions of GBV-B are replaced by corresponding regions of HCV. Thus, such a chimera would contain, for example, the HCV structual region in a GBV-B “genomic backbone”. Of course, it is understood by one of skill in the art that the construction of the above-described chimeric nucleic acid sequences may be reversed such that, for example, the GBV structural region may replace the structual region of an HCV genome to produce a chimera in which the GBV structural region is contained in an HCV backbone.

The invention further relates to the use of the chimeric nucleic acid sequences of the invention to study the functions of HCV genes, and for the development of vaccine and antiviral agents against HCV.

The invention also relates to the use of the infectious GBV-B nucleic acid sequence, the mutated GBV-B nucleic acid sequences or the chimeric sequences of the invention to identify cell lines capable of supporting the replication of GBV-B or the chimeras of the invention.

The present invention also relates to the polypeptides encoded by the nucleic acid sequences of the invention or fragments thereof.

The present invention further relates to the in vitro and in vivo production of GBV-B, mutant GBV-B viruses or chimeric GBV-B/HCV viruses from the nucleic acid sequences of the invention.

The invention also provides that the nucleic acid sequences and viruses of the invention be supplied in the form of a kit, alone or in the form of a pharmaceutical composition.

BRIEF DESCRIPTION OF FIGURES

FIGS. 6A–6F show the nucleotide sequence (SEQ ID NO: 6) of the infectious hepatitis C virus clone of genotype 1a strain H77C and FIGS. 6G–6H show the amino acid sequence (SEQ ID NO: 7) encoded by the clone.

FIGS. 7A–7F show the nucleotide sequence (SEQ ID NO: 8) of the infectious hepatitis C virus clone of genotype 1b strain HC-J4 and FIGS. 7G–H show the amino acid sequence SEQ ID NO: 9) encoded by the clone.

DESCRIPTION OF THE INVENTION

Figure 1:
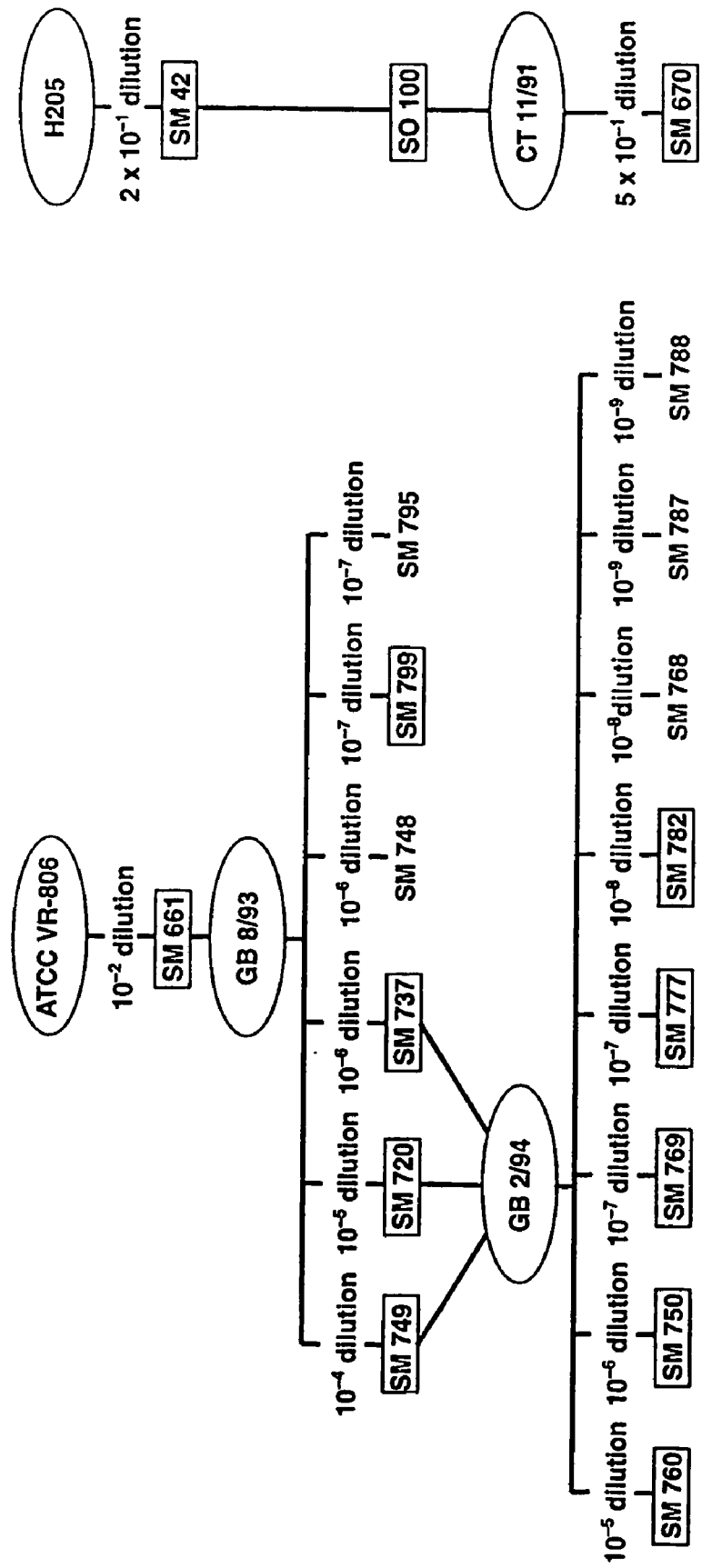
FIG. 1 shows a flow diagram of GB virus transmission studies in two species of tamarins, *Saguinus mystax* (SM) and *Saguinus oedipus* (SO). The animals infected with GBV-B (Simons 1995a) are boxed. Two serum pools (GB 8/93 and GB 2/94) were made from acutely infected animals. Both pools contained GBV-B, as well as GBV-A (Simons 1995) at a titer of $10^8$ genome equivalent (GE)/ml. A 10% liver homogenate (CT 11/91) was made from a sacrificed tamarin. A number of *S. mystax* tamarins (SM 737, 749, 750, 760, 782, 795 and 799) and *S. oedipus* tamarins (SO 100) were naturally infected with GBV-$A_{SM}$ and GBV-$A_{SO}$, respectively, prior to inoculation (Bukh 1997). Only two tamarins (SM 720 and 748), both GBV-$A_{SM}$ negative, became infected with GBV-A (Simons 1995) following inoculation. Tamarins SM42 and SM670 were not tested for GBV-A or GBV-$A_{SM}$.

The present invention relates to nucleic acid sequence which comprises the genome of an infectious GB virus B (GBV-B) clone. The nucleic acid sequence which comprises the genome of an infectious GBV-B virus is shown in SEQ ID NO:1 and is contained in the plasmid construct PGBB deposited with the American Type Culture Collection (ATCC) on May 28, 1999 and having ATCC accession number PTA-152. The present invention relates to the identification of a 260 nucleotide sequence at the 3' end of the infectious GBV-B clone which is shown in Example 3 to be necessary for the development of the infectious clone.

Since GBV-B is the virus most closely related to HCV, the present invention also relates to experimental infection of tamarins with the infectious GBV-B clone of the invention or with mutants of the infectious GBV clone to study indirectly the molecular properties of HCV or as a preliminary screen to identify agents which have antiviral activity against HCV. For example, since the predicted internal ribosome entry site (IRES) structure in the 5' UTR of GBV-B is similar to that of HCV (Lemon 1997), the NS3 serine proteases of GBV-B and HCV have been shown to share substrate specificity in vitro (Scarselli 1997), and the 3' UTRs of HCV (Yanagi 1999) and GBV-B (see Examples) have been shown to be critical for viral infectivity, mutagenesis of these regions in the GBV-B infectious clone may be undertaken to examine IRES function, NS3 serine protease activity or the role of the 3' UTR in viral infectivity in vivo. Where such "mutations" are introduced into the GBV-B clone of the invention to create a "mutated" GBV-B sequence, the mutations include, but are not limited to, point mutations, deletions and insertions. Of course, one of ordinary skill in the art would recognize that the size of the insertions would be limited by the ability of the resultant nucleic acid sequence to be properly packaged within the virion. Such mutations could be produced by techniques known to those of skill in the art such as site-directed mutagenesis, fusion PCR, and restriction digestion followed by religation.

Alternatively, given the significant structural homology that exists between the genomes of GBV and HCV, the infectious GBV-B clone may be used to screen for inhibitors of IRES function or viral enzyme activity (for example, NS3 helicase, NS3 protease, NS2-NS3 protease or NS5B RNA polymerase activity). Such inhibitors may be useful as antiviral agents to HCV since viral enzyme activity and IRES function are known to be critical for HCV replication.

The effect of such inhibitors on the IRES function or viral activity of the GBV-B encoded by the infectious sequence of the invention may be measured by assays known to those of skill in the art to measure directly or indirectly viral replication or viral pathogenicity. Such assays include, but are not limited to, the measurement of virus titer in serum or liver of an infected tamarin by PCR or the measurement of GBV-B viral protein expression in liver cells of an infected tamarin by immunoflourescence or Western blot. Of course, it is understood that a comparison of results obtained for control tamarins (treated only with infectious nucleic acid sequence) with those obtained for treated tamarins (nucleic acid sequence and antiviral agent) would indicate, the degree, if any, of antiviral activity of the candidate antiviral agent. Of course, one of ordinary skill in the art would readily understand that the tamarins can be treated with the candidate antiviral agent either before or after exposure to the infectious nucleic acid sequence of the present invention.

In yet another embodiment, the invention relates to "chimeric nucleic acid sequences" which consist of portions of the infectious nucleic acid sequence of GBV-B and portions of nucleic acid sequences of viruses which are related to GBV-B such as HCV, GBV-C and other members of the Flaviviridae family which do not infect tamarins. In a preferred embodiment, chimeric nucleic acid sequences consist of portions of the infectious nucleic acid sequence of GBV-B and portions of nucleic acid sequences of hepatitis C viruses (HCV) of various genotypes or subtypes; preferably portions of nucleic acid sequence of infectious HCV clones of genotypes 1a (ATCC accession number PTA-157; FIGS. 6A–6F), 1b (ATCC accession number 209596; FIGS. 7A–7F) or 2a (ATCC accession number PTA-153; SEQ ID NO: 4). The nucleic acid sequences taken from GBV-B and HCV can be open-reading frame sequences, and/or sequences from the 5' UTR and/or 3' UTR. The gene borders of the HCV genome, including nucleotide and amino acid locations, have been determined, for example, as depicted in Houghton, M. (1996), and the putative gene borders of the GBV-B are shown in Table 1.

Of course, it is understood that the production of GBV-B/HCV chimeras could include insertion of specific genes or regions of the infectious GBV-B clone into an HCV "genomic backbone" (where the HCV genomic backbone is preferably an infectious nucleic acid sequence of HCV genotypes 1a, 1b or 2a described above) or alternatively, could include insertion of specific genes (or portions thereof) or regions of an HCV genome into the GBV-B infectious clone of the invention. Of course, where HCV genes or regions are to be inserted into the GBV-B infectious clone, it is to be understood that the inserted HCV sequences may be unmodified or may be mutated in order to examine the effect of the mutation(s) on the function of the inserted HCV gene or region in the chimeric GBV-B-HCV virus.

Such chimeras can readily be produced by methods known to those of ordinary skill in the art.

In one embodiment, GBV-B/HCV chimeras may be made in which 5' or 3' UTR sequences of the GBV-B infectious clone are replaced with the corresponding sequence from an HCV clone. For example, chimeras may be constructed in which the IRES sequence of the infectious GBV-B clone is replaced by the IRES sequence of HCV. Such chimeras can be used in identifying inhibitors of IRES activity which would be useful as antiviral agents, or could be used to examine HCV IRES function in vivo. Alternatively, mutations could be introduced into the HCV IRES contained in the GBV-B clone in order to examine the effect of the mutation(s) on IRES function in vivo.

Alternatively, GBV-B/HCV chimeras may be made in which the 3' UTR sequence of GBV-B is replaced by the 3' UTR sequence of HCV. As the 3' terminal stem-loop structure is believed to be important for initiation of RNA replication and has been shown to be critical for infectivity of HCV in vivo, such chimeras may be used for more detailed analysis of the function of the 3' UTR sequence of HCV in vivo and for the testing of candidate antiviral agents.

In another embodiment, GBV-B/HCV chimeras may be constructed in which the structural or non-structural regions of GBV-B are replaced by corresponding regions of HCV. Such chimeras would be useful in identifying whether the inability of HCV to infect tamarins is due to the inability of HCV's structural region to bind the receptor necessary for infection of tamarins or to the absence of sequences in HCV's nonstructural regions which are necessary for replication in tamarins. For example, the ability to infect tamarins with GBV-B/HCV chimeras in which the non-structural region of GBV-B is replaced by the non-structural region of HCV would indicate that the structural genes of GBV-B are necessary for viral infection in tamarins, and that the inability of HCV to infect tamarins is likely due to its lack of receptors for HCV.

Alternatively, the ability to infect tamarins with GBV-B/HCV chimeras in which the structural region of GBV-B is replaced by the structural region of HCV would indicate that the non-structural genes of GBV-B are critical for viral infection in tamarins, and that the inability of HCV to infect tamarins is likely due to HCV's lack of nonstructural sequences which are necessary for replication in tamarins.

Of course, GBV-B-HCV chimeras may be constructed in which only a portion of the non-structural or structural regions of GBV-B are replaced by the corresponding portions of HCV sequences. For example, a chimera in which only one or two of the three structural genes (C, E1 and E2) of GBV-B are replaced by the corresponding HCV structural genes may be made. In one embodiment, nucleic acid sequences comprising the E1 and E2 genes of GBV-B may be replaced by the sequences comprising the HCV E1 and E2 genes. In another embodiment, nucleic acid sequence comprising either the E1 or E2 gene of GBV-B is replaced by sequence encoding either the HCV E1 or E2 gene.

Alternatively, only a fragment of a GBV-B structural gene in the infectious GBV clone may be replaced with the corresponding HCV gene fragments. For example, the amino terminal of the GBV-B E1 gene may be replaced by the corresponding portion of an HCV E1 gene or an amino terminal portion of the GBV-B E2 gene may be replaced by an amino terminal portion of HCV E2 gene tht containing the HVR1 region. As the structural genes of HCV are believed to be important for neutralization, chimeras containing an HCV structural gene(s) or fragment(s) thereof can be used to develop vaccines against HCV.

In yet another embodiment, chimeras in which individual non-structural genes of GBV-B, such as NS3 RNA helicase, NS3 protease, or the NS5B RNA-dependent RNA polymerase are replaced by the corresponding non-structural genes of HCV may be constructed. Such chimeras would, for example, be useful in identifying inhibitors of viral enzyme activity which would be useful as antiviral agents. Of course, it is understood that in order to construct chimeras in which the polyprotein cleavage sites of the GBV-B remain intact, it may be desirable to replace only a fragment of a nonstructural gene of GBV-B with the corresponding HCV gene fragment.

The present invention also relates to polypeptides encoded by the nucleic acid sequences of the invention or fragments thereof. In one embodiment, said polypeptide or polypeptides may be fully or partially purified from viruses produced by cells transfected with the nucleic acid sequences of the invention. In another embodiment, the polypeptide or polypeptides may be produced recombinantly from a fragment of the nucleic acid sequences of the invention. In yet another embodiment, the polypeptides may be chemically synthesized.

The present invention further relates to the in vitro and in vivo production of GBV-B, mutated GBV-B or chimeric GBV-B/HCV viruses from the nucleic acid sequences of the invention.

In one embodiment, the sequences of the invention can be inserted into an expression vector that functions in eukaryotic cells. Eukaryotic expression vectors suitable for producing high efficiency gene transfer in vivo are well known to those of ordinary skill in the art and include, but are not limited to, plasmids, vaccinia viruses, retroviruses, adenoviruses and adeno-associated viruses.

In another embodiment, the sequences contained in the recombinant expression vector can be transcribed in vitro by methods known to those of ordinary skill in the art in order to produce RNA transcripts which encode the GBV-B of the invention. The GBV-B of the invention may then be produced by transfecting cells by methods known to those of ordinary skill in the art with either the in vitro transcription mixture containing the RNA transcripts or with the recombinant expression vectors containing the nucleic acid sequences described herein.

In assaying the ability of the mutated GBV-B sequences or of the chimeric sequences of the invention to infect tamarins, the virulence phenotype of the virus produced by transfection of tamarins with the sequences of the invention can be monitored by methods known in the art such as measurement of liver enzyme levels (alanine aminotransferase (ALT) or isocitrate dehydrogenase (ICD)) or by histopathology of liver biopsies.

The present invention also relates to the use of the infectious GBV-B sequence, the mutated GBV-B nucleic acid sequences or the chimeric sequences of the invention to identify cell lines capable of supporting the replication of GBV-B or the chimeras of the invention.

Transfection of tissue culture cells with the nucleic acid sequences of the invention may be done by methods of transfection known in the art such as electroporation, precipitation with DEAE-Dextran or calcium phosphate, or incorporation into liposomes.

In one such embodiment, the method comprises the growing of animal cells in vitro and transfecting the cells with the nucleic acid of the invention, then determining if the cells show indicia of GBV-B or HCV infection. Such indicia include the detection of viral antigens in the cell, for example, by immunofluorescence procedures well known in the art; the detection of viral polypeptides by Western blotting using antibodies specific therefor; and the detection of newly transcribed viral RNA within the cells via methods such as RT-PCR. The presence of live, infectious virus particles following such tests may also be shown by injection of cell culture medium or cell lysates into healthy, susceptible animals, with subsequent exhibition of the signs and symptoms of GBV-B infection.

Suitable cells or cell lines for culturing GBV-B or the chimeric GBV-B-HCV include, but are not limited to, lymphocyte and hepatocyte cell lines known in the art.

Alternatively, primary hepatocytes can be cultured, and then infected; or, the hepatocyte cultures could be derived from the livers of infected tamarins. In addition, various immortalization methods known to those of ordinary skill in the art can be used to obtain cell-lines derived from hepatocyte cultures. For example, primary hepatocyte cultures may be fused to a variety of cells to maintain stability.

The invention also provides that the nucleic acid sequences and viruses of the invention be supplied in the form of a kit, alone or in the form of a pharmaceutical composition.

All scientific publication and/or patents cited herein are specifically incorporated by reference. The following examples illustrate various aspects of the invention but are in no way intended to limit the scope thereof.

EXAMPLES

Materials and Methods

Source of GB Virus B

Two tamarin pools VR-806, (American Type Culture Collection) and H205, were used for experimental transmission of the GB virus agents to tamarins species *Saguinus mystax* and *Saguinus oedipus*.

Amplification, Cloning and Sequence Analysis of GBV-B

Viral RNA was extracted from aliquots of the GB 2/94 serum pool or CT 11/91 liver homogenate with the TRIzol system (GIBCO/BRL). Primers used in cDNA synthesis and PCR amplification were based on the genomic sequence of GBV-B published by Simons et al (Simons 1995) shown in SEQ ID NO:3. Long RT-PCR was performed using Superscript II reverse transcriptase (GIBCO/BRL) and the Advantage cDNA polymerase mix (Clontech) as described previously (Tellier 1996). Four subgenomic regions of GBV-B covering the entire published sequence (Simons 1995) were amplified from serum and the PCR products were purified and cloned into pGEM-9Zf(−) (Promega) or pCR2.1 vector (Invitrogen) using standard procedures.

The 5' terminus of GBV-B was amplified from serum by using the rapid amplification of cDNA ends (RACE) with dC or dA tailing (GIBCO/BRL) and GBV-B specific antisense primers. Two different approaches were used to determine the 3' terminal sequence of GBV-B. In one approach, GBV-B RNA extracted from serum was circularized with T4 RNA ligase (Promega) and the 5'-to-3'-end-ligated viral RNA was amplified in RT-PCR using specific GBV-B primers. In the second approach, the 5' end of the negative strand GBV-B RNA extracted from the liver homogenate was amplified using the 5' RACE with dC tailing and GBV-B specific sense primers. The PCR products were cloned directly into pCR2.1-TOPO by using the TOPO TA Cloning Kit (Invitrogen).

The consensus sequence of GBV-B was determined by direct sequencing of PCR products (nucleotides 1–9078 and nucleotides 9130–9359) and by sequence analysis of the clones (nucleotides 1–7135 and nucleotides 7151–9399). Nucleotide positions correspond to those of the infectious clone (pGBB). Analyses of genomic sequences were performed with GeneWorks (Oxford Molecular Group) (Bukh 1995). To determine whether the GenBank data base contained sequences with homology to the GBV-B 3' UTR sequence identified in the present invention, a "Blast" search was performed. The predicted secondary structure of the GBV-B and HCV 3' UTR sequences were determined by the program "mfold" (Genetics Computer Group).

Construction of Consensus cDNA Clones of GBV-B

First, clone pGBB5-1, a consensus clone of GBV-B 2/94 containing the 3' terminus of GBV-B as published by Simons et al was constructed (Simons 1995a). The core sequence of the T7 promoter, a 5' guanosine residue and the sequence of GBV-B (9139 nucleotides) were cloned into pGEM-9Zf(−) vector using NotI/SacI sites. A BamHI site was included at the GBV-B 3' terminus. Digested fragments containing the consensus sequence were purified from subclones and ligated using convenient sites. Next, a second consensus clone of GBV-B, clone PGBB, was constructed by inserting the additional 3' terminal sequence, amplified by PCR from one of the clones obtained by the RACE procedure described above, into pGBB5-1 using XmaI (at position 9114) and BamHI sites. A XhoI site was inserted following the GBV-B 3' terminus. DH5-alpha competent cells (GIBCO BRL) were transformed and selected on LB agar plates containing 100 μg/ml ampicillin (SIGMA) and amplified in LB liquid cultures at 30° C. for 18–20 hrs (Yanagi 1997). Each cDNA clone was re-transformed to select a single clone, and large-scale preparation of plasmid DNA was performed with a QIAGEN plasmid Maxi kit as described previously (Yanagi 1997). Each clone was genetically stable since the digestion pattern was as expected following retransformation and the complete sequence was the expected one.

Intrahepatic Transfection of Tamarins with Transcribed GBV-B RNA

In 100 μl reactions, RNA was transcribed in vitro with T7 RNA polymerase (Promega) from 10 μg of linearized template plasmid. The plasmid pGBB5-1 was linearized with BamHI (Promega) and the plasmid PGBB was linearized with XhoI (Promega). The integrity of the RNA was checked by electrophoresis through agarose gel stained with ethidium bromide. Each transcription mixture was diluted with 400 μl of ice-cold phosphate-buffered saline without calcium or magnesium (SIGMA) and then immediately frozen on dry ice and stored at −80° C. Within 24 hours of synthesis, two transcription mixtures were injected into each tamarin by percutaneous intrahepatic injection guided by ultrasound (Emerson, 1992; Yanagi 1998, 1999). If the tamarin did not become infected, the same transfection was repeated once. All transfected animals were negative for GBV-A$_{SM}$ as determined by the protocol described previously (Bukh 1997a).

Monitoring of Experimental Course in Tamarins

Serum samples were collected weekly from the tamarins and monitored for liver enzyme levels [alanine aminotransferase (ALT), gamma-glutamyltranspeptidase (GGT), and isocitrate dehydrogenase (ICD)] by standard methods and for GBV-B RNA by a specific reverse transcriptase-polymerase chain reaction (RT-PCR) assay. Total RNA was extracted from 100 μl of serum using the TRIzol reagent. The RNA pellet was resuspended in 10 mM dithiothreitol (DTT) containing 5% (vol/vol) of RNasin (20–40 u/μl) (Promega). The RT-nested PCR was performed with primers from the 5' UTR of GBV-B (external primer pair: 5'-CCT AGC AGG GCG TOG GGG ATT TCC-3' (SEQ ID NO: 10) and 5'-AGG TCT GCG TCC TTG GTA GTG ACC-3' (SEQ ID NO: 11); internal primer pair: 5'-GGA TTT CCC CTG CCC GTC TG-3' (SEQ ID NO: 12) and 5'-CCC CGG TCT TCC CTA CAG TG-3' (SEQ ID NO: 13)). The reverse transcription was performed with avian myeloblastosis virus reverse transcriptase (Promega) and the external anti-sense primer and nested PCR was performed with AmpliTaq DNA polymerase or AmpliTaq Gold DNA polymerase (Perkin Elmer) as described previously (Bukh 1998a). Specificity was confirmed by sequence analysis of selected DNA products. Each set of experiments included a positive control sample (a $10^{-6}$ dilution of GB 8/93, estimated titer 100 genome equivalent (GE)) and appropriate negative control samples. The genome equivalent (GE) titer of GBV-B in positive samples was determined by RT-nested PCR on 10-fold serial dilutions of the extracted RNA (Bukh 1998a). One GE was defined as the number of GBV-B genomes present in the highest dilution positive in RT-nested PCR. The sensitivity of this RT-nested PCR assay for GBV-B was equivalent to that of our RT-nested PCR assay for HCV (Bukh 1998b), for example, conserved NS3 primers which had the same sensitivity for GBV-B as the 5' UTR primers could detect HCV at optimal sensitivity in samples with known HCV genome titer. Testing for GBV-A and GBV-A variants was performed by RT-nested PCR assays as described previously (Bukh 1997a).

The consensus sequence of the complete ORF was determined by direct sequencing of overlapping PCR products obtained by long RT-nested PCR on serum from one of the tamarins infected with RNA transcripts as previously described (Yanagi 1997).

Example 1

Transmission of GB Agent in Tamarins

To generate virus pools of the GB agent, tamarins were inoculated intravenously with pooled sera of the eleventh tamarin passage of this agent (FIG. 1). Acute phase sera from a *S. mystax* tamarin which developed hepatitis were pooled (GB 8/93) and inoculated into additional *S. mystax* tamarins to generate a second pool of acute phase serum (GB 2/94). Both serum pools contained approximately $10^8$ GE/ml of GBV-B and GBV-A. A 10% liver homogenate (CT 11/91) was prepared from a *S. oedipus* tamarin which developed hepatitis following inoculation with the twelfth passage of the GB agent. The titer of GBV-B in the liver homogenate was approximately $10^7$ GE/ml. The GB 2/94 serum and CT 11/91 liver samples were used as GBV-B cloning sources in the present study.

Figure 2:
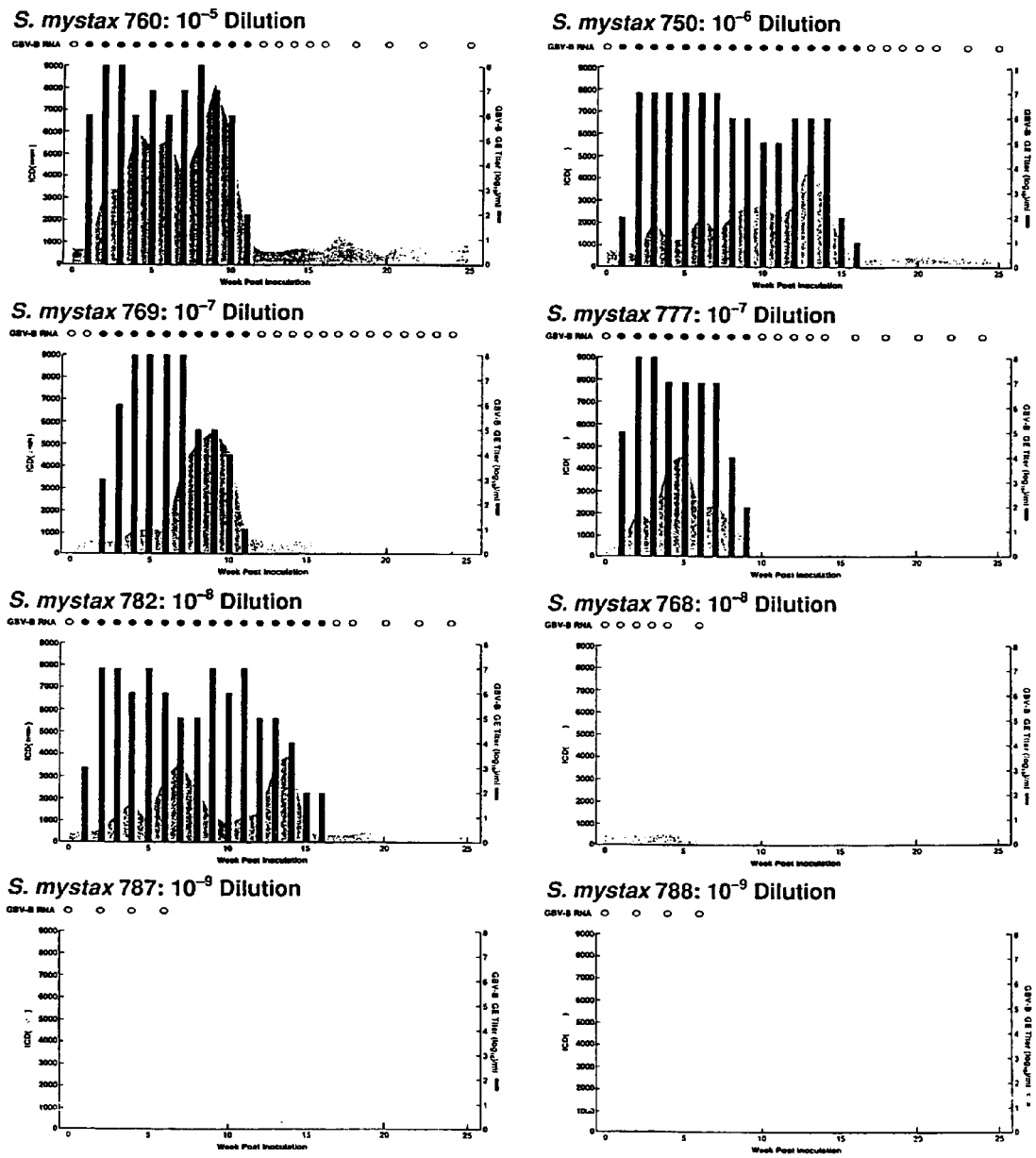
FIG. 2 shows the course of GBV-B infection in tamarins (*S. mystax*) inoculated with a dilution series of the GB 2/94 pool. All animals were inoculated intravenously at week 0 with 1 ml of the indicated dilution. Results of qualitative RT-nested PCR for GBV-B in serum are shown at the top (filled circles, positive; empty circles, negative). Serum levels of isocitrate dehydrogenase (ICD in units/ml); shaded area) and the estimated $\log_{10}$ GBV-B GE titer (vertical columns) were plotted against time.

Inoculation of eight *S. mystax* tamarins with ten-fold serial dilutions of the GB 2/94 pool demonstrated that its infectivity titer of GBV-B was $10^8$ tamarin 50% infectious doses (TID$_{50}$) (FIG. 2). The five GBV-B infected tamarins all developed acute resolving hepatitis characterized by early appearance of viremia (weeks 1 or 2 p.i.), peak viral titers of $10^7$–$10^8$ GE/ml and clearance of viremia after 9–16 weeks (FIG. 2). Two of these tamarins (*S. mystax* 769 and 777) were infected only with GBV-B and were negative for GBV-A and GBV-A$_{SM}$, whereas the other three tamarins were infected with both GBV-B and GBV-A$_{SM}$. A *S. mystax* tamarin inoculated with the liver homogenate also developed acute resolving hepatitis with peak GBV-B titers of $10^7$ GE/ml and clearance of viremia after 11 weeks. Likewise, four *S. mystax* tamarins inoculated with dilutions of the GB 8/93 pool developed acute resolving hepatitis with clearance of the GBV-B virus after 11–26 weeks. Thus, GBV-B infection in *S. mystax* tamarins is characterized by acute hepatitis, early appearance of viremia, high peak viral titers and viral clearance.

Example 2

Novel 3' Terminal Sequence of GBV-B

The consensus sequence of the complete 5' UTR of GBV-B (nucleotides 1–445) was deduced from 13 clones containing nucleotides 1–283 and 3 clones containing nucleotides 31–445. In addition, the entire 5' UTR sequence was determined by direct sequencing of the amplicons. The sequences of the various clones were highly conserved and the consensus 5' UTR sequence of GBV-B from this pool was identical to that of the previously published sequence for GBV-B (Simons 1995a). It is noteworthy that 13 of 15 clones analyzed from the rapid amplification of cDNA ends (RACE) procedure contained the published GBV-B 5' terminus (A residue) and that the same 5' terminus was obtained whether the 5' RACE was performed with dC or dA tailing.

The consensus sequence of the ORF (nucleotides 446–9037) was determined by direct sequencing of PCR products obtained using long RT-PCR (Yanagi 1997). In addition, 3 clones containing nts. 446–7135 (one of these clones had a deletion of nts. 3036–3636), 2 clones containing nts. 2019–3373, 5 clones containing nts. 7151–8261 and 7 clones containing nts. 7521–9037 were analyzed. The sequences of GBV-B clones in this pool were very homogeneous. Evidence of micro-heterogeneity was found at only 70 (0.8%) nucleotide and 36 (1.3%) amino acid positions, scattered throughout the ORF. The proportion of amino acid positions with heterogeneity ranged from 0.5–3.2% in different putative gene regions (lowest in NS3 and NS5B; highest in E2 and NS2). The GBV-B ORF sequence differed from the published sequence of GBV-B (Simons 1995) at 34 (0.4%) nucleotide and 12 (0.4%) deduced amino acid positions, respectively (Table 1).

TABLE 1

Nucleotide and amino acid differences among GBV-B (Simons 1995a), the consensus sequence of GBV-B recovered from a virus pool used as the cloning source (GBV-B, 2/94) and the infectious clone of GBV-B (pGBB).

| Genomic Region* | Position nt [aa] | Nucleotide GBV-B | | | Amino Acid GBV-B | | |
| --- | --- | --- | --- | --- | --- | --- | --- |
| | | GBV-B | 2/94 | pGBB | GBV-B | 2/94 | PGBB |
| 5' UTR (1–445) | | | | | | | |
| C (446–913) | | | | | | | |
| E1 (914–1489) | 1030 | C | T | T | | | |
| E2 (1490–2641) | 1498 | T | C (t) | C | | | |
| | 1628 [395] | G | A (g) | A | V | I (V) | I |
| | 2552 [703] | G | A (g) | A | D | N (D) | N |
| | 2562, 2563 [706] | C, A | A, C | A, C | P | H | H |
| | 2566 | T | C | C | | | |
| | 2625 [727] | C | T | T | A | V | V |
| NS2 (2642–3385) | 2647 | C | T (c) | T | | | |
| | 2816 [791] | C | T | T | L | F | F |
| | 2855 [804] | A | G | G | T | A | A |
| | 3235 | A | G | G | | | |
| NS3 (3386–5125) | 3475** | C | C (t) | T | | | |
| | 3760 | C | T (c) | T | | | |
| | 4114 | C | T | T | | | |
| | 4117 | C | A | A | | | |
| | 4177 | T | C | c | | | |
| | 4615 | C | T | T | | | |
| NS4A (5126–5290) | | | | | | | |
| NS4B (5291–6034) | 5329 | C | T | T | | | |
| | 5332 | T | C | C | | | |
| | 5350 | A | C | C | | | |
| | 5455 | C | T (c) | T | | | |
| NS5A (6035–7267) | 6413 [1990] | T | A (t) | A | L | M (L) | M |
| | 6577 | G | T | T | | | |
| | 6690 [2082] | T | C (t) | C | I | T (I) | T |
| | 6965 [2174] | T | C (t) | C | S | P (S) | P |
| | 7015 | A | G (a) | G | | | |
| | 7128 [2228] | G | A | A | G | E | E |
| | 7138 | A | A | G | | | |
| | 7142 [2233] | A | G | G | T | A | A |
| NS5B (7268–9037) | 7282 | T | C (t) | c | | | |
| | 7849 | C | A | A | | | |
| | 7852 | C | T | T | | | |
| | 8942 [2981] | G | A (g) | A | V | I (V) | I |
| | 8971 | T | C | C | | | |
| | 9026 | C | T (c) | T | | | |
| 3' UTR (9038–9399) | 9061 | T | C | C | | | |
| | Poly(U) | 27 nts | 11–23 nts | 23 nts | | | |
| | 9134 | Deletion | C | C | | | |
| | 9141–9399 | ND | 259 nts | 259 nts | | | |

*Nucleotide positions corresponding to pGBB. Putative gene borders defined as suggested by homology with HCV (Muerhoff 1995). No homology was observed at the NS2-NS3 junction.
**Positions that differ between the cloning source (GBV-B 2/94) and the infectious clone of GBV-B (pGBB). The change introduced into pGBB at position 7138 introduced an artificial SalI site. nd: Not determined. Nucleotides and amino acids shown in parenthesis were found as a minor species in the cloning source (GBV-B, 2/94)

Figure 3:
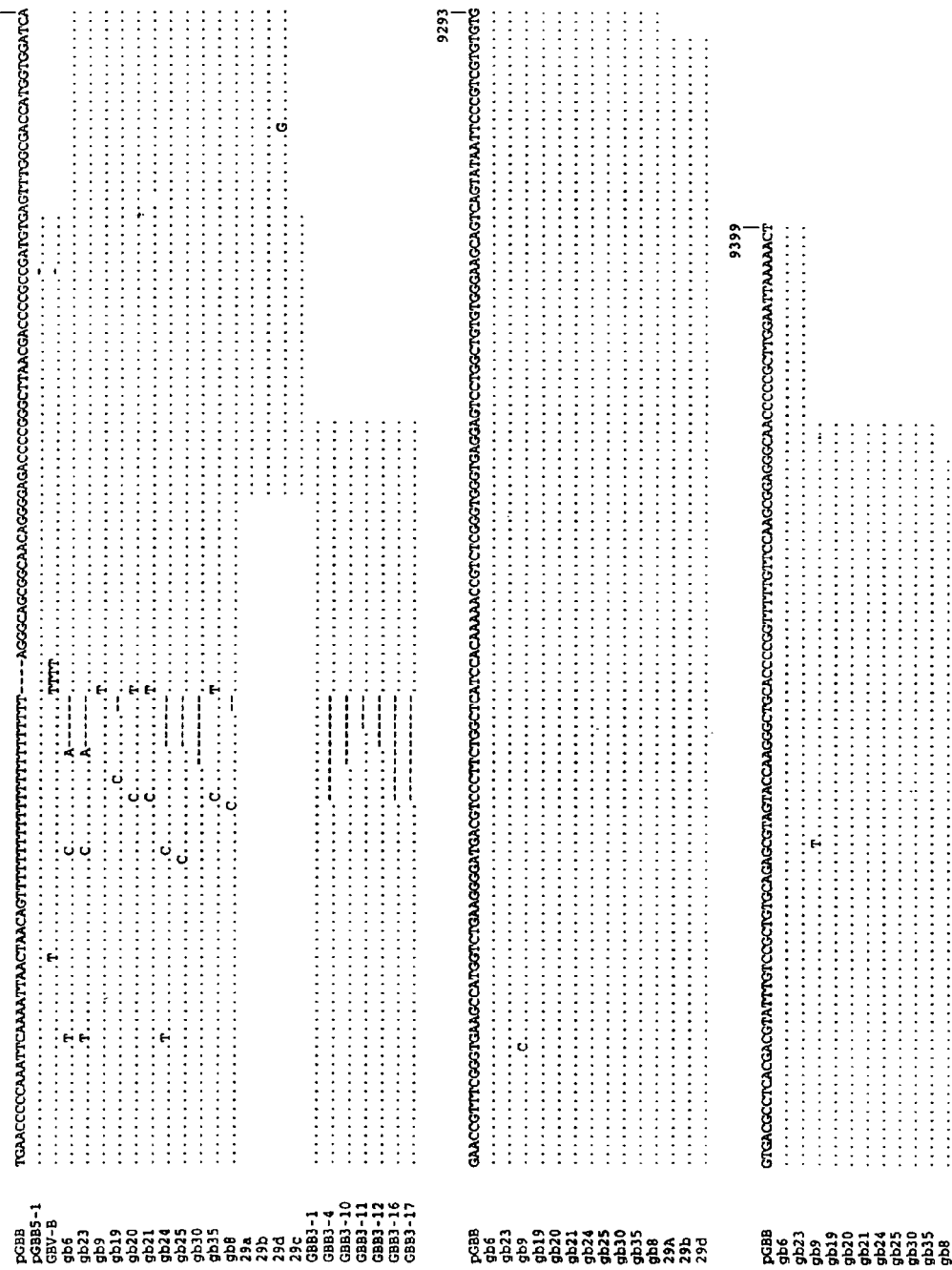
FIG. 3 shows alignment of the 3' UTR sequences of GBV-B. The sequence of the infectious clone of GBV-B (PGBB) is shown at the top (nts. 9038–9399 of SEQ ID NO: 1). The other sequences shown are: pGBB5-1, a non-infectious clone of GBV-B; GBV-B, a prototype of GBV-B (Simons 1995); eleven "gb" clones obtained from CT 11/91 liver homogenate by 5' RACE on the minus-strand GBV-B RNA; four "29" clones obtained from GB 2/94 pool by RT-PCR across 5'-to-3'-end-ligated viral GBV-B RNA; and seven "GBB3" clones obtained from GB 2/94 pool by standard RT-PCR. With pGBB as the reference, nucleotide substitutions or insertions are shown as uppercase letters, identical nucleotides are shown as dots and nucleotide deletions are shown as dashes.
Figure 4:
FIG. 4 shows the predicted secondary structure of the 3' UTRs of GBV-B (nts. 9038–9399 of SEQ ID NO: 1) and HCV (nts. 9363–9599 of SEQ ID NO: 6) as determined by the program "mfold" (Genetics Computer Group).
Figure 4:
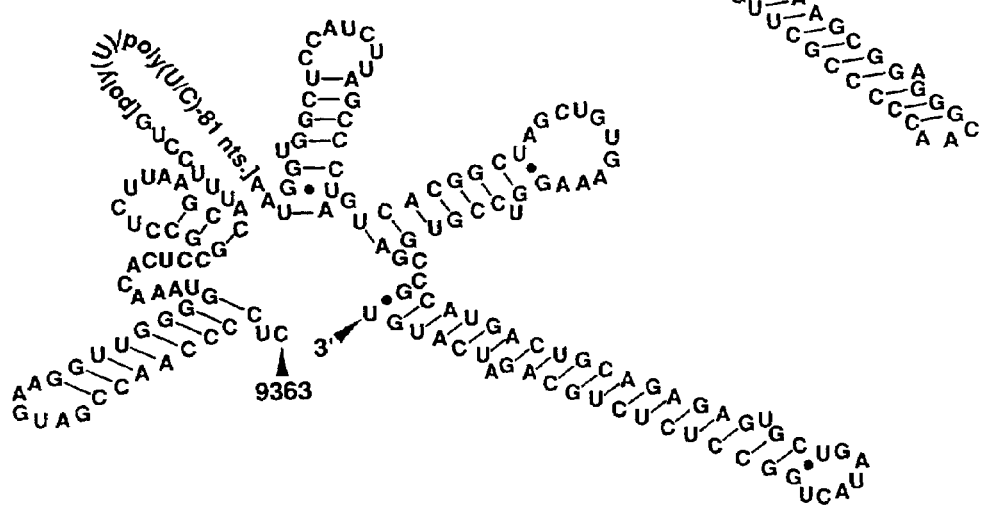

The sequence for the 3' UTR is shown in FIG. 3. Additional 3' UTR sequence was initially identified by performing RT-PCR across 5'-to-3'-end-ligated viral RNA extracted from serum. In all 4 clones with GBV-B sequences, the 5' UTR was truncated compared to the published sequence (simon 1995a). However, whereas one clone (29c) had the exact 3' terminus previously published by Simons et al. (Simons 1995a), the three other clones (29a, 29b, 29d) had 150 additional terminal nucleotides. Compared with the published sequence, all four clones had a single nucleotide insertion (C residue) at position 9134. Next, RACE using dC-tailing only was performed on the 5' end of the negative-strand RNA extracted from the liver homogenate. All 11 clones analyzed had additional sequences at the 3' terminus. Compared with the published GBV-B sequence, two clones (gb6, gb23) had 259 additional nucleotides, 8 clones (gb9, gb19, gb20, gb21, gb24, gb25, gb30, gb35) had 236 additional nucleotides and 1 clone (gb8) had 232 additional nucleotides. Moreover, all of these clones had the insertion at position 9134. The 3' UTR sequences among the various clones were highly conserved (FIG. 3). To demonstrate that the terminal 22 nucleotides found only in clones gb6 and gb23 existed in circulating viruses, RT-nested PCR was performed on 10-fold serially diluted RNA extracted from the serum pool GB 2/94 using an RT and external antisense primer deduced from this sequence. GBV-B RNA was detected at a dilution of $10^{-7}$ and the sequence of the amplicon was identical to the sequence recovered from the liver homogenate. Thus, the 3' UTR of GBV-B consists of a short sequence of 30 nucleotides followed by a 11–24 nucleotide-long poly (U) tract (single C residues were observed in GBV-B from the liver homogenate) and a 3' terminal sequence of at least 309 nucleotides. The new GBV-B 3' UTR sequence did not have significant homology to any of the sequences deposited in the GenBank database. A prediction of the secondary structure of the 3' UTR sequence is shown in FIG. 4. The most notable feature of the secondary structure is a highly stable stem-loop structure at the very 3' end consisting of 47 nucleotides.

Example 3

The pGBB Clone of GBV-B is Infectious In Vivo

The infectivity of RNA transcripts from the consensus clone pGBB5-1 which encompassed only the published GBV-B sequence (Simons 1995) was first tested. Within the GBV-B sequence there were no deduced amino acid differences and only 2 nucleotide differences (at nucleotide positions 3475 and 7138) between the consensus sequence of the cloning source (GBV-B 2/94) and the sequence of pGBB5-1 clone. In addition, the 3' UTR of pGBB5-1 had a deletion at nucleotide position 9134 and was missing the 3' terminal 259 nucleotides (FIG. 3). Prior to transcription, the pGBB5-1 clone was linearized at the BamHI site with digestion at the exact GBV-B 3' terminus. The RNA transcripts from pGGB5-1 were injected into the liver of two tamarins (S. mystax 797 and 815). GBV-B RNA was not detected in weekly serum samples collected during 17 weeks of follow-up. As the susceptibility of these two tamarins to GBV-B was subsequently demonstrated by experimental infection using a GBV-B virus pool, the consensus clone pGBB5-1 which lacks the 3' terminal sequence of GBV-B is thus not infectious in vivo.

Figure 5:
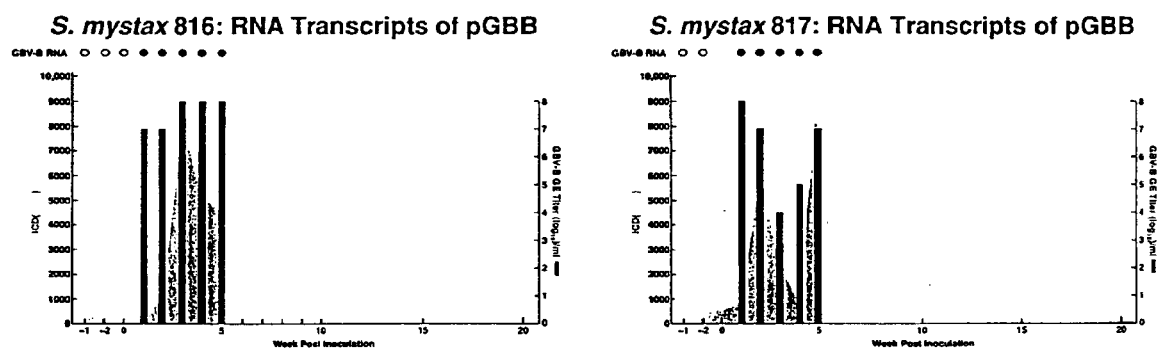
FIG. 5 shows the course of GBV-B infection in *S. mystax* tamarins transfected with RNA transcripts of pGBB. Both animals were negative for GBV-$A_{SM}$. At week 0 transcription mixtures were injected into tamarins by percutaneous intrahepatic injection guided by ultrasound. Results of qualitative RT-nested PCR for GBV-B in serum is shown at the top (filled circles, positive; empty circles, negative). Serum levels of isocitrate dehydrogenase (ICD in units/ml; shaded area) and the estimated $\log_{10}$ GBV-B GE titer (vertical columns) were plotted against time.

Next, the infectivity of RNA transcripts from the full-length consensus GBV-B cDNA clone pGBB was tested. The pGBB clone was identical to the pGBB5-1 clone except in the 3' UTR. Thus, in addition to a 5' UTR of 445 nucleotides, an ORF of 8592 nucleotides encoding 2864 amino acids and a 3' UTR of 103 nucleotides, the pGBB clone also contains an additional 259 nucleotides in its 3' UTR. pGBB was linearized at the XhoI site which added an additional C residue at the 3' end of the transcribed GBV-B RNA. When RNA transcripts from the pGBB clone were injected into the liver of two tamarins (S. mystax 816 and 817), both tamarins became infected with GBV-B with viremia at week 1 p.i. and peak viral titers of $10^8$ GE/ml (FIG. 5). The consensus sequence of PCR products of the complete ORF, amplified from serum obtained during week 2 p.i. from one tamarin (S. mystax 817), was identical to the sequence of pGBB, including at the two positions which differed from the consensus sequence of the cloning source and from the published sequence of GBV-B (Table 1). By performing RT-PCR as desired above, it was demonstrated that the very 3' terminal GBV-B sequence of pGBB existed in the circulating viruses in this tamarin. Within two weeks of the transfection both tamarins developed hepatitis with dramatically elevated liver enzyme levels (FIG. 5). Thus, the pGBB clone is infectious in vivo whereas the clone pGBB5-1 which lacks the last 259 nucleotides was not.

REFERENCES

1. Alter, H. J., Nakatsuji, Y., Melpolder, J., Wages, J., Wesley, R., Shih, J. W.-K. & Kim, J. P. (1997) The incidence of transfusion-associated hepatitis G virus infection and its relation to liver disease. N. Engl. J. Med. 336, 747–754.
2. Alter, M. J., Gallagher, M., Morris, T. T., Moyer, L. A., Meeks, E. L., Krawczynski, K., Kim, J. P. & Margolis, H. S. (1997) Acute non-A-E hepatitis in the United States and the role of hepatitis G virus infection. N. Engl. J. Med. 336, 741–746.
3. Bukh, J. & Apgar, C. L. (1997a) Five new or recently discovered (GBV-A) virus species are indigenous to New World monkeys and may constitute a separate genus of the Flaviviridae. Virology 229, 429–436.
4. Bukh, J., Apgar, C. L., Engle, R., Govindarajan, S., Hegerich, P. A., Tellier, R., Wong, D.C., Elkins, R. & Kew, M. C. (1998b) Experimental infection of chimpanzees with hepatitis C virus of genotype 5a: genetic analysis of the virus and generation of a standardized challenge pool. J. Infect. Dis. 178, 1193–1197.
5. Bukh, J., Apgar, C. L. and Purcell, R. H. (1997b) Natural history of GBV-A and GBV-B in animal models: discovery of indigenous Flaviviridae-like viruses in several species of New World monkeys. In Viral Hepatitis and Liver Disease (Proceedings of the IX Triennial International Symposium on Viral Hepatitis and Liver Disease, Rome, Italy, 1996) (M. Rizzetto, R. H. Purcell, J. L. Gerin, G. Verme, Eds.), pp. 392–395. Edizione Minerva Medica, Turin, Italy.
6. Bukh, J., Kim, J. P., Govindarajan, S., Apgar, C. L., Foung, S. K. H., Wages, J., Yun, A. J., Shapiro, M., Emerson, S. U. & Purcell, R. H. (1998a) Experimental infection of chimpanzees with hepatitis G virus and genetic analysis of the virus. J. Infect. Dis. 177, 855–862.
7. Bukh, J., Miller, R. H. & Purcell, R. H. (1995) Genetic heterogeneity of hepatitis C virus: quasispecies and genotypes. Semin. Liver Dis. 15, 41–63.
8. Deinhardt, F., Holmes, A. W., Capps, R. B. & Popper, H. (1967) Studies on the transmission of human viral hepatitis to marmoset monkeys: Transmission of disease, serial passages, and description of liver lesions. *J. Exp. Med.* 125, 673–687.
9. Emerson, S. U., Lewis, M., Govindarajan, S., Shapiro, M., Moskal, T. & Purcell, R. H. (1992) cDNA clone of hepatitis A virus encoding a virulent virus: induction of viral hepatitis by direct nucleic acid transfection of marmosets. *J. Virol.* 66, 6649–6654.
10. Erker, J. C., Desai, S. M., Leary, T. P., Chalmers, M. L., Montes, C. C. & Mushahwar, I. K. (1998) Genomic analysis of two GB virus A variants isolated from captive monkeys. *J. Gen. Virol.* 79, 41–45.
11. Frolov, I., McBride, M. S. & Rice, C. M. (1998) Cis-acting RNA elements required for replication of bovine viral diarrhea virus-hepatits C virus 5' nontranslated region chimeras. *RNA* 4, 1418–1435.
12. Houghton, M. (1996) Hepatitis C viruses. In "Fields Virology" (B. N. Fields, D. M. Knipe, P. M. Howley, et al., Eds.), Third ed., pp. 1035–1058. Lippincott-Raven Publishers, Philadelphia.
13. Kolykhalov, A. A., Feinstone, S. M. & Rice, C. M. (1996) Identification of a highly conserved sequence element at the 3' terminus of hepatitis C virus genome RNA. *J. Virol.* 70, 3363–3371.
14. Kolykhalov, A. A., Agapov, E. V., Blight, K. J., Mihalik, K., Feinstone, S. M. & Rice, C. M. (1997) Transmission of hepatitis C by intrahepatic inoculation with transcribed RNA. *Science* 277, 570–574.
15. Lemon, S. M. & Honda, M. (1997) Internal ribosome entry sites within the RNA genomes of hepatits C virus and other flaviviruses. *Semin. Virol.* 8, 274–288.
16. Linnen, J., Wages, J., Jr., Zhang-Keck, Z. Y., Fry, K. E., Krawczynski, K. Z., Alter, H., Koonin, E., Gallagher, M., Alter, M., Hadziyannis, S., Karayiannis, P., Fung, K., Nakatsuji, Y., Shih, J. W.-K., Young, L., Piatak, M., Jr., Hoover, C., Fernandez, J., Chen, S., Zou, J.-C., Morris, T., Hyams, K. C., Ismay, S., Lifson, J. D., Hess, G., Foung, S. K. H., Thomas, H., Bradley, D., Margolis, H. & Kim, J. P. (1996) Molecular cloning and disease association of hepatitis G virus: A transfusion-transmissible agent. *Science* 271, 505–508.
17. Lu, H. -H. & Wimmer, E. (1996) Poliovirus chimeras replicating under the translational control of genetic elements of hepatitis C virus reveal unusual properties of the internal ribosomal entry site of hepatitis C virus. *Proc. Natl. Acad. Sci. USA* 93, 1412–1417.
18. Muerhoff, A. S., Leary, T. P., Simons, J. N., Pilot-Matias, T. J., Dawson, G. J., Erker, J. C., Chalmers, M. L., Schlauder, G. G., Desai, S. M. & Mushahwar I. K. (1995) Genomic organization of GB viruses A and B: Two new members of the Flaviviridae associated with GB agent hepatitis. *J. Virol.* 69, 5621–5630.
19. Purcell R H. (1993) The discovery of the hepatitis viruses. *Gastroenterology* 104, 955–963.
20. Rice, C. M. (1996) Flaviviridae: The viruses and their replication, In "Fields Virology". (B. N. Fields, D. M. Knipe, P. M. Howley, et al., Eds.), Third ed., pp. 931–959. Lippincott-Raven Publishers, Philadelphia.
21. Robertson, B., Myers, G., Howard, C., Brettin, T., Bukh, J., Gaschen, B., Gojobori, T., Maertens, G., Mizokami, M., Nainan, O., Netesov, S., Nishioka, K., Shin-i, T., Simmonds, P., Smith, D., Stuyver, L. & Weiner, A. (1998). Classification, nomenclature, and database development for hepatitis C virus (HCV) and related viruses: proposals for standardization. *Arch. Virol.* 143, 2493–2503.
22. Scarcelli, E., Urbani, A., Sbardellati, A., Tomei, L., De Francesco, R. & Traboni, C. (1997) GB virus B and hepatitis C virus NS3 serine proteases share substrate specificity. *J. Virol.* 71, 4985–4989.
23. Schlauder, G. G., Dawson, G. J., Simons, J. N., Pilot-Matias, T. J., Gutierrez, R. A., Heynen, C. A., Knigge, M. F., Kurpiewski, G. S., Buijk, S. L., Leary, T. P., Muerhoff, A. S., Desai, S. M. & Mushahwar I. K. (1995) Molecular and serologic analysis in the transmission of the GB hepatitis agents. *J. Med. Virol.* 46, 81–90.
24. Simons, J. N., Pilot-Matias, T. J., Leary, T. P., Dawson, G. J., Desai, S. M., Schlauder, G. G., Muerhoff, A. S., Erker, J. C., Buijk, S. L., Chalmers, M. L., Van Sant, C. L. & Mushahwar, I. K. (1995a) Identification of two flavivirus-like genomes in the GB hepatitis agent. *Proc. Natl. Acad. Sci. USA* 92, 3401–3405.
25. Simons, J. N., Leary, T. P., Dawson, G. J., Pilot-Matias, T. J., Muerhoff, A. S., Schlauder, G. G., Desai, S. M. & Mushahwar, I. K. (1995b) Isolation of novel virus-like sequences associated with human hepatitis. *Nature Med.* 1, 564–569.
26. Tanaka, T., Kato, N., Cho, M. -J. & Shimotohno, K. (1995) A novel sequence found at the 3' terminus of hepatitis C virus genome. *Biochem. Biophys. Res. Commun.* 215, 744–749.
27. Tellier, R., Bukh, J., Emerson, S. U., Miller, R. H. & Purcell, R. H. (1996) Long PCR and its application to hepatitis viruses: amplification of hepatitis A, hepatitis B, and hepatitis C virus genomes. *J. Clin. Microbiol.* 34, 3085–3091.
28. Yanagi, M., Purcell, R. H., Emerson, S. U. & Bukh, J. (1997) Transcripts from a single full-length cDNA clone of hepatitis C virus are infectious when directly transfected into the liver of a chimpanzee. *Proc. Natl. Acad. Sci. USA* 94, 8738–8743.
29. Yanagi, M., St. Claire, M., Shapiro, M., Emerson, S. U., Purcell, R. H. & Bukh, J. (1998) Transcripts of a chimeric cDNA clone of hepatitis C virus genotype 1b are infectious in vivo. *Virology* 244, 161–172.
30. Yanagi, M., St. Claire, M., Emerson, S. U., Purcell, R. H. & Bukh, J. (1999) In vivo analysis of the 3' untranslated region of the hepatitis C virus after in vitro mutagenesis of an infectious cDNA clone. *Proc. Natl. Acad. Sci. USA* 96, 2291–2295.

What is claimed is:

1. An isolated nucleic acid molecule which encodes GB virus-B having a complete 3'UTR and which is capable of producing infectious virus when transfected into cells in vivo, wherein the 3'UTR includes by the last 259 nucleotides of SEQ ID NO: 1.

2. The nucleic acid molecule of claim 1, wherein said molecule encodes the amino acid sequence of SEQ ID NO: 2.

3. The nucleic acid molecule of claim 2, wherein said molecule comprises the nucleic acid sequence of SEQ ID NO: 1.

4. A DNA construct comprising a nucleic acid molecule according to claim 1.

5. A DNA construct comprising a nucleic acid molecule according to claim 3.

6. An isolated RNA transcript of the DNA construct of claims 4 or 5.

7. An isolated cell transfected with the DNA construct of claims 4 or 5.

8. An isolated cell transfected with RNA transcripts of claim 6.

9. An isolated GB virus-B produced by the cell of claim 7.

10. An isolated GB virus-B produced by the cell of claim 8.

11. An isolated GB virus-B whose genome comprises a nucleic acid molecule according to claim 1.

12. An isolated GB virus-B whose genome comprises a nucleic acid molecule according to claim 3.

13. A method for producing a GB virus-B comprising transfecting a host cell with the DNA construct of claims 4 or 5.

14. A method for producing a GB virus-B comprising transfecting a host cell with the RNA transcript of claim 6.

15. A composition comprising a nucleic acid molecule of claim 1 suspended in a pharmaceutically acceptable diluent or excipient.

16. A composition comprising a nucleic acid molecule of claim 3 suspended in a pharmaceutically acceptable diluent or excipient.

* * * * *

UNITED STATES PATENT AND TRADEMARK OFFICE
CERTIFICATE OF CORRECTION

| | |
|---|---|
| PATENT NO. | : 7,129,342 B1 |
| APPLICATION NO. | : 10/009002 |
| DATED | : October 31, 2006 |
| INVENTOR(S) | : Bukh et al. |

Page 1 of 1

It is certified that error appears in the above-identified patent and that said Letters Patent is hereby corrected as shown below:

In Col. 115, Line 66, Claim 1, after "includes" delete "by".

Signed and Sealed this

Fifth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 7,129,342 B1
APPLICATION NO. : 10/009002
DATED : October 31, 2006
INVENTOR(S) : Bukh et al.

It is certified that error appears in the above-identified patent and that said Letters Patent is hereby corrected as shown below:

In Col. 115, Line 66, Claim 1, after "includes" delete "by".

Signed and Sealed this

Nineteenth Day of June, 2007

JON W. DUDAS
*Director of the United States Patent and Trademark Office*

SEQUENCE LISTING

<160> NUMBER OF SEQ ID NOS: 13

<210> SEQ ID NO 1
<211> LENGTH: 9399
<212> TYPE: DNA

-continued

<213> ORGANISM: GBV-B virus

<400> SEQUENCE: 1
accacaaaca ctccagtttg ttacactccg ctaggaatgc tcctggagca cccccccctag 60 cagggcgtgg gggatttccc ctgcccgtct gcagaagggt ggagccaacc accttagtat 120
gtaggcggcg ggactcatga cgctcgcgtg atgacaagcg ccaagcttga cttggatggc 180
cctgatgggc gttcatgggt tcggtggtgg tggcgcttta ggcagcctcc acgcccacca 240
cctcccagat agagcggcgg cactgtaggg aagaccgggg accggtcact accaaggacg 300
cagacctctt tttgagtatc acgcctccgg aagtagttgg gcaagcccac ctatatgtgt 360
tgggatggtt ggggttagcc atccataccg tactgcctga tagggtcctt gcgaggggat 420
ctgggagtct cgtagaccgt agcacatgcc tgttatttct actcaaacaa gtcctgtacc 480
tgcgcccaga acgcgcaaga acaagcagac gcaggcttca tatcctgtgt ccattaaaac 540
atctgttgaa aggggacaac gagcaaagcg caaagtccag cgcgatgctc ggcctcgtaa 600
ttacaaaatt gctggtatcc atgatggctt gcagacattg gctcaggctg ctttgccagc 660
tcatggttgg ggacgccaag accctcgcca taagtctcgc aatcttggaa tccttctgga 720
ttaccctttg gggtggattg gtgatgttac aactcacaca cctctagtag gcccgctggt 780
ggcaggagcg gtcgttcgac cagtctgcca gatagtacgc ttgctggagg atggagtcaa 840
ctgggctact ggttggttcg gtgtccacct ttttgtggta tgtctgctat ctttggcctg 900
tccctgtagt ggggcgcggg tcactgaccc agacacaaat accacaatcc tgaccaattg 960
ctgccagcgt aatcaggtta tctattgttc tccttccact tgcctacacg agcctggttg 1020
tgtgatctgt gcggacgagt gctgggttcc cgccaatccg tacatctcac acccttccaa 1080
ttggactggc acggactcct tcttggctga ccacattgat tttgttatgg gcgctcttgt 1140
gacctgtgac gcccttgaca ttggtgagtt gtgtggtgcg tgtgtattag tcggtgactg 1200
gcttgtcagg cactggctta ttcacataga cctcaatgaa actggtactt gttacctgga 1260
agtgcccact ggaatagatc ctgggttcct agggtttatc gggtggatgg ccggcaaggt 1320
cgaggctgtc atcttcttga ccaaactggc ttcacaagta ccatacgcta ttgcgactat 1380
gtttagcagt gtacactacc tggcggttgg cgctctgatc tactatgcct ctcggggcaa 1440
gtggtatcag ttgctcctag cgcttatgct ttacatagaa gcgacctctg gaaaccccat 1500
cagggtgccc actggatgct caatagctga gttttgctcg cctttgatga taccatgtcc 1560
ttgccactct tatttgagtg agaatgtgtc agaagtcatt tgttacagtc caaagtggac 1620
caggcctatc actctagagt ataacaactc catatcttgg taccccctata caatccctgg 1680 tgcgagggga tgtatggtta aattcaaaaa taacacatgg ggttgctgcc gtattcgcaa 1740
tgtgccatcg tactgcacta tgggcactga tgcagtgtgg aacgacactc gcaacactta 1800
cgaagcatgc ggtgtaacac catggctaac aaccgcatgg cacaacggct cagccctgaa 1860
attggctata ttacaatacc ctgggtctaa agaaatgttt aaacctcata attggatgtc 1920
aggccatttg tattttgagg gatcagatac ccctatagtt tacttttatg accctgtgaa 1980
ttccactctc ctaccaccgg agaggtgggc taggttgccc ggtaccccac ctgtggtacg 2040
tggttcttgg ttacaggttc cgcaagggtt ttacagtgat gtgaaagacc tagccacagg 2100
attgatcacc aaagacaaag cctggaaaaa ttatcaggtc ttatattccg ccacgggtgc 2160
tttgtctctt acgggagtta ccaccaaggc cgtggtgcta attctgttgg ggttgtgtgg 2220
cagcaagtat cttattttag cctacctctg ttacttgtcc ctttgttttg ggcgcgcttc 2280

```
tggttaccct ttgcgtcctg tgctcccatc ccagtcgtat ctccaagctg gctgggatgt   2340
tttgtctaaa gctcaagtag ctccttttgc tttgattttc ttcatctgtt gctatctccg   2400
ctgcaggcta cgttatgctg cccttttagg gtttgtgccc atggctgcgg gcttgcccct   2460
aactttcttt gttgcagcag ctgctgccca accagattat gactggtggg tgcgactgct   2520
agtggcaggg ttagttttgt gggccggccg taaccgtggt caccgcatag ctctgcttgt   2580
aggtccttgg cctctggtag cgcttttaac cctcttgcat ttggttacgc ctgcttcagc   2640
ttttgatacc gagataattg gagggctgac aataccacct gtagtagcat tagttgtcat   2700
gtctcgtttt ggcttctttg ctcacttgtt acctcgctgt gctttagtta actcctatct   2760
ttggcaacgt tgggagaatt ggttttggaa cgttacacta agaccggaga gttttttcct   2820
tgtgctggtt tgtttccccg gtgcgacata tgacgcgctg gtgactttct gtgtgtgtca   2880
cgtagctctt ctatgtttaa catccagtgc agcatcgttc tttgggactg actctagggt   2940
tagggcccat agaatgttgg tgcgtctcgg aaagtgtcat gcttggtatt ctcattatgt   3000
tcttaagttt ttcctcttag tgtttggtga aatggtgtg ttttctata agcacttgca   3060 tggtgatgtc ttgcctaatg attttgcctc gaaactacca ttgcaagagc cattttccc    3120 ttttgaaggc aaggcaaggg tctataggaa tgaaggaaga cgcttggcgt gtggggacac   3180
ggttgatggt ttgcccgttg ttgcgcgtct cggcgacctt gttttcgcag ggttggctat   3240
gccgccagat gggtgggcca ttaccgcacc ttttacgctg cagtgtctct ctgaacgtgg   3300
cacgctgtca gcgatggcag tggtcatgac tggtatagac ccccgaactt ggactggaac   3360
tatcttcaga ttaggatctc tggccactag ctacatggga tttgtttgtg acaacgtgtt   3420
gtatactgct caccatggca gcaaggggcg ccggttggct catcccacag gctctataca   3480
cccaataacc gttgacgcgg ctaatgacca ggacatctat caaccaccat gtggagctgg   3540
gtcccttact cggtgctctt gcggggagac caagggtat ctggtaacac gactggggtc    3600
attggttgag gtcaacaaat ccgatgaccc ttattggtgt gtgtgcgggg cccttcccat   3660
ggctgttgcc aagggttctt caggtgcccc gattctgtgc tcctccgggc atgttattgg   3720
gatgttcacc gctgctagaa attctggcgg ttcagtcagt cagattaggg ttaggccgtt   3780
ggtgtgtgct ggataccatc cccagtacac agcacatgcc actcttgata caaaacctac   3840
tgtgcctaac gagtattcag tgcaaatttt aattgccccc actggcagcg gcaagtcaac   3900
caaattacca ctttcttaca tgcaggagaa gtatgaggtc ttggtcctaa atcccagtgt   3960
ggctacaaca gcatcaatgc caaagtacat gcacgcgacg tacggcgtga atccaaattg   4020 ctatttttaat ggcaaatgta ccaacacagg ggcttcactt acgtacagca catatggcat   4080
gtacctgacc ggagcatgtt cccggaacta tgatgtaatc atttgtgacg aatgccatgc   4140
taccgatgca accaccgtgt tgggcattgg aaaggtccta accgaagctc catccaaaaa   4200
tgttaggcta gtggttcttg ccacggctac ccccccctgga gtaatcccta caccacatgc   4260
caacataact gagattcaat taaccgatga aggcactatc cccttcatg gaaaaaagat    4320 taaggaggaa aatctgaaga aagggagaca ccttatcttt gaggctacca aaaacactg    4380 tgatgagctt gctaacgagt tagctcgaaa gggaataaca gctgtctctt actatagggg   4440
atgtgacatc tcaaaaatcc ctgagggcga ctgtgtagta gttgccactg atgccttgtg   4500
tacagggtac actggtgact ttgattccgt gtatgactgc agcctcatgg tagaaggcac   4560
atgccatgtt gaccttgacc ctactttcac catgggtgtt cgtgtgtgcg ggtttcagc    4620
```

-continued

```
aatagttaaa ggccagcgta ggggccgcac aggccgtggg agagctggca tatactacta      4680
tgtagacggg agttgtaccc cttcgggtat ggttcctgaa tgcaacattg ttgaagcctt      4740
cgacgcagcc aaggcatggt atggtttgtc atcaacagaa gctcaaacta ttctggacac      4800
ctatcgcacc caacctgggt tacctgcgat aggagcaaat ttggacgagt gggctgatct      4860
cttttctatg gtcaaccccg aaccttcatt tgtcaatact gcaaaaagaa ctgctgacaa      4920
ttatgttttg ttgactgcag cccaactaca actgtgtcat cagtatggct atgctgctcc      4980
caatgacgca ccacggtggc agggagcccg gcttgggaaa aaaccttgtg gggttctgtg      5040
gcgcttggac ggcgctgacg cctgtcctgg cccagagccc agcgaggtga ccagatacca      5100
aatgtgcttc actgaagtca atacttctgg gacagccgca ctcgctgttg gcgttggagt      5160
ggctatggct tatctagcca ttgacacttt tggcgccact tgtgtgcggc gttgctggtc      5220
tattacatca gtccctaccg gtgctactgt cgccccagtg gttgacgaag aagaaatcgt      5280
ggaggagtgt gcatcattca ttcccttgga ggccatggtt gctgcaattg acaagctgaa      5340
gagtacaatc accacaacta gtcctttcac attggaaacc gcccttgaaa aacttaacac      5400
ctttcttggg cctcatgcag ctacaatcct tgctatcata gagtattgct gtggtttagt      5460
cactttacct gacaatccct ttgcatcatg cgtgtttgct ttcattgcgg gtattactac      5520
cccactacct cacaagatca aaatgttcct gtcattattt ggaggcgcaa ttgcgtccaa      5580
gcttacagac gctagaggcg cactggcgtt catgatggcc ggggctgcgg aacagctct      5640
tggtacatgg acatcggtgg gttttgtctt tgacatgcta gcggctatg ctgccgcctc      5700
atccactgct tgcttgacat ttaaatgctt gatgggtgag tggcccacta tggatcagct      5760
tgctggttta gtctactccg cgttcaatcc ggccgcagga gttgtgggcg tcttgtcagc      5820
ttgtgcaatg tttgctttga caacagcagg gccagatcac tggcccaaca gacttcttac      5880
tatgcttgct aggagcaaca ctgtatgtaa tgagtacttt attgccactc gtgacatccg      5940
caggaagata ctgggcattc tggaggcatc tacccctgg agtgtcatat cagcttgcat      6000
ccgttggctc cacaccccga cggaggatga ttgcggcctc attgcttggg gtctagagat      6060
ttggcagtat gtgtgcaatt tctttgtgat ttgctttaat gtccttaaag ctggagttca      6120
gagcatggtt aacattcctg ttgtcctttt ctacagctgc cagaaggggt acaagggccc      6180
ctggattgga tcaggtatgc tccaagcacg ctgtccatgc ggtgctgaac tcatcttttc      6240
tgttgagaat ggttttgcaa aactttacaa aggacccaga acttgttcaa attactggag      6300
aggggctgtt ccagtcaacg ctaggctgtg tgggtcggct agaccggacc caactgattg      6360
gactagtctt gtcgtcaatt atggcgttag ggactactgt aaatatgaga aaatgggaga      6420
tcacattttt gttacagcag tatcctctcc aaatgtctgt ttcacccagg tgcccccaac      6480
cttgagagct gcagtggccg tggacggcgt acaggttcag tgttatctag gtgagcccaa      6540
aactccttgg acgacatctg cttgctgtta cggtcctgac ggtaagggta aaactgttaa      6600
gcttcccttc cgcgttgacg gtcacacacc tggtgtgcgc atgcaactta atttgcgtga      6660
tgcacttgag acaaatgact gtaattccac aaacaacact cctagtgatg aagccgcagt      6720
gtccgctctt gttttcaaac aggagttgcg gcgtacaaac caattgcttg aggcaatttc      6780
agctggcgtt gacaccacca aactgccagc cccctccatc gaagaggtag tggtaagaaa      6840
gcgccagttc cgggcaagaa ctggttcgct taccttgcct ccccctccga gatccgtccc      6900
aggagtgtca tgtcctgaaa gcctgcaacg aagtgacccg ttagaaggtc cttcaaacct      6960
ccctccttca ccacctgttc tacagttggc catgccgatg cccctgttgg gagcgggtga      7020
```

```
gtgtaaccct tcactgcaa ttggatgtgc aatgaccgaa acaggcggag gccctgatga    7080
tttacccagt taccctccca aaaggaggt ctctgaatgg tcagacgaaa gttggtcgac    7140
ggctacaacc gcttccagct acgttactgg ccccccgtac cctaagatac ggggaaagga    7200
ttccactcag tcagcccccg ccaaacggcc tacaaaaaag aagttgggaa agagtgagtt    7260
ttcgtgcagc atgagctaca cctggaccga cgtgattagc ttcaaaactg cttctaaagt    7320
tctgtctgca actcgggcca tcactagtgg tttcctcaaa caaagatcat tggtgtatgt    7380
gactgagccg cgggatgcgg agcttagaaa acaaaaagtc actattaata gacaacctct    7440 gttccccca tcataccaca agcaagtgag attggctaag gaaaaagctt caaaagttgt    7500
cggtgtcatg tgggactatg atgaagtagc agctcacacg ccctctaagt ctgctaagtc    7560
ccacatcact ggccttcggg gcactgatgt tcgttctgga gcagcccgca aggctgttct    7620
ggacttgcag aagtgtgtcg aggcaggtga gataccgagt cattatcggc aaactgtgat    7680
agttccaaag gaggaggtct tcgtgaagac cccccagaaa ccaacaaaga accccccaag    7740
gcttatctcg tacccccacc ttgaaatgag atgtgttgag aagatgtact acggtcaggt    7800
tgctcctgac gtagttaaag ctgtcatggg agatgcgtac gggtttgtag atccacgtac    7860
ccgtgtcaag cgtctgttgt cgatgtggtc acccgatgca gtcggagcca catgcgatac    7920
agtgtgtttt gacagtacca tcacacccga ggatatcatg gtggagacag acatctactc    7980
agcagctaaa ctcagtgacc aacaccgagc tggcattcac accattgcga ggcagttata    8040
cgctggagga ccgatgatcg cttatgatgg ccgagagatc ggatatcgta ggtgtaggtc    8100
ttccggcgtc tatactacct caagttccaa cagtttgacc tgctggctga aggtaaatgc    8160
tgcagccgaa caggctggca tgaagaaccc tcgcttcctt atttgcggcg atgattgcac    8220
cgtaatttgg aagagcgccg gagcagatgc agacaaacaa gcaatgcgtg tctttgctag    8280
ctggatgaag gtgatgggtg caccacaaga ttgtgtgcct caacccaaat acagtttgga    8340
agaattaaca tcatgctcat caaatgttac ctctggaatt accaaaagtg caagcctta    8400 ctactttctt acaagagatc ctcgtatccc ccttggcagg tgctctgccg agggtctggg    8460
atacaacccc agtgctgcgt ggattgggta tctaatacat cactacccat gtttgtgggt    8520
tagccgtgtg ttggctgtcc atttcatgga gcagatgctc tttgaggaca aacttcccga    8580
gactgtgacc tttgactggt atgggaaaaa ttatacggtg cctgtagaag atctgcccag    8640
catcattgct ggtgtgcacg gtattgaggc ttttctcggtg gtgcgctaca ccaacgctga    8700
gatcctcaga gtttcccaat cactaacaga catgaccatg ccccccctgc gagcctggcg    8760
aaagaaagcc agggcggtcc tcgccagcgc caagaggcgt ggcggagcac acgcaaaatt    8820
ggctcgcttc cttctctggc atgctacatc tagacctcta ccagatttgg ataagacgag    8880
cgtggctcgg tacaccactt tcaattattg tgatgtttac tccccggagg gggatgtgtt    8940
tattacacca cagagaagat tgcagaagtt ccttgtgaag tatttggctg tcattgtttt    9000
tgccctaggg ctcattgctg ttggattagc catcagctga accccaaat tcaaaattaa    9060 ctaacagttt tttttttttt tttttttttt agggcagcgg caacagggga gaccccgggc    9120
ttaacgaccc cgccgatgtg agtttggcga ccatggtgga tcagaaccgt tcgggtgaa    9180 gccatggtct gaagggggatg acgtccctc tggctcatcc acaaaaccg tctcgggtgg    9240 gtgaggagtc ctggctgtgt gggaagcagt cagtataatt cccgtcgtgt gtggtgacgc    9300
ctcacgacgt atttgtccgc tgtgcagagc gtagtaccaa gggctgcacc ccggttttg    9360
```

-continued

```
ttccaagcgg agggcaaccc ccgcttggaa ttaaaaact                      9399

<210> SEQ ID NO 2
<211> LENGTH: 2864
<212> TYPE: PRT
<213> ORGANISM: GBV-B virus

<400> SEQUENCE: 2

Met Pro Val Ile Ser Thr Gln Thr Ser Pro Val Pro Ala Pro Arg Thr
 1               5                  10                  15

Arg Lys Asn Lys Gln Thr Gln Ala Ser Tyr Pro Val Ser Ile Lys Thr
            20                  25                  30

Ser Val Glu Arg Gly Gln Arg Ala Lys Arg Lys Val Gln Arg Asp Ala
        35                  40                  45

Arg Pro Arg Asn Tyr Lys Ile Ala Gly Ile His Asp Gly Leu Gln Thr
    50                  55                  60

Leu Ala Gln Ala Ala Leu Pro Ala His Gly Trp Gly Arg Gln Asp Pro
65                  70                  75                  80

Arg His Lys Ser Arg Asn Leu Gly Ile Leu Leu Asp Tyr Pro Leu Gly
                85                  90                  95

Trp Ile Gly Asp Val Thr Thr His Thr Pro Leu Val Gly Pro Leu Val
            100                 105                 110

Ala Gly Ala Val Val Arg Pro Val Cys Gln Ile Val Arg Leu Leu Glu
        115                 120                 125

Asp Gly Val Asn Trp Ala Thr Gly Trp Phe Gly Val His Leu Phe Val
    130                 135                 140

Val Cys Leu Leu Ser Leu Ala Cys Pro Cys Ser Gly Ala Arg Val Thr
145                 150                 155                 160

Asp Pro Asp Thr Asn Thr Thr Ile Leu Thr Asn Cys Cys Gln Arg Asn
                165                 170                 175

Gln Val Ile Tyr Cys Ser Pro Ser Thr Cys Leu His Glu Pro Gly Cys
            180                 185                 190

Val Ile Cys Ala Asp Glu Cys Trp Val Pro Ala Asn Pro Tyr Ile Ser
        195                 200                 205

His Pro Ser Asn Trp Thr Gly Thr Asp Ser Phe Leu Ala Asp His Ile
    210                 215                 220

Asp Phe Val Met Gly Ala Leu Val Thr Cys Asp Ala Leu Asp Ile Gly
225                 230                 235                 240

Glu Leu Cys Gly Ala Cys Val Leu Val Gly Asp Trp Leu Val Arg His
                245                 250                 255

Trp Leu Ile His Ile Asp Leu Asn Glu Thr Gly Thr Cys Tyr Leu Glu
            260                 265                 270

Val Pro Thr Gly Ile Asp Pro Gly Phe Leu Gly Phe Ile Gly Trp Met
        275                 280                 285

Ala Gly Lys Val Glu Ala Val Ile Phe Leu Thr Lys Leu Ala Ser Gln
    290                 295                 300

Val Pro Tyr Ala Ile Ala Thr Met Phe Ser Ser Val His Tyr Leu Ala
305                 310                 315                 320

Val Gly Ala Leu Ile Tyr Tyr Ala Ser Arg Gly Lys Trp Tyr Gln Leu
                325                 330                 335

Leu Leu Ala Leu Met Leu Tyr Ile Glu Ala Thr Ser Gly Asn Pro Ile
            340                 345                 350

Arg Val Pro Thr Gly Cys Ser Ile Ala Glu Phe Cys Ser Pro Leu Met
        355                 360                 365
```

-continued

| | | | | | | | | | | | |
|---|---|---|---|---|---|---|---|---|---|---|---|
| Ile | Pro | Cys | Pro | Cys | His | Ser | Tyr | Leu | Ser | Glu | Asn | Val | Ser | Glu | Val |
| | 370 | | | | 375 | | | | 380 | | |

Ile Pro Cys Pro Cys His Ser Tyr Leu Ser Glu Asn Val Ser Glu Val
 370                 375                 380

Ile Cys Tyr Ser Pro Lys Trp Thr Arg Pro Ile Thr Leu Glu Tyr Asn
385                 390                 395                 400

Asn Ser Ile Ser Trp Tyr Pro Tyr Thr Ile Pro Gly Ala Arg Gly Cys
                405                 410                 415

Met Val Lys Phe Lys Asn Asn Thr Trp Gly Cys Cys Arg Ile Arg Asn
        420                 425                 430

Val Pro Ser Tyr Cys Thr Met Gly Thr Asp Ala Val Trp Asn Asp Thr
        435                 440                 445

Arg Asn Thr Tyr Glu Ala Cys Gly Val Thr Pro Trp Leu Thr Thr Ala
        450                 455                 460

Trp His Asn Gly Ser Ala Leu Lys Leu Ala Ile Leu Gln Tyr Pro Gly
465                 470                 475                 480

Ser Lys Glu Met Phe Lys Pro His Asn Trp Met Ser Gly His Leu Tyr
                485                 490                 495

Phe Glu Gly Ser Asp Thr Pro Ile Val Tyr Phe Tyr Asp Pro Val Asn
                500                 505                 510

Ser Thr Leu Leu Pro Pro Glu Arg Trp Ala Arg Leu Pro Gly Thr Pro
        515                 520                 525

Pro Val Val Arg Gly Ser Trp Leu Gln Val Pro Gln Gly Phe Tyr Ser
        530                 535                 540

Asp Val Lys Asp Leu Ala Thr Gly Leu Ile Thr Lys Asp Lys Ala Trp
545                 550                 555                 560

Lys Asn Tyr Gln Val Leu Tyr Ser Ala Thr Gly Ala Leu Ser Leu Thr
                565                 570                 575

Gly Val Thr Thr Lys Ala Val Val Leu Ile Leu Leu Gly Leu Cys Gly
                580                 585                 590

Ser Lys Tyr Leu Ile Leu Ala Tyr Leu Cys Tyr Leu Ser Leu Cys Phe
        595                 600                 605

Gly Arg Ala Ser Gly Tyr Pro Leu Arg Pro Val Leu Pro Ser Gln Ser
        610                 615                 620

Tyr Leu Gln Ala Gly Trp Asp Val Leu Ser Lys Ala Gln Val Ala Pro
625                 630                 635                 640

Phe Ala Leu Ile Phe Phe Ile Cys Cys Tyr Leu Arg Cys Arg Leu Arg
                645                 650                 655

Tyr Ala Ala Leu Leu Gly Phe Val Pro Met Ala Ala Gly Leu Pro Leu
        660                 665                 670

Thr Phe Phe Val Ala Ala Ala Ala Gln Pro Asp Tyr Asp Trp Trp
        675                 680                 685

Val Arg Leu Leu Val Ala Gly Leu Val Leu Trp Ala Gly Arg Asn Arg
        690                 695                 700

Gly His Arg Ile Ala Leu Leu Val Gly Pro Trp Pro Leu Val Ala Leu
705                 710                 715                 720

Leu Thr Leu Leu His Leu Val Thr Pro Ala Ser Ala Phe Asp Thr Glu
                725                 730                 735

Ile Ile Gly Gly Leu Thr Ile Pro Pro Val Val Ala Leu Val Val Met
                740                 745                 750

Ser Arg Phe Gly Phe Ala His Leu Leu Pro Arg Cys Ala Leu Val
        755                 760                 765

Asn Ser Tyr Leu Trp Gln Arg Trp Glu Asn Trp Phe Trp Asn Val Thr
        770                 775                 780

Leu Arg Pro Glu Arg Phe Phe Leu Val Leu Val Cys Phe Pro Gly Ala

-continued

```
            785                 790                 795                 800
Thr Tyr Asp Ala Leu Val Thr Phe Cys Val Cys His Val Ala Leu Leu
                805                 810                 815
Cys Leu Thr Ser Ser Ala Ala Ser Phe Phe Gly Thr Asp Ser Arg Val
                820                 825                 830
Arg Ala His Arg Met Leu Val Arg Leu Gly Lys Cys His Ala Trp Tyr
                835                 840                 845
Ser His Tyr Val Leu Lys Phe Phe Leu Leu Val Phe Gly Glu Asn Gly
                850                 855                 860
Val Phe Phe Tyr Lys His Leu His Gly Asp Val Leu Pro Asn Asp Phe
865                 870                 875                 880
Ala Ser Lys Leu Pro Leu Gln Glu Pro Phe Phe Pro Phe Glu Gly Lys
                885                 890                 895
Ala Arg Val Tyr Arg Asn Glu Gly Arg Arg Leu Ala Cys Gly Asp Thr
                900                 905                 910
Val Asp Gly Leu Pro Val Val Ala Arg Leu Gly Asp Leu Val Phe Ala
                915                 920                 925
Gly Leu Ala Met Pro Pro Asp Gly Trp Ala Ile Thr Ala Pro Phe Thr
                930                 935                 940
Leu Gln Cys Leu Ser Glu Arg Gly Thr Leu Ser Ala Met Ala Val Val
945                 950                 955                 960
Met Thr Gly Ile Asp Pro Arg Thr Trp Thr Gly Thr Ile Phe Arg Leu
                965                 970                 975
Gly Ser Leu Ala Thr Ser Tyr Met Gly Phe Val Cys Asp Asn Val Leu
                980                 985                 990
Tyr Thr Ala His His Gly Ser Lys Gly Arg Arg Leu Ala His Pro Thr
                995                 1000                1005
Gly Ser Ile His Pro Ile Thr Val Asp Ala Ala Asn Asp Gln Asp Ile
                1010                1015                1020
Tyr Gln Pro Pro Cys Gly Ala Gly Ser Leu Thr Arg Cys Ser Cys Gly
1025                1030                1035                1040
Glu Thr Lys Gly Tyr Leu Val Thr Arg Leu Gly Ser Leu Val Glu Val
                1045                1050                1055
Asn Lys Ser Asp Asp Pro Tyr Trp Cys Val Cys Gly Ala Leu Pro Met
                1060                1065                1070
Ala Val Ala Lys Gly Ser Ser Gly Ala Pro Ile Leu Cys Ser Ser Gly
                1075                1080                1085
His Val Ile Gly Met Phe Thr Ala Ala Arg Asn Ser Gly Gly Ser Val
                1090                1095                1100
Ser Gln Ile Arg Val Arg Pro Leu Val Cys Ala Gly Tyr His Pro Gln
1105                1110                1115                1120
Tyr Thr Ala His Ala Thr Leu Asp Thr Lys Pro Thr Val Pro Asn Glu
                1125                1130                1135
Tyr Ser Val Gln Ile Leu Ile Ala Pro Thr Gly Ser Gly Lys Ser Thr
                1140                1145                1150
Lys Leu Pro Leu Ser Tyr Met Gln Glu Lys Tyr Glu Val Leu Val Leu
                1155                1160                1165
Asn Pro Ser Val Ala Thr Thr Ala Ser Met Pro Lys Tyr Met His Ala
                1170                1175                1180
Thr Tyr Gly Val Asn Pro Asn Cys Tyr Phe Asn Gly Lys Cys Thr Asn
1185                1190                1195                1200
Thr Gly Ala Ser Leu Thr Tyr Ser Thr Tyr Gly Met Tyr Leu Thr Gly
                1205                1210                1215
```

-continued

Ala Cys Ser Arg Asn Tyr Asp Val Ile Ile Cys Asp Glu Cys His Ala
              1220                1225                1230

Thr Asp Ala Thr Thr Val Leu Gly Ile Gly Lys Val Leu Thr Glu Ala
    1235                1240                1245

Pro Ser Lys Asn Val Arg Leu Val Val Leu Ala Thr Ala Thr Pro Pro
1250                1255                1260

Gly Val Ile Pro Thr Pro His Ala Asn Ile Thr Glu Ile Gln Leu Thr
1265                1270                1275                1280

Asp Glu Gly Thr Ile Pro Phe His Gly Lys Lys Ile Lys Glu Glu Asn
              1285                1290                1295

Leu Lys Lys Gly Arg His Leu Ile Phe Glu Ala Thr Lys Lys His Cys
              1300                1305                1310

Asp Glu Leu Ala Asn Glu Leu Ala Arg Lys Gly Ile Thr Ala Val Ser
              1315                1320                1325

Tyr Tyr Arg Gly Cys Asp Ile Ser Lys Ile Pro Glu Gly Asp Cys Val
              1330                1335                1340

Val Val Ala Thr Asp Ala Leu Cys Thr Gly Tyr Thr Gly Asp Phe Asp
1345                1350                1355                1360

Ser Val Tyr Asp Cys Ser Leu Met Val Glu Gly Thr Cys His Val Asp
              1365                1370                1375

Leu Asp Pro Thr Phe Thr Met Gly Val Arg Val Cys Gly Val Ser Ala
              1380                1385                1390

Ile Val Lys Gly Gln Arg Arg Gly Arg Thr Gly Arg Gly Arg Ala Gly
              1395                1400                1405

Ile Tyr Tyr Tyr Val Asp Gly Ser Cys Thr Pro Ser Gly Met Val Pro
    1410                1415                1420

Glu Cys Asn Ile Val Glu Ala Phe Asp Ala Ala Lys Ala Trp Tyr Gly
1425                1430                1435                1440

Leu Ser Ser Thr Glu Ala Gln Thr Ile Leu Asp Thr Tyr Arg Thr Gln
              1445                1450                1455

Pro Gly Leu Pro Ala Ile Gly Ala Asn Leu Asp Glu Trp Ala Asp Leu
    1460                1465                1470

Phe Ser Met Val Asn Pro Glu Pro Ser Phe Val Asn Thr Ala Lys Arg
    1475                1480                1485

Thr Ala Asp Asn Tyr Val Leu Leu Thr Ala Ala Gln Leu Gln Leu Cys
    1490                1495                1500

His Gln Tyr Gly Tyr Ala Ala Pro Asn Asp Ala Pro Arg Trp Gln Gly
1505                1510                1515                1520

Ala Arg Leu Gly Lys Lys Pro Cys Gly Val Leu Trp Arg Leu Asp Gly
              1525                1530                1535

Ala Asp Ala Cys Pro Gly Pro Glu Pro Ser Glu Val Thr Arg Tyr Gln
              1540                1545                1550

Met Cys Phe Thr Glu Val Asn Thr Ser Gly Thr Ala Ala Leu Ala Val
              1555                1560                1565

Gly Val Gly Val Ala Met Ala Tyr Leu Ala Ile Asp Thr Phe Gly Ala
    1570                1575                1580

Thr Cys Val Arg Arg Cys Trp Ser Ile Thr Ser Val Pro Thr Gly Ala
1585                1590                1595                1600

Thr Val Ala Pro Val Val Asp Glu Glu Ile Val Glu Glu Cys Ala
              1605                1610                1615

Ser Phe Ile Pro Leu Glu Ala Met Val Ala Ala Ile Asp Lys Leu Lys
    1620                1625                1630

-continued

```
Ser Thr Ile Thr Thr Thr Ser Pro Phe Thr Leu Glu Thr Ala Leu Glu
        1635                1640                1645

Lys Leu Asn Thr Phe Leu Gly Pro His Ala Ala Thr Ile Leu Ala Ile
1650                1655                1660

Ile Glu Tyr Cys Cys Gly Leu Val Thr Leu Pro Asp Asn Pro Phe Ala
1665                1670                1675                1680

Ser Cys Val Phe Ala Phe Ile Ala Gly Ile Thr Thr Pro Leu Pro His
        1685                1690                1695

Lys Ile Lys Met Phe Leu Ser Leu Phe Gly Ala Ile Ala Ser Lys
        1700                1705                1710

Leu Thr Asp Ala Arg Gly Ala Leu Ala Phe Met Met Ala Gly Ala Ala
        1715                1720                1725

Gly Thr Ala Leu Gly Thr Trp Thr Ser Val Gly Phe Val Phe Asp Met
        1730                1735                1740

Leu Gly Gly Tyr Ala Ala Ala Ser Ser Thr Ala Cys Leu Thr Phe Lys
1745                1750                1755                1760

Cys Leu Met Gly Glu Trp Pro Thr Met Asp Gln Leu Ala Gly Leu Val
                1765                1770                1775

Tyr Ser Ala Phe Asn Pro Ala Ala Gly Val Val Gly Val Leu Ser Ala
                1780                1785                1790

Cys Ala Met Phe Ala Leu Thr Thr Ala Gly Pro Asp His Trp Pro Asn
                1795                1800                1805

Arg Leu Leu Thr Met Leu Ala Arg Ser Asn Thr Val Cys Asn Glu Tyr
        1810                1815                1820

Phe Ile Ala Thr Arg Asp Ile Arg Arg Lys Ile Leu Gly Ile Leu Glu
1825                1830                1835                1840

Ala Ser Thr Pro Trp Ser Val Ile Ser Ala Cys Ile Arg Trp Leu His
                1845                1850                1855

Thr Pro Thr Glu Asp Asp Cys Gly Leu Ile Ala Trp Gly Leu Glu Ile
                1860                1865                1870

Trp Gln Tyr Val Cys Asn Phe Phe Val Ile Cys Phe Asn Val Leu Lys
        1875                1880                1885

Ala Gly Val Gln Ser Met Val Asn Ile Pro Gly Cys Pro Phe Tyr Ser
        1890                1895                1900

Cys Gln Lys Gly Tyr Lys Gly Pro Trp Ile Gly Ser Gly Met Leu Gln
1905                1910                1915                1920

Ala Arg Cys Pro Cys Gly Ala Glu Leu Ile Phe Ser Val Glu Asn Gly
                1925                1930                1935

Phe Ala Lys Leu Tyr Lys Gly Pro Arg Thr Cys Ser Asn Tyr Trp Arg
                1940                1945                1950

Gly Ala Val Pro Val Asn Ala Arg Leu Cys Gly Ser Ala Arg Pro Asp
        1955                1960                1965

Pro Thr Asp Trp Thr Ser Leu Val Val Asn Tyr Gly Val Arg Asp Tyr
        1970                1975                1980

Cys Lys Tyr Glu Lys Met Gly Asp His Ile Phe Val Thr Ala Val Ser
1985                1990                1995                2000

Ser Pro Asn Val Cys Phe Thr Gln Val Pro Pro Thr Leu Arg Ala Ala
                2005                2010                2015

Val Ala Val Asp Gly Val Gln Val Gln Cys Tyr Leu Gly Glu Pro Lys
                2020                2025                2030

Thr Pro Trp Thr Thr Ser Ala Cys Cys Tyr Gly Pro Asp Gly Lys Gly
                2035                2040                2045

Lys Thr Val Lys Leu Pro Phe Arg Val Asp Gly His Thr Pro Gly Val
```

-continued

```
           2050                2055                2060
Arg Met Gln Leu Asn Leu Arg Asp Ala Leu Glu Thr Asn Asp Cys Asn
2065                2070                2075                2080

Ser Thr Asn Asn Thr Pro Ser Asp Glu Ala Ala Val Ser Ala Leu Val
                    2085                2090                2095

Phe Lys Gln Glu Leu Arg Arg Thr Asn Gln Leu Leu Glu Ala Ile Ser
            2100                2105                2110

Ala Gly Val Asp Thr Thr Lys Leu Pro Ala Pro Ser Ile Glu Glu Val
            2115                2120                2125

Val Val Arg Lys Arg Gln Phe Arg Ala Arg Thr Gly Ser Leu Thr Leu
            2130                2135                2140

Pro Pro Pro Pro Arg Ser Val Pro Gly Val Ser Cys Pro Glu Ser Leu
2145                2150                2155                2160

Gln Arg Ser Asp Pro Leu Glu Gly Pro Ser Asn Leu Pro Pro Ser Pro
                2165                2170                2175

Pro Val Leu Gln Leu Ala Met Pro Met Pro Leu Leu Gly Ala Gly Glu
            2180                2185                2190

Cys Asn Pro Phe Thr Ala Ile Gly Cys Ala Met Thr Glu Thr Gly Gly
            2195                2200                2205

Gly Pro Asp Asp Leu Pro Ser Tyr Pro Pro Lys Lys Glu Val Ser Glu
            2210                2215                2220

Trp Ser Asp Glu Ser Trp Ser Thr Ala Thr Thr Ala Ser Ser Tyr Val
2225                2230                2235                2240

Thr Gly Pro Pro Tyr Pro Lys Ile Arg Gly Lys Asp Ser Thr Gln Ser
                2245                2250                2255

Ala Pro Ala Lys Arg Pro Thr Lys Lys Lys Leu Gly Lys Ser Glu Phe
            2260                2265                2270

Ser Cys Ser Met Ser Tyr Thr Trp Thr Asp Val Ile Ser Phe Lys Thr
            2275                2280                2285

Ala Ser Lys Val Leu Ser Ala Thr Arg Ala Ile Thr Ser Gly Phe Leu
            2290                2295                2300

Lys Gln Arg Ser Leu Val Tyr Val Thr Glu Pro Arg Asp Ala Glu Leu
2305                2310                2315                2320

Arg Lys Gln Lys Val Thr Ile Asn Arg Gln Pro Leu Phe Pro Pro Ser
                2325                2330                2335

Tyr His Lys Gln Val Arg Leu Ala Lys Glu Lys Ala Ser Lys Val Val
            2340                2345                2350

Gly Val Met Trp Asp Tyr Asp Glu Val Ala Ala His Thr Pro Ser Lys
            2355                2360                2365

Ser Ala Lys Ser His Ile Thr Gly Leu Arg Gly Thr Asp Val Arg Ser
2370                2375                2380

Gly Ala Ala Arg Lys Ala Val Leu Asp Leu Gln Lys Cys Val Glu Ala
2385                2390                2395                2400

Gly Glu Ile Pro Ser His Tyr Arg Gln Thr Val Ile Val Pro Lys Glu
                2405                2410                2415

Glu Val Phe Val Lys Thr Pro Gln Lys Pro Thr Lys Pro Pro Arg
            2420                2425                2430

Leu Ile Ser Tyr Pro His Leu Glu Met Arg Cys Val Glu Lys Met Tyr
            2435                2440                2445

Tyr Gly Gln Val Ala Pro Asp Val Val Lys Ala Val Met Gly Asp Ala
            2450                2455                2460

Tyr Gly Phe Val Asp Pro Arg Thr Arg Val Lys Arg Leu Leu Ser Met
2465                2470                2475                2480
```

-continued

Trp Ser Pro Asp Ala Val Gly Ala Thr Cys Asp Thr Val Cys Phe Asp
            2485            2490            2495

Ser Thr Ile Thr Pro Glu Asp Ile Met Val Glu Thr Asp Ile Tyr Ser
        2500            2505            2510

Ala Ala Lys Leu Ser Asp Gln His Arg Ala Gly Ile His Thr Ile Ala
    2515            2520            2525

Arg Gln Leu Tyr Ala Gly Gly Pro Met Ile Ala Tyr Asp Gly Arg Glu
2530            2535            2540

Ile Gly Tyr Arg Arg Cys Arg Ser Ser Gly Val Tyr Thr Thr Ser Ser
2545            2550            2555            2560

Ser Asn Ser Leu Thr Cys Trp Leu Lys Val Asn Ala Ala Ala Glu Gln
            2565            2570            2575

Ala Gly Met Lys Asn Pro Arg Phe Leu Ile Cys Gly Asp Asp Cys Thr
        2580            2585            2590

Val Ile Trp Lys Ser Ala Gly Ala Asp Ala Asp Lys Gln Ala Met Arg
    2595            2600            2605

Val Phe Ala Ser Trp Met Lys Val Met Gly Ala Pro Gln Asp Cys Val
2610            2615            2620

Pro Gln Pro Lys Tyr Ser Leu Glu Glu Leu Thr Ser Cys Ser Ser Asn
2625            2630            2635            2640

Val Thr Ser Gly Ile Thr Lys Ser Gly Lys Pro Tyr Tyr Phe Leu Thr
            2645            2650            2655

Arg Asp Pro Arg Ile Pro Leu Gly Arg Cys Ser Ala Glu Gly Leu Gly
        2660            2665            2670

Tyr Asn Pro Ser Ala Ala Trp Ile Gly Tyr Leu Ile His His Tyr Pro
    2675            2680            2685

Cys Leu Trp Val Ser Arg Val Leu Ala Val His Phe Met Glu Gln Met
2690            2695            2700

Leu Phe Glu Asp Lys Leu Pro Glu Thr Val Thr Phe Asp Trp Tyr Gly
2705            2710            2715            2720

Lys Asn Tyr Thr Val Pro Val Glu Asp Leu Pro Ser Ile Ile Ala Gly
            2725            2730            2735

Val His Gly Ile Glu Ala Phe Ser Val Val Arg Tyr Thr Asn Ala Glu
        2740            2745            2750

Ile Leu Arg Val Ser Gln Ser Leu Thr Asp Met Thr Met Pro Pro Leu
    2755            2760            2765

Arg Ala Trp Arg Lys Lys Ala Arg Ala Val Leu Ala Ser Ala Lys Arg
2770            2775            2780

Arg Gly Gly Ala His Ala Lys Leu Ala Arg Phe Leu Leu Trp His Ala
2785            2790            2795            2800

Thr Ser Arg Pro Leu Pro Asp Leu Asp Lys Thr Ser Val Ala Arg Tyr
            2805            2810            2815

Thr Thr Phe Asn Tyr Cys Asp Val Tyr Ser Pro Glu Gly Asp Val Phe
        2820            2825            2830

Ile Thr Pro Gln Arg Arg Leu Gln Lys Phe Leu Val Lys Tyr Leu Ala
    2835            2840            2845

Val Ile Val Phe Ala Leu Gly Leu Ile Ala Val Gly Leu Ala Ile Ser
2850            2855            2860

<210> SEQ ID NO 3
<211> LENGTH: 9139
<212> TYPE: DNA
<213> ORGANISM: GBV-B virus -continued

```
<400> SEQUENCE: 3
accacaaaca ctccagtttg ttacactccg ctaggaatgc tcctggagca cccccctag        60 cagggcgtgg gggatttccc ctgcccgtct gcagaagggt ggagccaacc accttagtat       120
gtaggcggcg ggactcatga cgctcgcgtg atgacaagcc caagcttga cttggatggc        180 cctgatgggc gttcatgggt tcggtggtgg tggcgcttta ggcagcctcc acgcccacca       240
cctcccagat agagcggcgg cactgtaggg aagaccgggg accggtcact accaaggacg       300
cagacctctt tttgagtatc acgcctccgg aagtagttgg gcaagcccac ctatatgtgt       360
tgggatggtt ggggttagcc atccataccg tactgcctga tagggtcctt gcgaggggat       420 ctggagtct cgtagaccgt agcacatgcc tgttatttct actcaaacaa gtcctgtacc        480
tgcgcccaga acgcgcaaga acaagcgagc gcaggcttca tatcctgtgt ccattaaaac       540
atctgttgaa aggggacaac gagcaaagcg caaagtccag cgcgatgctc ggcctcgtaa       600
ttacaaaatt gctggtatcc atgatggctt gcagacattg gctcaggctg ctttgccagc       660
tcatggttgg ggacgccaag accctcgcca taagtctcgc aatcttggaa tccttctgga       720
ttaccctttg gggtggattg gtgatgttac aactcacaca cctctagtag gcccgctggt       780
ggcaggagcg gtcgttcgac cagtctgcca gatagtacgc ttgctggagg atggagtcaa       840
ctgggctact ggttggttcg gtgtccacct ttttgtggta tgtctgctat ctttggcctg       900
tccctgtagt ggggcgcggg tcactgaccc agacacaaat accacaatcc tgaccaattg       960
ctgccagcgt aatcaggtta tctattgttc tccttccact tgcctacacg agcctggttg      1020
tgtgatctgt gcggacgagt gctgggttcc cgccaatccg tacatctcac acccttccaa      1080
ttggactggc acggactcct tcttggctga ccacattgat tttgttatgg gcgctcttgt      1140
gacctgtgac gcccttgaca ttggtgagtt gtgtggtgcg tgtgtattag tcggtgactg      1200
gcttgtcagg cactggctta ttcacataga cctcaatgaa actggtactt gttacctgga      1260
agtgcccact ggaatagatc ctgggttcct agggtttatc gggtggatgg ccggcaaggt      1320
cgaggctgtc atcttcttga ccaaactggc ttcacaagta ccatacgcta ttgcgactat      1380
gtttagcagt gtacactacc tggcggttgg cgctctgatc tactatgcct ctcggggcaa      1440
gtggtatcag ttgctcctag cgcttatgct ttacatagaa gcgacctctg gaaaccccat      1500
cagggtgccc actggatgct caatagctga gttttgctcg cctttgatga taccatgtcc      1560
ttgccactct tatttgagtg agaatgtgtc agaagtcatt tgttacagtc caaagtggac      1620
caggcctatc actctagagt ataacaactc catatcttgg taccccctata caatccctgg      1680 tgcgagggga tgtatggtta aattcaaaaa taacacatgg ggttgctgcc gtattcgcaa      1740
tgtgccatcg tactgcacta tgggcactga tgcagtgtgc aacgacactc gcaacactta      1800
cgaagcatgc ggtgtaacac catggctaac aaccgcatgg cacaacggct cagccctgaa      1860
attggctata ttacaatacc ctgggtctaa agaaatgttt aaacctcata attggatgtc      1920
aggccatttg tattttgagg gatcagatac ccctatagtt tactttttatg accctgtgaa      1980 ttccactctc ctaccaccgg agaggtgggc taggttgccc ggtaccccac ctgtggtacg      2040
tggttcttgg ttacaggttc cgcaagggtt ttacagtgat gtgaaagacc tagccacagg      2100
attgatcacc aaagacaaag cctggaaaaa ttatcaggtc ttatattccg ccacgggtgc      2160
tttgtctctt acgggagtta ccaccaaggc cgtggtgcta attctgttgg ggttgtgtgg      2220
cagcaagtat cttattttag cctacctctg ttacttgtcc ctttgttttg ggcgcgcttc      2280
tggttaccct ttgcgtcctg tgctcccatc ccagtcgtat ctccaagctg gctgggatgt      2340
```

```
tttgtctaaa gctcaagtag ctccttttgc tttgattttc ttcatctgtt gctatctccg    2400
ctgcaggcta cgttatgctg ccctttagg gtttgtgccc atggctgcgg gcttgcccct    2460
aactttcttt gttgcagcag ctgctgccca accagattat gactggtggg tgcgactgct    2520
agtggcaggg ttagttttgt gggccggccg taaccgtggt caccgcatag ctctgcttgt    2580
aggtccttgg cctctggtag cgcttttaac cctcttgcat ttggttacgc ctgcttcagc    2640
ttttgatacc gagataattg gagggctgac aataccacct gtagtagcat tagttgtcat    2700
gtctcgtttt ggcttctttg ctcacttgtt acctcgctgt gctttagtta actcctatct    2760
ttggcaacgt tgggagaatt ggttttggaa cgttacacta agaccggaga ggttttttcct   2820 tgtgctggtt tgtttcccg gtgcgacata tgacgcgctg gtgactttct gtgtgtgtca    2880
cgtagctctt ctatgtttaa catccagtgc agcatcgttc tttgggactg actctagggt    2940
tagggcccat agaatgttgg tgcgtctcgg aaagtgtcat gcttggtatt ctcattatgt    3000
tcttaagttt ttcctcttag tgtttggtga aatggtgtg ttttctata agcacttgca     3060 tggtgatgtc ttgcctaatg attttgcctc gaaactacca ttgcaagagc cattttttccc   3120 ttttgaaggc aaggcaaggg tctataggaa tgaaggaaga cgcttggcgt gtggggacac    3180
ggttgatggt tgcccgttg ttgcgcgtct cggcgacctt gttttcgcag ggttggctat     3240
gccgccagat gggtgggcca ttaccgcacc ttttacgctg cagtgtctct ctgaacgtgg    3300
cacgctgtca gcgatggcag tggtcatgac tggtatagac ccccgaactt ggactggaac    3360
tatcttcaga ttaggatctc tggccactag ctacatggga tttgtttgtg acaacgtgtt    3420
gtatactgct caccatggca gcaaggggcg ccggttggct catcccacag gctctataca    3480
cccaataacc gttgacgcgg ctaatgacca ggacatctat caaccaccat gtggagctgg    3540
gtcccttact cggtgctctt gcggggagac caagggtat ctggtaacac gactggggtc     3600
attggttgag gtcaacaaat ccgatgaccc ttattggtgt gtgtgcgggg cccttcccat    3660
ggctgttgcc aagggttctt caggtgcccc gattctgtgc tcctccgggc atgttattgg    3720
gatgttcacc gctgctagaa attctggcgg ttcagtcagt cagattaggg ttaggccgtt    3780
ggtgtgtgct ggataccatc cccagtacac agcacatgcc actcttgata caaaacctac    3840
tgtgcctaac gagtattcag tgcaaatttt aattgccccc actggcagcg gcaagtcaac    3900
caaattacca ctttcttaca tgcaggagaa gtatgaggtc ttggtcctaa atcccagtgt    3960
ggctacaaca gcatcaatgc caaagtacat gcacgcgacg tacggcgtga atccaaattg    4020
ctattttaat ggcaaatgta ccaacacagg ggcttcactt acgtacagca catatggcat    4080
gtacctgacc ggagcatgtt cccggaacta tgatgtaatc atttgtgacg aatgccatgc    4140
taccgatgca accaccgtgt tgggcattgg aaaggtccta accgaagctc catccaaaaa    4200
tgttaggcta gtggttcttg ccacggctac cccccctgga gtaatcccta caccacatgc    4260
caacataact gagattcaat taaccgatga aggcactatc cccttcatg gaaaaaagat    4320 taaggaggaa aatctgaaga aagggagaca cctatctttt gaggctacca aaaacactg    4380 tgatgagctt gctaacgagt tagctcgaaa gggaataaca gctgtctctt actataggg    4440 atgtgacatc tcaaaatcc ctgagggcga ctgtgtagta gttgccactg atgccttgtg    4500
tacagggtac actggtgact ttgattccgt gtatgactgc agcctcatgg tagaaggcac    4560
atgccatgtt gaccttgacc ctacttcac catgggtgtt cgtgtgtgcg ggtttcagc    4620 aatagttaaa ggccagcgta ggggccgcac aggccgtggg agagctggca tatactacta    4680
```

```
tgtagacggg agttgtaccc cttcgggtat ggttcctgaa tgcaacattg ttgaagcctt    4740
cgacgcagcc aaggcatggt atggtttgtc atcaacagaa gctcaaacta ttctggacac    4800
ctatcgcacc caacctgggt tacctgcgat aggagcaaat ttggacgagt gggctgatct    4860
cttttctatg gtcaaccccg aaccttcatt tgtcaatact gcaaaagaa ctgctgacaa     4920 ttatgttttg ttgactgcag cccaactaca actgtgtcat cagtatggct atgctgctcc    4980
caatgacgca ccacggtggc agggagcccg gcttgggaaa aaaccttgtg gggttctgtg    5040
gcgcttggac ggcgctgacg cctgtcctgg cccagagccc agcgaggtga ccagatacca    5100
aatgtgcttc actgaagtca atacttctgg gacagccgca ctcgctgttg gcgttggagt    5160
ggctatggct tatctagcca ttgacacttt tggcgccact tgtgtgcggc gttgctggtc    5220
tattacatca gtccctaccg gtgctactgt cgccccagtg gttgacgaag aagaaatcgt    5280
ggaggagtgt gcatcattca ttcccttgga ggccatggtt gctgcaattg caagctgaa     5340 gagtacaatc accacaacta gtcctttcac attggaaacc gcccttgaaa aacttaacac    5400 cttcttggg cctcatgcag ctacaatcct tgctatcata gagtattgct gtggtttagt     5460
cactttacct gacaatccct tgcatcatg cgtgtttgct ttcattgcgg gtattactac      5520
cccactacct cacaagatca aaatgttcct gtcattattt ggaggcgcaa ttgcgtccaa    5580
gcttacagac gctagaggcg cactggcgtt catgatggcc ggggctgcgg gaacagctct    5640
tggtacatgg acatcggtgg gttttgtctt tgacatgcta ggcggctatg ctgccgcctc    5700
atccactgct tgcttgacat ttaaatgctt gatgggtgag tggcccacta tggatcagct    5760
tgctggttta gtctactccg cgttcaatcc ggccgcagga gttgtgggcg tcttgtcagc    5820
ttgtgcaatg tttgctttga acagcagg gccagatcac tggcccaaca gacttcttac      5880
tatgcttgct aggagcaaca ctgtatgtaa tgagtacttt attgccactc gtgacatccg    5940
caggaagata ctgggcattc tggaggcatc tacccctgg agtgtcatat cagcttgcat      6000
ccgttggctc cacaccccga cggaggatga ttgcggcctc attgcttggg gtctagagat    6060
ttggcagtat gtgtgcaatt tctttgtgat ttgctttaat gtccttaaag ctggagttca    6120
gagcatggtt aacattcctg ttgtcctttt ctacagctgc cagaaggggt acaagggccc    6180
ctggattgga tcaggtatgc tccaagcacg ctgtccatgc ggtgctgaac tcatcttttc    6240
tgttgagaat ggttttgcaa aactttacaa aggacccaga acttgttcaa attactggag    6300
aggggctgtt ccagtcaacg ctaggctgtg tgggtcggct agaccggacc caactgattg    6360
gactagtctt gtcgtcaatt atggcgttag ggactactgt aaatatgaga aaatgggaga    6420
tcacattttt gttacagcag tatcctctcc aaatgtctgt ttcacccagg tgcccccaac    6480
cttgagagct gcagtggccg tggacggcgt acaggttcag tgttatctag gtgagcccaa    6540
aactccttgg acgacatctg cttgctgtta cggtcctgac ggtaagggta aaactgttaa    6600
gcttcccttc cgcgttgacg tcacacacc tggtgtgcgc atgcaactta atttgcgtga     6660
tgcacttgag acaaatgact gtaattccac aaacaacact cctagtgatg aagccgcagt    6720
gtccgctctt gttttcaaac aggagttgcg gcgtacaaac caattgcttg aggcaatttc    6780
agctggcgtt gacaccacca aactgccagc ccctccatc gaagaggtag tggtaagaaa      6840
gcgccagttc cgggcaagaa ctggttcgct taccttgcct ccccctccga gatccgtccc    6900
aggagtgtca tgtcctgaaa gcctgcaacg aagtgacccg ttagaaggtc cttcaaacct    6960
ccctccttca ccacctgttc tacagttggc catgccgatg ccctgttgg gagcgggtga     7020 gtgtaaccct ttcactgcaa ttggatgtgc aatgaccgaa acaggcggag gccctgatga    7080
```

-continued

```
tttacccagt taccctccca aaaaggaggt ctctgaatgg tcagacgaaa gttggtcgac      7140
ggctacaacc gcttccagct acgttactgg ccccccgtac cctaagatac ggggaaagga      7200
ttccactcag tcagcccccg ccaaacggcc tacaaaaaag aagttgggaa agagtgagtt      7260 tcgtgcagc atgagctaca cctggaccga cgtgattagc ttcaaaactg cttctaaagt       7320
tctgtctgca actcgggcca tcactagtgg tttcctcaaa caaagatcat tggtgtatgt      7380
gactgagccg cgggatgcgg agcttagaaa acaaaaagtc actattaata gacaacctct      7440 gttccccca tcataccaca agcaagtgag attggctaag gaaaaagctt caaaagttgt       7500
cggtgtcatg tgggactatg atgaagtagc agctcacacg ccctctaagt ctgctaagtc      7560
ccacatcact ggccttcggg gcactgatgt tcgttctgga gcagcccgca aggctgttct      7620
ggacttgcag aagtgtgtcg aggcaggtga gataccgagt cattatcggc aaactgtgat      7680
agttccaaag gaggaggtct tcgtgaagac cccccagaaa ccaacaaaga aaccccccaag    7740 gcttatctcg tacccccacc ttgaaatgag atgtgttgag aagatgtact acggtcaggt      7800
tgctcctgac gtagttaaag ctgtcatggg agatgcgtac gggtttgtag atccacgtac      7860
ccgtgtcaag cgtctgttgt cgatgtggtc acccgatgca gtcggagcca catgcgatac      7920
agtgtgtttt gacagtacca tcacacccga ggatatcatg gtggagacag acatctactc      7980
agcagctaaa ctcagtgacc aacaccgagc tggcattcac accattgcga ggcagttata      8040
cgctggagga ccgatgatcg cttatgatgg ccgagagatc ggatatcgta ggtgtaggtc      8100
ttccggcgtc tatactacct caagttccaa cagtttgacc tgctggctga aggtaaatgc      8160
tgcagccgaa caggctggca tgaagaaccc tcgcttcctt atttgcggcg atgattgcac      8220
cgtaatttgg aagagcgccg gagcagatgc agacaaacaa gcaatgcgtg tctttgctag      8280
ctggatgaag gtgatgggtg caccacaaga ttgtgtgcct caacccaaat acagtttgga      8340
agaattaaca tcatgctcat caaatgttac ctctggaatt accaaaagtg gcaagcctta      8400
ctactttctt acaagagatc ctcgtatccc ccttggcagg tgctctgccg agggtctggg      8460
atacaacccc agtgctgcgt ggattgggta tctaatacat cactacccat gtttgtgggt      8520
tagccgtgtg ttggctgtcc atttcatgga gcagatgctc tttgaggaca aacttcccga      8580
gactgtgacc tttgactggt atgggaaaaa ttatacggtg cctgtagaag atctgcccag      8640
catcattgct ggtgtgcacg gtattgaggc tttctcggtg gtgcgctaca ccaacgctga      8700
gatcctcaga gttccccaat cactaacaga catgaccatg cccccctgc gagcctggcg       8760 aaagaaagcc agggcggtcc tcgccagcgc caagaggcgt ggcggagcac acgcaaaatt      8820
ggctcgcttc cttctctggc atgctacatc tagacctcta ccagatttgg ataagacgag      8880
cgtggctcgg tacaccactt tcaattattg tgatgtttac tccccggagg gggatgtgtt      8940
tattacacca cagagaagat tgcagaagtt ccttgtgaag tatttggctg tcattgtttt      9000
tgccctaggg ctcattgctg ttggattagc catcagctga accccaaat tcaaaattaa      9060 ctaacagttt tttttttttt tttttttttt agggcagcgg caacagggga gaccccgggc      9120
ttaacgaccc cgcgatgtg                                                  9139
```

<210> SEQ ID NO 4  
<211> LENGTH: 9711  
<212> TYPE: DNA  
<213> ORGANISM: Hepatitis C virus

<400> SEQUENCE: 4

-continued

| | |
|---|---|
| acccgcccct aatagggcg acactccgcc atgaatcact cccctgtgag gaactactgt | 60 |
| cttcacgcag aaagcgtcta gccatggcgt tagtatgagt gtcgtacagc ctccaggccc | 120 |
| ccccctcccg ggagagccat agtggtctgc ggaaccggtg agtacaccgg aattgccggg | 180 |
| aagactgggt cctttcttgg ataaacccac tctatgcccg gccatttggg cgtgcccccg | 240 |
| caagactgct agccgagtag cgttgggttg cgaaaggcct tgtggtactg cctgataggg | 300 |
| tgcttgcgag tgccccggga ggtctcgtag accgtgcacc atgagcacaa atcctaaacc | 360 |
| tcaaagaaaa accaaaagaa acaccaaccg tcgcccacaa gacgttaagt ttccgggcgg | 420 |
| cggccagatc gttggcggag tatacttgtt gccgcgcagg ggcccaggt tgggtgtgcg | 480 |
| cgcgacaagg aagacttcgg agcggtccca gccacgtgga aggcgccagc ccatccctaa | 540 |
| agatcggcgc tccactggca aatcctgggg aaaaccagga taccccctggc ccctatacgg | 600 |
| gaatgaggga ctcggctggg caggatggct cctgtccccc cgaggttccc gtccctcttg | 660 |
| gggcccccaat gacccccggc ataggtcgcg caacgtgggt aaggtcatcg atacccctaac | 720 |
| gtgcggcttt gccgacctca tggggtacat ccctgtcgtg ggcgccccgc tcggcggcgt | 780 |
| cgccagagct ctcgcgcatg gcgtgagagt cctggaggac ggggttaatt ttgcaacagg | 840 |
| gaacttaccc ggttgctcct tttctatctt cttgctggcc ctgctgtcct gcatcaccac | 900 |
| cccggtctcc gctgccgaag tgaagaacat cagtaccggc tacatggtga ctaacgactg | 960 |
| caccaatgac agcattacct ggcagctcca ggctgctgtc ctccacgtcc ccgggtgcgt | 1020 |
| cccgtgcgag aaagtgggga atgcatctca gtgctggata ccggtctcac cgaatgtggc | 1080 |
| cgtgcagcgg cccggcgccc tcacgcaggg cttgcggacg cacatcgaca tggttgtgat | 1140 |
| gtccgccacg ctctgctctg ccctctacgt gggggacctc tgcggtgggg tgatgctcgc | 1200 |
| agcccaaatg ttcattgtct cgccgcagca ccactggttt gtccaagact gcaattgctc | 1260 |
| catctaccct ggtaccatca ctggacaccg catggcatgg acatgatga tgaactggtc | 1320 |
| gcccacggct accatgatct tggcgtacgc gatgcgtgtc cccgaggtca ttatagacat | 1380 |
| cattagcggg gctcattggg gcgtcatgtt cggcttggcc tacttctcta tgcagggagc | 1440 |
| gtgggcgaaa gtcgttgtca tccttctgtt ggccgccggg gtggacgcgc gcacccatac | 1500 |
| tgttgggggt tctgccgcgc agaccaccgg gcgcctcacc agcttatttg acatgggccc | 1560 |
| caggcagaaa atccagctcg ttaacaccaa tggcagctgg cacatcaacc gcaccgccct | 1620 |
| gaactgcaat gactccttgc acaccggctt tatcgcgtct ctgttctaca cccacagctt | 1680 |
| caactcgtca ggatgtcccg aacgcatgtc cgcctgccgc agtatcgagg ccttccgggt | 1740 |
| gggatggggc gccttgcaat atgaggataa tgtcaccaat ccagaggata tgagacccta | 1800 |
| ttgctggcac tacccaccaa ggcagtgtgg cgtggtctcc gcgaagactg tgtgtggccc | 1860 |
| agtgtactgt ttcacccccca gcccagtggt agtgggcacg accgacaggc ttggagcgcc | 1920 |
| cacttacacg tgggggagga atgagacaga tgtcttccta ttgaacagca ctcgaccacc | 1980 |
| gctggggtca tggttcggct gcacgtggat gaactcttct ggctacacca agacttgcgg | 2040 |
| cgcaccaccc tgccgtacta gagctgactt caacgccagc acggacctgt tgtgccccac | 2100 |
| ggactgttttt aggaagcatc ctgataccac ttacctcaaa tgcggctctg ggccctggct | 2160 |
| cacgccaagg tgcctgatcg actaccccta caggctctgg cattaccct gcacagttaa | 2220 |
| ctataccatc ttcaaaataa ggatgtatgt gggagggtt gagcacaggc tcacggctgc | 2280 |
| atgcaatttc actcgtgggg atcgttcaa cttggaggac agagacagaa gtcaactgtc | 2340 |
| tcctttgttg cactccacca cggaatgggc catttttacct tgctcttact cggacctgcc | 2400 |

```
cgccttgtcg actggtcttc tccacctcca ccaaaacatc gtggacgtac aattcatgta    2460
tggcctatca cctgccctca caaaatacat cgtccgatgg gagtgggtaa tactcttatt    2520
cctgctctta gcggacgcca gggtttgcgc ctgcttatgg atgctcatct tgttgggcca    2580
ggccgaagca gcactagaga agctggtcat cttgcacgct gcgagcgcag ctagctgcaa    2640
tggcttccta tattttgtca tcttttttcgt ggctgcttgg tacatcaagg gtcgggtagt    2700 cccccttagct acctattccc tcactggcct gtggtccttt agcctactgc tcctagcatt    2760
gccccaacag gcttatgctt atgacgcatc tgtgcatggc cagataggag cggctctgct    2820
ggtaatgatc actctctttta ctctcacccc cgggtataag acccttctca gccggttttt    2880
gtggtggttg tgctatcttc tgaccctggg ggaagctatg gtccaggagt gggcaccacc    2940
tatgcaggtg cgcggtggcc gtgatggcat catatgggcc gtcgccatat tctacccagg    3000
tgtggtgttt gacataacca agtggctctt ggcggtgctt gggcctgctt acctcctaaa    3060
aggtgctttg acgcgcgtgc cgtacttcgt cagggctcac gctctactga ggatgtgcac    3120
catggcaagg catctcgcgg ggggcaggta cgtccagatg cgctactag cccttggcag    3180 gtggactggc acttacatct atgaccacct caccccctatg tcggattggg ctgctagtgg    3240
cctgcgggac ctggcggtcg ccgttgagcc tatcatcttc agtccgatgg agaagaaagt    3300
cattgtctgg ggagcggaga cagctgcttg tggggacatt ttacacggac ttcccgtgtc    3360
cgcccgactt ggtcgggagg tcctccttgg cccagctgat ggctatacct ccaaggggtg    3420
gagtcttctc gcccccatca ctgcttacgc ccagcagaca cgtggccttt tgggcaccat    3480
agtggtgagc atgacggggc gcgacaagac agaacaggct ggggaaattc aggtcctgtc    3540
cacagtcact cagtccttcc tcggaacatc catctcgggg gttttgtgga ctgtctacca    3600
tggagctggc aacaagactc tggccggctc acggggtccg gtcacgcaga tgtactccag    3660
tgctgagggg gacttagtag ggtggcccag ccccctggg actaaatctt tggagccgtg    3720
cacgtgtgga gcggtcgacc tgtacctggt cacgcggaac gctgatgtca tcccggctcg    3780
aagacgcggg gacaaacggg gagcgctact ctccccgaga cctctttcca ccttgaaggg    3840
gtcctcagga ggcccggtgc tatgcccag gggccacgct gtcggagtct tccgggcagc    3900
tgtgtgctct cggggcgtgg ctaagtccat agatttcatc cccgttgaga cactcgacat    3960
cgtcacgcgg tcccccacct ttagtgacaa cagcacacca cctgctgtgc cccagaccta    4020
tcaggtcggg tacttgcatg ccccgactgg cagtggaaag agcaccaaag ttcctgtcgc    4080
atatgctgct caggggtata aagtgctagt gcttaatccc tcagtggctg ccaccctggg    4140
gtttggggcg tacttgtcta aggcacatgg catcaatccc aacattagga ctggagtcag    4200
gactgtgacg accggggcgc ccatcacgta ctccacatat ggcaaattcc tcgccgatgg    4260
gggctgtgcg gcggcgcct acgacatcat catatgtgat gaatgccatg ccgtggactc    4320
taccaccatc cttggcatcg aacagtcct tgatcaagca gagacagctg ggtcagact    4380 aactgtgctg gctacagcta cgccccctgg gtcagtgaca accccccacc caacataga    4440 ggaggtggcc cttgggcagg agggcgagat cccctctat ggaggcga ttccctgtc    4500 ttacatcaag gaggaagac atctgatctt ctgccattca aagaaaaagt gtgacgagct    4560
cgcggcggcc cttcggggta tgggcttgaa ctcagtggca tactacagag ggttggacgt    4620
ctccgtaata ccaactcagg gagacgtagt ggtcgtcgcc accgacgccc tcatgacagg    4680
gtatactggg gactttgact ccgtgatcga ctgcaacgta gcggtcactc aagttgtaga    4740
```

```
cttcagttta gaccccacat tcaccataac cacacagatt gtccctcaag acgctgtctc    4800
acgtagccag cgccggggtc gcacgggtag gggaagactg ggcatttata ggtatgtttc    4860
cactggtgag cgagcctcag gaatgtttga cagtgtagtg ctctgtgagt gctacgacgc    4920
aggggccgca tggtatgagc tcacaccatc ggagaccacc gtcaggctca gggcgtattt    4980
caacacgccc ggtttgcctg tgtgccaaga ccatcttgag ttttgggagg cagttttcac    5040
cggcctcaca cacatagatg cccacttcct ttcccaaaca aagcaatcgg gggaaaattt    5100
cgcatactta acagcctacc aggctacagt gtgcgctagg gccaaagccc ccccccgtc     5160
ctgggacgtc atgtggaagt gtttgactcg actcaagccc acactcgtgg gccccacacc    5220
tctcctgtac cgcttgggct ctgttaccaa cgaggtcacc ctcacacatc ccgtgacgaa    5280
atacatcgcc acctgcatgc aagccgacct tgaggtcatg accagcacat gggtcttggc    5340
aggggagtc ttggcggccg tcgccgcgta ttgcctggcg accgggtgtg tttgcatcat     5400
cggccgcttg cacattaacc agcgagccgt cgttgcgccg gacaaggagg tcctctatga    5460
ggcttttgat gagatggagg aatgtgcctc tagggcggct ctcattgaag aggggcagcg    5520
gatagccgag atgctgaagt ccaagatcca aggcttattg cagcaagctt ccaaacaagc    5580
tcaagacata caacccactg tgcaggcttc atggcccaag gtagaacaat tctgggccaa    5640
acacatgtgg aacttcatta gcggcatcca atacctcgca ggactatcaa cactgccagg    5700
gaaccctgca gtagcttcca tgatggcgtt cagtgccgcc ctcaccagtc cgctgtcaac    5760
aagcaccact atccttctca acattttggg gggctggcta gcatcccaaa ttgcaccacc    5820
cgcggggggcc actggcttcg ttgtcagtgg cctagtggga gctgccgtag gcagtatagg    5880
cttaggtaag gtgctagtgg acatcctggc agggtatggt gcgggcattt cgggggctct    5940
cgtcgcattc aagatcatgt ctggcgagaa gccctccatg gaggatgtcg tcaacttgct    6000
gcctggaatt ctgtctccgg gtgccttggt agtgggagtc atctgcgcgg ccattctgcg    6060
ccgacacgtg ggaccggggg aaggcgccgt ccaatggatg aatagactca ttgcctttgc    6120
ttccagagga aatcacgtcg cccccaccca ctacgtgacg gagtcggatg cgtcgcagcg    6180
tgtgacccaa ctacttggct cccttaccat aaccagcctg ctcagaagac tccacaactg    6240
gattactgag gactgcccca tcccatgcgg cggctcgtgg ctccgcgatg tgtgggactg    6300
ggtttgcacc atcctaacag actttaaaaa ttggctgacc tccaaattat tcccaaagat    6360
gcccggcctc ccctttgtct cctgtcaaaa ggggtacaag ggcgtgtggg ccggcactgg    6420
catcatgacc acacggtgtc cttgcggcgc caatatctct ggcaatgtcc gcttgggctc    6480
catgagaatc acgggcccta agacctgcat gaatatctgg caggggacct ttcctatcaa    6540
ttgttacacg gagggccagt gcgtgccgaa acccgcgcca aactttaagg tcgccatctg    6600
gagggtggcg gcctcagagt acgcggaggt gacgcagcac gggtcatacc actacataac    6660
aggactcacc actgataact tgaaagtccc ctgccaacta ccctctcccg agttcttttc    6720
ctgggtggac ggagtgcaga tccataggtt tgccccccaca ccgaagccgt ttttccggga   6780
tgaggtctcg ttctgcgttg gcttaattc atttgtcgtc gggtcccagc ttccttgcga    6840
ccctgaaccc gacacagacg tattgatgtc catgctaaca gatccatctc atatcacggc    6900
ggagactgca gcgcggcgtt tagcgcgggg gtcaccccca tccgaggcaa gctcctcggc    6960
gagccagcta tcggcaccat cgctgcgagc cacctgcacc acccacggca agcctatga    7020
tgtggacatg gtggatgcta acctgttcat gggggggcgat gtgactcgga tagagtctgg    7080
gtccaaagtg gtcgttctgg actctctcga cccaatggtc gaagaaagga gcgaccttga    7140
```

```
gccttcgata ccatcagaat acatgctccc caagaagagg ttcccaccag ctttaccggc    7200
ctgggcacgg cctgattaca acccaccgct tgtggaatcg tggaaaaggc cagattacca    7260
accggccact gttgcgggct gtgctctccc tcctcctagg aaaacccga cgcctccccc     7320 aaggaggcgc cggacagtgg gcctaagtga ggactccata ggagatgccc ttcaacagct    7380
ggccattaag tcctttggcc agcccccccc aagcggcgat tcaggccttt ccacggggc     7440 gggcgctgcc gattccggca gtcagacgcc tcctgatgag ttggcccttt cggagacagg    7500
ttccatctct tccatgcccc ccctcgaggg ggagcttgga gatccagacc tggagcctga    7560
gcaggtagag ccccaacccc cccccaggg ggggtggca gctcccggct cggactcggg      7620
gtcctggtct acttgctccg aggaggacga ctccgtcgtg tgctgctcca tgtcatactc    7680
ctggaccggg gctctaataa ctccttgtag tcccgaagag gagaagttac cgattaaccc    7740
cttgagcaac tccctgttgc gatatcacaa caaggtgtac tgtaccacaa caaagagcgc    7800
ctcactaagg gctaaaaagg taacttttga taggatgcaa gtgctcgact cctactacga    7860
ctcagtctta aaggacatta agctagcggc ctccaaggtc accgcaaggc tcctcaccat    7920
ggaggaggct tgccagttaa ccccacccca ttctgcaaga tctaaatatg gtttggggc     7980 taaggaggtc cgcagcttgt ccgggagggc cgttaaccac atcaagtccg tgtggaagga    8040
cctcctggag gactcagaaa caccaattcc cacaaccatt atggccaaaa atgaggtgtt    8100
ctgcgtggac cccaccaagg ggggcaagaa agcagctcgc cttatcgttt accctgacct    8160
cggcgtcagg gtctgcgaga agatggccct ttatgacatt acacaaaaac ttcctcaggc    8220
ggtgatgggg gcttcttatg gattccagta ttccccgct cagcgggtag agtttctctt     8280
gaaagcatgg gcgaaaaga aggaccctat gggttttttcg tatgatacc gatgctttga     8340 ctcaaccgtc actgagagag acatcaggac tgaggagtcc atatatcggg cctgctcctt    8400
gcccgaggag gcccacactg ccatacactc gctaactgag agactttacg tgggagggcc    8460
tatgttcaac agcaagggcc aaacctgcgg gtacaggcgt tgccgcgcca gcgggtgct    8520 caccactagc atgggaaaca ccatcacatg ctacgtgaaa gccttagcgg cttgtaaagc    8580
tgcagggata atcgcgccca caatgctggt atgcggcgat gacttggttg tcatctcaga    8640
aagccagggg accgaggagg acgagcggaa cctgagagcc ttcacggagg ctatgaccag    8700
gtattctgcc cctcctggtg acccccccag accggagtat gatctggagc tgataacatc    8760
ttgctcctca aatgtgtctg tggcgctggg cccacaaggc cgccgcagat actacctgac    8820
cagagaccct accactccaa tcgcccgggc tgcctgggaa acagttagac actcccctgt    8880
caattcatgg ctgggaaaca tcatccagta cgccccgacc atatgggctc gcatggtcct    8940
gatgacacac ttcttctcca ttctcatggc tcaagacacg ctggaccaga acctcaactt    9000
tgagatgtac ggagcggtgt actccgtgag tcccttggac ctcccagcta taattgaaag    9060
gttacatggg cttgacgctt tttctctgca cacatacact ccccacgaac tgacacgggt    9120
ggcttcagcc ctcagaaaac ttggggcgcg acccctcaga gcgtggaaga gccgggcacg    9180
tgcagtcagg gcgtccctca tctcccgtgg ggggagagcg gccgtttgcg gtcgatatct    9240
cttcaattgg gcggtgaaga ccaagctcaa actcactcca ttgccggaag cgcgcctcct    9300
ggatttatcc agctggttca ccgtcggcgc cggcgggggc gacatttatc acagcgtgtc    9360
gcgtgcccga ccccgcttat tgctctttgg cctactccta cttttgtag ggtaggcct     9420 tttcctactc cccgctcggt agagcggcac acattagcta cactccatag ctaactgtcc    9480
```

-continued

```
ctttttttttt tttttttttt tttttttttt tttttttttt tttttttttt tttttttttt    9540
tttttttttt tttttttttt ttttttcttttt tttctctttt ccttctttct taccttattt    9600
tactttcttt cctggtggct ccatcttagc cctagtcacg gctagctgtg aaaggtccgt    9660
gagccgcatg actgcagaga gtgccgtaac tggtctctct gcagatcatg t             9711
```

<210> SEQ ID NO 5
<211> LENGTH: 3033
<212> TYPE: PRT
<213> ORGANISM: Hepatitis C virus

<400> SEQUENCE: 5

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
                 20                  25                  30

Gly Val Tyr Leu Leu Pro Arg Arg Gly Pro Arg Leu Gly Val Arg Ala
             35                  40                  45

Thr Arg Lys Thr Ser Glu Arg Ser Gln Pro Arg Gly Arg Arg Gln Pro
         50                  55                  60

Ile Pro Lys Asp Arg Arg Ser Thr Gly Lys Ser Trp Gly Lys Pro Gly
 65                  70                  75                  80

Tyr Pro Trp Pro Leu Tyr Gly Asn Glu Gly Leu Gly Trp Ala Gly Trp
                 85                  90                  95

Leu Leu Ser Pro Arg Gly Ser Arg Pro Ser Trp Gly Pro Asn Asp Pro
                100                 105                 110

Arg His Arg Ser Arg Asn Val Gly Lys Val Ile Asp Thr Leu Thr Cys
            115                 120                 125

Gly Phe Ala Asp Leu Met Gly Tyr Ile Pro Val Val Gly Ala Pro Leu
        130                 135                 140

Gly Gly Val Ala Arg Ala Leu Ala His Gly Val Arg Val Leu Glu Asp
145                 150                 155                 160

Gly Val Asn Phe Ala Thr Gly Asn Leu Pro Gly Cys Ser Phe Ser Ile
                165                 170                 175

Phe Leu Leu Ala Leu Leu Ser Cys Ile Thr Thr Pro Val Ser Ala Ala
                180                 185                 190

Glu Val Lys Asn Ile Ser Thr Gly Tyr Met Val Thr Asn Asp Cys Thr
            195                 200                 205

Asn Asp Ser Ile Thr Trp Gln Leu Gln Ala Ala Val Leu His Val Pro
        210                 215                 220

Gly Cys Val Pro Cys Glu Lys Val Gly Asn Ala Ser Gln Cys Trp Ile
225                 230                 235                 240

Pro Val Ser Pro Asn Val Ala Val Gln Arg Pro Gly Ala Leu Thr Gln
                245                 250                 255

Gly Leu Arg Thr His Ile Asp Met Val Val Met Ser Ala Thr Leu Cys
            260                 265                 270

Ser Ala Leu Tyr Val Gly Asp Leu Cys Gly Gly Val Met Leu Ala Ala
        275                 280                 285

Gln Met Phe Ile Val Ser Pro Gln His His Trp Phe Val Gln Asp Cys
    290                 295                 300

Asn Cys Ser Ile Tyr Pro Gly Thr Ile Thr Gly His Arg Met Ala Trp
305                 310                 315                 320

Asp Met Met Met Asn Trp Ser Pro Thr Ala Thr Met Ile Leu Ala Tyr
                325                 330                 335
```

```
Ala Met Arg Val Pro Glu Val Ile Ile Asp Ile Ile Ser Gly Ala His
            340                 345                 350
Trp Gly Val Met Phe Gly Leu Ala Tyr Phe Ser Met Gln Gly Ala Trp
            355                 360                 365
Ala Lys Val Val Val Ile Leu Leu Leu Ala Ala Gly Val Asp Ala Arg
            370                 375                 380
Thr His Thr Val Gly Gly Ser Ala Ala Gln Thr Thr Gly Arg Leu Thr
385                 390                 395                 400
Ser Leu Phe Asp Met Gly Pro Arg Gln Lys Ile Gln Leu Val Asn Thr
                405                 410                 415
Asn Gly Ser Trp His Ile Asn Arg Thr Ala Leu Asn Cys Asn Asp Ser
                420                 425                 430
Leu His Thr Gly Phe Ile Ala Ser Leu Phe Tyr Thr His Ser Phe Asn
                435                 440                 445
Ser Ser Gly Cys Pro Glu Arg Met Ser Ala Cys Arg Ser Ile Glu Ala
            450                 455                 460
Phe Arg Val Gly Trp Gly Ala Leu Gln Tyr Glu Asp Asn Val Thr Asn
465                 470                 475                 480
Pro Glu Asp Met Arg Pro Tyr Cys Trp His Tyr Pro Pro Arg Gln Cys
                485                 490                 495
Gly Val Val Ser Ala Lys Thr Val Cys Gly Pro Val Tyr Cys Phe Thr
            500                 505                 510
Pro Ser Pro Val Val Val Gly Thr Thr Asp Arg Leu Gly Ala Pro Thr
            515                 520                 525
Tyr Thr Trp Gly Glu Asn Glu Thr Asp Val Phe Leu Leu Asn Ser Thr
            530                 535                 540
Arg Pro Pro Leu Gly Ser Trp Phe Gly Cys Thr Trp Met Asn Ser Ser
545                 550                 555                 560
Gly Tyr Thr Lys Thr Cys Gly Ala Pro Pro Cys Arg Thr Arg Ala Asp
                565                 570                 575
Phe Asn Ala Ser Thr Asp Leu Leu Cys Pro Thr Asp Cys Phe Arg Lys
                580                 585                 590
His Pro Asp Thr Thr Tyr Leu Lys Cys Gly Ser Gly Pro Trp Leu Thr
                595                 600                 605
Pro Arg Cys Leu Ile Asp Tyr Pro Tyr Arg Leu Trp His Tyr Pro Cys
            610                 615                 620
Thr Val Asn Tyr Thr Ile Phe Lys Ile Arg Met Tyr Val Gly Gly Val
625                 630                 635                 640
Glu His Arg Leu Thr Ala Ala Cys Asn Phe Thr Arg Gly Asp Arg Cys
                645                 650                 655
Asn Leu Glu Asp Arg Asp Arg Ser Gln Leu Ser Pro Leu Leu His Ser
                660                 665                 670
Thr Thr Glu Trp Ala Ile Leu Pro Cys Ser Tyr Ser Asp Leu Pro Ala
            675                 680                 685
Leu Ser Thr Gly Leu Leu His Leu His Gln Asn Ile Val Asp Val Gln
            690                 695                 700
Phe Met Tyr Gly Leu Ser Pro Ala Leu Thr Lys Tyr Ile Val Arg Trp
705                 710                 715                 720
Glu Trp Val Ile Leu Leu Phe Leu Leu Leu Ala Asp Ala Arg Val Cys
                725                 730                 735
Ala Cys Leu Trp Met Leu Ile Leu Leu Gly Gln Ala Glu Ala Ala Leu
                740                 745                 750
Glu Lys Leu Val Ile Leu His Ala Ala Ser Ala Ala Ser Cys Asn Gly
```

-continued

```
                755                 760                 765
Phe Leu Tyr Phe Val Ile Phe Val Ala Ala Trp Tyr Ile Lys Gly
770                 775                 780

Arg Val Val Pro Leu Ala Thr Tyr Ser Leu Thr Gly Leu Trp Ser Phe
785                 790                 795                 800

Ser Leu Leu Leu Ala Leu Pro Gln Gln Ala Tyr Ala Tyr Asp Ala
                805                 810                 815

Ser Val His Gly Gln Ile Gly Ala Ala Leu Leu Val Met Ile Thr Leu
                820                 825                 830

Phe Thr Leu Thr Pro Gly Tyr Lys Thr Leu Leu Ser Arg Phe Leu Trp
                835                 840                 845

Trp Leu Cys Tyr Leu Leu Thr Leu Gly Glu Ala Met Val Gln Glu Trp
850                 855                 860

Ala Pro Pro Met Gln Val Arg Gly Arg Asp Gly Ile Ile Trp Ala
865                 870                 875                 880

Val Ala Ile Phe Tyr Pro Gly Val Val Phe Asp Ile Thr Lys Trp Leu
                885                 890                 895

Leu Ala Val Leu Gly Pro Ala Tyr Leu Leu Lys Gly Ala Leu Thr Arg
                900                 905                 910

Val Pro Tyr Phe Val Arg Ala His Ala Leu Leu Arg Met Cys Thr Met
                915                 920                 925

Ala Arg His Leu Ala Gly Gly Arg Tyr Val Gln Met Ala Leu Leu Ala
930                 935                 940

Leu Gly Arg Trp Thr Gly Thr Tyr Ile Tyr Asp His Leu Thr Pro Met
945                 950                 955                 960

Ser Asp Trp Ala Ala Ser Gly Leu Arg Asp Leu Ala Val Ala Val Glu
                965                 970                 975

Pro Ile Ile Phe Ser Pro Met Glu Lys Lys Val Ile Val Trp Gly Ala
                980                 985                 990

Glu Thr Ala Ala Cys Gly Asp Ile Leu His Gly Leu Pro Val Ser Ala
                995                 1000                1005

Arg Leu Gly Arg Glu Val Leu Leu Gly Pro Ala Asp Gly Tyr Thr Ser
                1010                1015                1020

Lys Gly Trp Ser Leu Leu Ala Pro Ile Thr Ala Tyr Ala Gln Gln Thr
1025                1030                1035                1040

Arg Gly Leu Leu Gly Thr Ile Val Val Ser Met Thr Gly Arg Asp Lys
                1045                1050                1055

Thr Glu Gln Ala Gly Glu Ile Gln Val Leu Ser Thr Val Thr Gln Ser
                1060                1065                1070

Phe Leu Gly Thr Ser Ile Ser Gly Val Leu Trp Thr Val Tyr His Gly
                1075                1080                1085

Ala Gly Asn Lys Thr Leu Ala Gly Ser Arg Gly Pro Val Thr Gln Met
                1090                1095                1100

Tyr Ser Ser Ala Glu Gly Asp Leu Val Gly Trp Pro Ser Pro Pro Gly
1105                1110                1115                1120

Thr Lys Ser Leu Glu Pro Cys Thr Cys Gly Ala Val Asp Leu Tyr Leu
                1125                1130                1135

Val Thr Arg Asn Ala Asp Val Ile Pro Ala Arg Arg Gly Asp Lys
                1140                1145                1150

Arg Gly Ala Leu Leu Ser Pro Arg Pro Leu Ser Thr Leu Lys Gly Ser
                1155                1160                1165

Ser Gly Gly Pro Val Leu Cys Pro Arg Gly His Ala Val Gly Val Phe
                1170                1175                1180
```

-continued

```
Arg Ala Ala Val Cys Ser Arg Gly Val Ala Lys Ser Ile Asp Phe Ile
1185                1190                1195                1200

Pro Val Glu Thr Leu Asp Ile Val Thr Arg Ser Pro Thr Phe Ser Asp
            1205                1210                1215

Asn Ser Thr Pro Pro Ala Val Pro Gln Thr Tyr Gln Val Gly Tyr Leu
            1220                1225                1230

His Ala Pro Thr Gly Ser Gly Lys Ser Thr Lys Val Pro Val Ala Tyr
            1235                1240                1245

Ala Ala Gln Gly Tyr Lys Val Leu Val Leu Asn Pro Ser Val Ala Ala
            1250                1255                1260

Thr Leu Gly Phe Gly Ala Tyr Leu Ser Lys Ala His Gly Ile Asn Pro
1265                1270                1275                1280

Asn Ile Arg Thr Gly Val Arg Thr Val Thr Thr Gly Ala Pro Ile Thr
            1285                1290                1295

Tyr Ser Thr Tyr Gly Lys Phe Leu Ala Asp Gly Gly Cys Ala Gly Gly
            1300                1305                1310

Ala Tyr Asp Ile Ile Cys Asp Glu Cys His Ala Val Asp Ser Thr
            1315                1320                1325

Thr Ile Leu Gly Ile Gly Thr Val Leu Asp Gln Ala Glu Thr Ala Gly
            1330                1335                1340

Val Arg Leu Thr Val Leu Ala Thr Ala Thr Pro Pro Gly Ser Val Thr
1345                1350                1355                1360

Thr Pro His Pro Asn Ile Glu Glu Val Ala Leu Gly Gln Gly Glu
            1365                1370                1375

Ile Pro Phe Tyr Gly Arg Ala Ile Pro Leu Ser Tyr Ile Lys Gly Gly
            1380                1385                1390

Arg His Leu Ile Phe Cys His Ser Lys Lys Cys Asp Glu Leu Ala
            1395                1400                1405

Ala Ala Leu Arg Gly Met Gly Leu Asn Ser Val Ala Tyr Tyr Arg Gly
            1410                1415                1420

Leu Asp Val Ser Val Ile Pro Thr Gln Gly Asp Val Val Val Ala
1425                1430                1435                1440

Thr Asp Ala Leu Met Thr Gly Tyr Thr Gly Asp Phe Asp Ser Val Ile
            1445                1450                1455

Asp Cys Asn Val Ala Val Thr Gln Val Val Asp Phe Ser Leu Asp Pro
            1460                1465                1470

Thr Phe Thr Ile Thr Thr Gln Ile Val Pro Gln Asp Ala Val Ser Arg
            1475                1480                1485

Ser Gln Arg Arg Gly Arg Thr Gly Arg Gly Arg Leu Gly Ile Tyr Arg
            1490                1495                1500

Tyr Val Ser Thr Gly Glu Arg Ala Ser Gly Met Phe Asp Ser Val Val
1505                1510                1515                1520

Leu Cys Glu Cys Tyr Asp Ala Gly Ala Ala Trp Tyr Glu Leu Thr Pro
            1525                1530                1535

Ser Glu Thr Thr Val Arg Leu Arg Ala Tyr Phe Asn Thr Pro Gly Leu
            1540                1545                1550

Pro Val Cys Gln Asp His Leu Glu Phe Trp Glu Ala Val Phe Thr Gly
            1555                1560                1565

Leu Thr His Ile Asp Ala His Phe Leu Ser Gln Thr Lys Gln Ser Gly
            1570                1575                1580

Glu Asn Phe Ala Tyr Leu Thr Ala Tyr Gln Ala Thr Val Cys Ala Arg
1585                1590                1595                1600
```

-continued

Ala Lys Ala Pro Pro Ser Trp Asp Val Met Trp Lys Cys Leu Thr
        1605                1610                1615

Arg Leu Lys Pro Thr Leu Val Gly Pro Thr Pro Leu Leu Tyr Arg Leu
            1620                1625                1630

Gly Ser Val Thr Asn Glu Val Thr Leu Thr His Pro Val Thr Lys Tyr
        1635                1640                1645

Ile Ala Thr Cys Met Gln Ala Asp Leu Glu Val Met Thr Ser Thr Trp
        1650                1655                1660

Val Leu Ala Gly Gly Val Leu Ala Ala Val Ala Ala Tyr Cys Leu Ala
1665                1670                1675                1680

Thr Gly Cys Val Cys Ile Ile Gly Arg Leu His Ile Asn Gln Arg Ala
            1685                1690                1695

Val Val Ala Pro Asp Lys Glu Val Leu Tyr Glu Ala Phe Asp Glu Met
            1700                1705                1710

Glu Glu Cys Ala Ser Arg Ala Ala Leu Ile Glu Glu Gly Gln Arg Ile
            1715                1720                1725

Ala Glu Met Leu Lys Ser Lys Ile Gln Gly Leu Leu Gln Gln Ala Ser
            1730                1735                1740

Lys Gln Ala Gln Asp Ile Gln Pro Thr Val Gln Ala Ser Trp Pro Lys
1745                1750                1755                1760

Val Glu Gln Phe Trp Ala Lys His Met Trp Asn Phe Ile Ser Gly Ile
            1765                1770                1775

Gln Tyr Leu Ala Gly Leu Ser Thr Leu Pro Gly Asn Pro Ala Val Ala
            1780                1785                1790

Ser Met Met Ala Phe Ser Ala Ala Leu Thr Ser Pro Leu Ser Thr Ser
            1795                1800                1805

Thr Thr Ile Leu Leu Asn Ile Leu Gly Gly Trp Leu Ala Ser Gln Ile
            1810                1815                1820

Ala Pro Pro Ala Gly Ala Thr Gly Phe Val Val Ser Gly Leu Val Gly
1825                1830                1835                1840

Ala Ala Val Gly Ser Ile Gly Leu Gly Lys Val Leu Val Asp Ile Leu
            1845                1850                1855

Ala Gly Tyr Gly Ala Gly Ile Ser Gly Ala Leu Val Ala Phe Lys Ile
            1860                1865                1870

Met Ser Gly Glu Lys Pro Ser Met Glu Asp Val Val Asn Leu Leu Pro
            1875                1880                1885

Gly Ile Leu Ser Pro Gly Ala Leu Val Val Gly Val Ile Cys Ala Ala
            1890                1895                1900

Ile Leu Arg Arg His Val Gly Pro Gly Glu Gly Ala Val Gln Trp Met
1905                1910                1915                1920

Asn Arg Leu Ile Ala Phe Ala Ser Arg Gly Asn His Val Ala Pro Thr
            1925                1930                1935

His Tyr Val Thr Glu Ser Asp Ala Ser Gln Arg Val Thr Gln Leu Leu
            1940                1945                1950

Gly Ser Leu Thr Ile Thr Ser Leu Leu Arg Arg Leu His Asn Trp Ile
            1955                1960                1965

Thr Glu Asp Cys Pro Ile Pro Cys Gly Gly Ser Trp Leu Arg Asp Val
            1970                1975                1980

Trp Asp Trp Val Cys Thr Ile Leu Thr Asp Phe Lys Asn Trp Leu Thr
1985                1990                1995                2000

Ser Lys Leu Phe Pro Lys Met Pro Gly Leu Pro Phe Val Ser Cys Gln
            2005                2010                2015

Lys Gly Tyr Lys Gly Val Trp Ala Gly Thr Gly Ile Met Thr Thr Arg

-continued

```
                2020                2025                2030
Cys Pro Cys Gly Ala Asn Ile Ser Gly Asn Val Arg Leu Gly Ser Met
        2035                2040                2045

Arg Ile Thr Gly Pro Lys Thr Cys Met Asn Ile Trp Gln Gly Thr Phe
        2050                2055                2060

Pro Ile Asn Cys Tyr Thr Glu Gly Gln Cys Val Pro Lys Pro Ala Pro
2065                2070                2075                2080

Asn Phe Lys Val Ala Ile Trp Arg Val Ala Ala Ser Glu Tyr Ala Glu
            2085                2090                2095

Val Thr Gln His Gly Ser Tyr His Tyr Ile Thr Gly Leu Thr Thr Asp
                2100                2105                2110

Asn Leu Lys Val Pro Cys Gln Leu Pro Ser Pro Glu Phe Phe Ser Trp
            2115                2120                2125

Val Asp Gly Val Gln Ile His Arg Phe Ala Pro Thr Pro Lys Pro Phe
        2130                2135                2140

Phe Arg Asp Glu Val Ser Phe Cys Val Gly Leu Asn Ser Phe Val Val
2145                2150                2155                2160

Gly Ser Gln Leu Pro Cys Asp Pro Glu Pro Asp Thr Asp Val Leu Met
            2165                2170                2175

Ser Met Leu Thr Asp Pro Ser His Ile Thr Ala Glu Thr Ala Ala Arg
        2180                2185                2190

Arg Leu Ala Arg Gly Ser Pro Ser Glu Ala Ser Ser Ser Ala Ser
        2195                2200                2205

Gln Leu Ser Ala Pro Ser Leu Arg Ala Thr Cys Thr Thr His Gly Lys
        2210                2215                2220

Ala Tyr Asp Val Asp Met Val Asp Ala Asn Leu Phe Met Gly Gly Asp
2225                2230                2235                2240

Val Thr Arg Ile Glu Ser Gly Ser Lys Val Val Leu Asp Ser Leu
            2245                2250                2255

Asp Pro Met Val Glu Glu Arg Ser Asp Leu Glu Pro Ser Ile Pro Ser
            2260                2265                2270

Glu Tyr Met Leu Pro Lys Lys Arg Phe Pro Pro Ala Leu Pro Ala Trp
        2275                2280                2285

Ala Arg Pro Asp Tyr Asn Pro Pro Leu Val Glu Ser Trp Lys Arg Pro
        2290                2295                2300

Asp Tyr Gln Pro Ala Thr Val Ala Gly Cys Ala Leu Pro Pro Pro Arg
2305                2310                2315                2320

Lys Thr Pro Thr Pro Pro Arg Arg Arg Arg Thr Val Gly Leu Ser
            2325                2330                2335

Glu Asp Ser Ile Gly Asp Ala Leu Gln Gln Leu Ala Ile Lys Ser Phe
        2340                2345                2350

Gly Gln Pro Pro Pro Ser Gly Asp Ser Gly Leu Ser Thr Gly Ala Gly
        2355                2360                2365

Ala Ala Asp Ser Gly Ser Gln Thr Pro Pro Asp Glu Leu Ala Leu Ser
            2370                2375                2380

Glu Thr Gly Ser Ile Ser Ser Met Pro Pro Leu Glu Gly Glu Leu Gly
2385                2390                2395                2400

Asp Pro Asp Leu Glu Pro Glu Gln Val Glu Pro Gln Pro Pro Gln
                2405                2410                2415

Gly Gly Val Ala Ala Pro Gly Ser Asp Ser Gly Ser Trp Ser Thr Cys
            2420                2425                2430

Ser Glu Glu Asp Asp Ser Val Val Cys Cys Ser Met Ser Tyr Ser Trp
            2435                2440                2445
```

```
Thr Gly Ala Leu Ile Thr Pro Cys Ser Pro Glu Glu Lys Leu Pro
    2450                2455                2460

Ile Asn Pro Leu Ser Asn Ser Leu Leu Arg Tyr His Asn Lys Val Tyr
2465                2470                2475                2480

Cys Thr Thr Thr Lys Ser Ala Ser Leu Arg Ala Lys Lys Val Thr Phe
                2485                2490                2495

Asp Arg Met Gln Val Leu Asp Ser Tyr Tyr Asp Ser Val Leu Lys Asp
            2500                2505                2510

Ile Lys Leu Ala Ala Ser Lys Val Thr Ala Arg Leu Leu Thr Met Glu
        2515                2520                2525

Glu Ala Cys Gln Leu Thr Pro Pro His Ser Ala Arg Ser Lys Tyr Gly
    2530                2535                2540

Phe Gly Ala Lys Glu Val Arg Ser Leu Ser Gly Arg Ala Val Asn His
2545                2550                2555                2560

Ile Lys Ser Val Trp Lys Asp Leu Leu Glu Asp Ser Glu Thr Pro Ile
                2565                2570                2575

Pro Thr Thr Ile Met Ala Lys Asn Glu Val Phe Cys Val Asp Pro Thr
            2580                2585                2590

Lys Gly Gly Lys Lys Ala Ala Arg Leu Ile Val Tyr Pro Asp Leu Gly
        2595                2600                2605

Val Arg Val Cys Glu Lys Met Ala Leu Tyr Asp Ile Thr Gln Lys Leu
    2610                2615                2620

Pro Gln Ala Val Met Gly Ala Ser Tyr Gly Phe Gln Tyr Ser Pro Ala
2625                2630                2635                2640

Gln Arg Val Glu Phe Leu Leu Lys Ala Trp Ala Glu Lys Lys Asp Pro
                2645                2650                2655

Met Gly Phe Ser Tyr Asp Thr Arg Cys Phe Asp Ser Thr Val Thr Glu
            2660                2665                2670

Arg Asp Ile Arg Thr Glu Glu Ser Ile Tyr Arg Ala Cys Ser Leu Pro
        2675                2680                2685

Glu Glu Ala His Thr Ala Ile His Ser Leu Thr Glu Arg Leu Tyr Val
    2690                2695                2700

Gly Gly Pro Met Phe Asn Ser Lys Gly Gln Thr Cys Gly Tyr Arg Arg
2705                2710                2715                2720

Cys Arg Ala Ser Gly Val Leu Thr Thr Ser Met Gly Asn Thr Ile Thr
                2725                2730                2735

Cys Tyr Val Lys Ala Leu Ala Ala Cys Lys Ala Ala Gly Ile Ile Ala
            2740                2745                2750

Pro Thr Met Leu Val Cys Gly Asp Asp Leu Val Val Ile Ser Glu Ser
        2755                2760                2765

Gln Gly Thr Glu Glu Asp Glu Arg Asn Leu Arg Ala Phe Thr Glu Ala
    2770                2775                2780

Met Thr Arg Tyr Ser Ala Pro Pro Gly Asp Pro Pro Arg Pro Glu Tyr
2785                2790                2795                2800

Asp Leu Glu Leu Ile Thr Ser Cys Ser Ser Asn Val Ser Val Ala Leu
                2805                2810                2815

Gly Pro Gln Gly Arg Arg Arg Tyr Tyr Leu Thr Arg Asp Pro Thr Thr
            2820                2825                2830

Pro Ile Ala Arg Ala Ala Trp Glu Thr Val Arg His Ser Pro Val Asn
        2835                2840                2845

Ser Trp Leu Gly Asn Ile Ile Gln Tyr Ala Pro Thr Ile Trp Ala Arg
    2850                2855                2860
```

-continued

Met Val Leu Met Thr His Phe Phe Ser Ile Leu Met Ala Gln Asp Thr
2865                2870                2875                2880

Leu Asp Gln Asn Leu Asn Phe Glu Met Tyr Gly Ala Val Tyr Ser Val
            2885                2890                2895

Ser Pro Leu Asp Leu Pro Ala Ile Ile Glu Arg Leu His Gly Leu Asp
        2900                2905                2910

Ala Phe Ser Leu His Thr Tyr Thr Pro His Glu Leu Thr Arg Val Ala
    2915                2920                2925

Ser Ala Leu Arg Lys Leu Gly Ala Pro Pro Leu Arg Ala Trp Lys Ser
2930                2935                2940

Arg Ala Arg Ala Val Arg Ala Ser Leu Ile Ser Arg Gly Gly Arg Ala
2945                2950                2955                2960

Ala Val Cys Gly Arg Tyr Leu Phe Asn Trp Ala Val Lys Thr Lys Leu
            2965                2970                2975

Lys Leu Thr Pro Leu Pro Glu Ala Arg Leu Leu Asp Leu Ser Ser Trp
        2980                2985                2990

Phe Thr Val Gly Ala Gly Gly Gly Asp Ile Tyr His Ser Val Ser Arg
    2995                3000                3005

Ala Arg Pro Arg Leu Leu Leu Phe Gly Leu Leu Leu Leu Phe Val Gly
        3010                3015                3020

Val Gly Leu Phe Leu Leu Pro Ala Arg
3025                3030

<210> SEQ ID NO 6
<211> LENGTH: 9599
<212> TYPE: DNA
<213> ORGANISM: Hepatitis C virus strain H77

<400> SEQUENCE: 6
gccagccccc tgatggggggc gacactccac catgaatcac tcccctgtga ggaactactg     60
tcttcacgca gaaagcgtct agccatggcg ttagtatgag tgtcgtgcag cctccaggac    120
ccccctccc gggagagcca tagtggtctg cggaaccggt gagtacaccg gaattgccag    180
gacgaccggg tcctttcttg gataaacccg ctcaatgcct ggagatttgg gcgtgccccc    240
gcaagactgc tagccgagta gtgttgggtc gcgaaaggcc ttgtggtact gcctgatagg    300
gtgcttgcga gtgccccggg aggtctcgta gaccgtgcac catgagcacg aatcctaaac    360
ctcaaagaaa aaccaaacgt aacaccaacc gtcgcccaca ggacgtcaag ttcccgggtg    420
gcggtcagat cgttggtgga gtttacttgt tgccgcgcag gggccctaga ttgggtgtgc    480
gcgcgacgag gaagacttcc gagcggtcgc aacctcgagg tagacgtcag cctatcccca    540
aggcacgtcg gcccgaggc aggacctggg ctcagcccgg gtaccttgg ccctctatg    600
gcaatgaggg ttgcgggtgg gcgggatggc tcctgtctcc ccgtggctct cggcctagct    660
ggggccccac agaccccgg cgtaggtcgc gcaatttggg taaggtcatc gatacccta    720
cgtgcggctt cgccgacctc atgggtaca taccgctcgt cggcgcccct cttggaggcg    780
ctgccagggc cctggcgcat ggcgtccggg ttctggaaga cggcgtgaac tatgcaacag    840
ggaaccttcc tggttgctct ttctctatct tccttctggc cctgctctct tgcctgactg    900
tgcccgcttc agcctaccaa gtgcgcaatt cctcggggct ttaccatgtc accaatgatt    960
gccctaactc gagtattgtg tacgaggcgg ccgatgccat cctgcacact ccgggtgtg   1020
tcccttgcgt tcgcgagggt aacgcctcga ggtgttgggt ggcggtgacc ccacgtgg   1080
ccaccaggga cggcaaactc cccacaacgc agcttcgacg tcatatcgat ctgcttgtcg   1140

-continued

```
ggagcgccac cctctgctcg gccctctacg tggggggacct gtgcgggtct gtctttcttg    1200
ttggtcaact gtttaccttc tctcccaggc gccactggac gacgcaagac tgcaattgtt    1260
ctatctatcc cggccatata acgggtcatc gcatggcatg ggatatgatg atgaactggt    1320
cccctacggc agcgttggtg gtagctcagc tgctccggat cccacaagcc atcatggaca    1380
tgatcgctgg tgctcactgg ggagtcctgg cgggcatagc gtatttctcc atggtgggga    1440
actgggcgaa ggtcctggta gtgctgctgc tatttgccgg cgtcgacgcg gaaacccacg    1500
tcaccggggg aaatgccggc cgcaccacgg ctgggcttgt tggtctcctt acaccaggcg    1560
ccaagcagaa catccaactg atcaacacca acggcagttg gcacatcaat agcacggcct    1620
tgaattgcaa tgaaagcctt aacaccggct ggttagcagg gctcttctat caacacaaat    1680
tcaactcttc aggctgtcct gagaggttgg ccagctgccg acgccttacc gattttgccc    1740
agggctgggg tcctatcagt tatgccaacg gaagcggcct cgacgaacgc ccctactgct    1800
ggcactaccc tccaagacct tgtggcattg tgcccgcaaa gagcgtgtgt ggcccggtat    1860
attgcttcac tcccagcccc gtggtggtgg gaacgaccga caggtcgggc gcgcctacct    1920
acagctgggg tgcaaatgat acggatgtct tcgtccttaa caacaccagg ccaccgctgg    1980
gcaattggtt cggttgtacc tggatgaact caactggatt caccaaagtg tgcggagcgc    2040 cccttgtgt catcggaggg gtgggcaaca acaccttgct ctgccccact gattgcttcc    2100
gcaaacatcc ggaagccaca tactctcggt gcggctccgg tccctggatt acacccaggt    2160
gcatggtcga ctacccgtat aggctttggc actatccttg taccatcaat tacaccatat    2220
tcaaagtcag gatgtacgtg ggaggggtcg agcacaggct ggaagcggcc tgcaactgga    2280
cgcggggcga acgctgtgat ctggaagaca gggacaggtc cgagctcagc ccgttgctgc    2340
tgtccaccac acagtggcag gtccttccgt gttctttcac gaccctgcca gccttgtcca    2400
ccggcctcat ccacctccac cagaacattg tggacgtgca gtacttgtac ggggtagggt    2460
caagcatcgc gtcctgggcc attaagtggg agtacgtcgt tctcctgttc cttctgcttg    2520
cagacgcgcg cgtctgctcc tgcttgtgga tgatgttact catatcccaa gcggaggcgg    2580 cttttggagaa cctcgtaata ctcaatgcag catccctggc cgggacgcac ggtcttgtgt    2640
ccttcctcgt gttcttctgc tttgcgtggt atctgaaggg taggtgggtg cccggagcgg    2700
tctacgccct ctacgggatg tggcctctcc tcctgctcct gctggcgttg cctcagcggg    2760
catacgcact ggacacggag gtggccgcgt cgtgtggcgg cgttgttctt gtcgggttaa    2820
tggcgctgac tctgtcgcca tattacaagc gctatatcag ctggtgcatg tggtggcttc    2880
agtattttct gaccagagta gaagcgcaac tgcacgtgtg ggttcccccc ctcaacgtcc    2940 gggggggggcg cgatgccgtc atcttactca tgtgtgtagt acacccgacc ctggtatttg    3000
acatcaccaa actactcctg gccatcttcg gaccccttg gattcttcaa gccagtttgc    3060
ttaaagtccc ctacttcgtg cgcgttcaag gccttctccg gatctgcgcg ctagcgcgga    3120
agatagccgg aggtcattac gtgcaaatgg ccatcatcaa gttagggcg cttactggca    3180 cctatgtgta taaccatctc acccctcttc gagactgggc gcacaacggc ctgcgagatc    3240
tggccgtggc tgtggaacca gtcgtcttct cccgaatgga gaccaagctc atcacgtggg    3300
gggcagatac cgccgcgtgc ggtgacatca tcaacggctt gccgtctct gcccgtaggg    3360 gccaggagat actgcttggg ccagccgacg gaatggtctc caaggggtgg aggttgctgg    3420
cgcccatcac ggcgtacgcc cagcagacga gaggcctcct agggtgtata atcaccagcc    3480
tgactggccg ggacaaaaac caagtggagg gtgaggtcca gatcgtgtca actgctaccc    3540
```

-continued

```
aaaccttcct ggcaacgtgc atcaatgggg tatgctggac tgtctaccac ggggccggaa    3600
cgaggaccat cgcatcaccc aagggtcctg tcatccagat gtataccaat gtggaccaag    3660
accttgtggg ctggcccgct cctcaaggtt cccgctcatt gacaccctgt acctgcggct    3720
cctcggacct ttacctggtc acgaggcacg ccgatgtcat tcccgtgcgc cggcgaggtg    3780
atagcagggg tagcctgctt tcgcccggc ccatttccta cttgaaaggc tcctcggggg     3840
gtccgctgtt gtgccccgcg ggacacgccg tgggcctatt cagggccgcg tgtgcaccc     3900
gtggagtggc taaagcggtg gactttatcc ctgtggagaa cctagggaca accatgagat    3960
ccccggtgtt cacggacaac tcctctccac cagcagtgcc ccagagcttc caggtggccc    4020
acctgcatgc tcccaccggc agcggtaaga gcaccaaggt cccggctgcg tacgcagccc    4080
agggctacaa ggtgttggtg ctcaaccccct ctgttgctgc aacgctgggc tttggtgctt   4140
acatgtccaa ggcccatggg gttgatccta atatcaggac cggggtgaga acaattacca    4200
ctggcagccc catcacgtac tccacctacg gcaagttcct tgccgacggc gggtgctcag    4260
gaggtgctta tgacataata atttgtgacg agtgccactc cacggatgcc acatccatct    4320
tgggcatcgg cactgtcctt gaccaagcag agactgcggg ggcgagactg gttgtgctcg    4380
ccactgctac ccctccgggc tccgtcactg tgtcccatcc taacatcgag gaggttgctc    4440
tgtccaccac cggagagatc ccctttacg gcaaggctat cccctcgag gtgatcaagg      4500
ggggaagaca tctcatcttc tgccactcaa agaagaagtg cgacgagctc gccgcgaagc    4560
tggtcgcatt gggcatcaat gccgtggcct actaccgcgg tcttgacgtg tctgtcatcc    4620
cgaccagcgg cgatgttgtc gtcgtgtcga ccgatgctct catgactggc tttaccggcg    4680
acttcgactc tgtgatagac tgcaacacgt gtgtcactca cagtcgat ttcagccttg      4740
accctacctt taccattgag acaaccacgc tcccccagga tgctgtctcc aggactcaac    4800
gccggggcag gactggcagg gggaagccag gcatctatag atttgtggca ccggggagc     4860
gcccctccgg catgttcgac tcgtccgtcc tctgtgagtg ctatgacgcg ggctgtgctt    4920
ggtatgagct cacgcccgcc gagactacag ttaggctacg agcgtacatg aacacccgg     4980
ggcttcccgt gtgccaggac catcttgaat tttgggaggg cgtctttacg ggcctcactc    5040
atatagatgc ccacttttta tcccagacaa agcagagtgg ggagaacttt ccttacctgg    5100
tagcgtacca agccaccgtg tgcgctaggg ctcaagcccc tccccatcg tgggaccaga     5160
tgtgaaagtg tttgatccgc cttaaaccca ccctccatgg gccaacaccc ctgctataca    5220
gactgggcgc tgttcagaat gaagtcaccc tgacgcaccc aatcaccaaa tacatcatga    5280
catgcatgtc ggccgacctg gaggtcgtca cgagcacctg ggtgctcgtt ggcggcgtcc    5340
tggctgctct ggccgcgtat tgcctgtcaa caggctgcgt ggtcatagtg ggcaggatcg    5400
tcttgtccgg gaagccggca attatacctg acagggaggt tctctaccag gagttcgatg    5460
agatggaaga gtgctctcag cacttaccgt acatcgagca agggatgatg ctcgctgagc    5520
agttcaagca gaaggccctc ggcctcctgc agaccgcgtc ccgccatgca gaggttatca    5580
cccctgctgt ccagaccaac tggcagaaac tcgaggtctt ttgggcgaag cacatgtgga    5640
atttcatcag tgggatacaa tacttggcgg cctgtcaac gctgcctggt aaccccgcca     5700
ttgcttcatt gatggctttt acagctgccg tcaccagccc actaaccact ggccaaaccc    5760
tcctcttcaa catattgggg gggtgggtgg ctgcccagct cgccgccccc ggtgccgcta    5820
ctgcctttgt gggtgctggc ctagctggcg ccgccatcgg cagcgttgga ctggggaagg    5880
```

```
tcctcgtgga cattcttgca gggtatggcg cgggcgtggc gggagctctt gtagcattca   5940
agatcatgag cggtgaggtc ccctccacgg aggacctggt caatctgctg cccgccatcc   6000
tctcgcctgg agcccttgta gtcggtgtgg tctgcgcagc aatactgcgc cggcacgttg   6060
gcccgggcga gggggcagtg caatggatga accggctaat agccttcgcc tcccggggga   6120
accatgtttc ccccacgcac tacgtgccgg agagcgatgc agccgcccgc gtcactgcca   6180
tactcagcag cctcactgta acccagctcc tgaggcgact gcatcagtgg ataagctcgg   6240
agtgtaccac tccatgctcc ggttcctggc taagggacat ctgggactgg atatgcgagg   6300
tgctgagcga ctttaagacc tggctgaaag ccaagctcat gccacaactg cctgggattc   6360
cctttgtgtc ctgccagcgc gggtataggg gggtctggcg aggagacggc attatgcaca   6420
ctcgctgcca ctgtggagct gagatcactg gacatgtcaa aaacgggacg atgaggatcg   6480
tcggtcctag gacctgcagg aacatgtgga gtgggacgtt ccccattaac gcctacacca   6540
cggggcccctg tactcccctt cctgcgccga actataagtt cgcgctgtgg agggtgtctg   6600
cagaggaata cgtggagata aggcgggtgg gggacttcca ctacgtatcg ggtatgacta   6660
ctgacaatct taaatgcccg tgccagatcc catcgcccga attttcaca gaattggacg    6720
gggtgcgcct acacaggttt gcgccccctt gcaagccctt gctgcgggag gaggtatcat   6780
tcagagtagg actccacgag tacccggtgg ggtcgcaatt accttgcgag cccgaaccgg   6840
acgtagccgt gttgacgtcc atgctcactg atccctccca tataacagca gaggcggccg   6900
ggagaaggtt ggcgagaggg tcaccccctt ctatggccag ctcctcggct agccagctgt   6960
ccgctccatc tctcaaggca acttgcaccg ccaaccatga ctcccctgac gccgagctca   7020
tagaggctaa cctcctgtgg aggcaggaga tgggcggcaa catcaccagg gttgagtcag   7080
agaacaaagt ggtgattctg gactccttcg atccgcttgt ggcagaggag gatgagcggg   7140
aggtctccgt acctgcagaa attctgcgga agtctcggag attcgcccgg gccctgcccg   7200
tctgggcgcg gccggactac aacccccgc tagtagagac gtggaaaaag cctgactacg    7260
aaccacctgt ggtccatggc tgcccgctac cacctccacg gtcccctcct gtgcctccgc   7320
ctcggaaaaa gcgtacggtg gtcctcaccg aatcaaccct atctactgcc ttggccgagc   7380
ttgccaccaa aagttttggc agctcctcaa cttccggcat tacgggcgac aatacgacaa   7440
catcctctga gcccgcccct tctggctgcc ccccgactc cgacgttgag tcctattctt    7500
ccatgccccc cctggagggg gagcctgggg atccggatct cagcgacggg tcatggtcga   7560
cggtcagtag tggggccgac acggaagatg tcgtgtgctg ctcaatgtct tattcctgga   7620
caggcgcact cgtcaccccg tgcgctgcgg aagaacaaaa actgcccatc aacgcactga   7680
gcaactcgtt gctacgccat cacaatctgg tgtattccac cacttcacgc agtgcttgcc   7740
aaaggcagaa gaaagtcaca tttgacagac tgcaagttct ggacagccat taccaggacg   7800
tgctcaagga ggtcaaagca gcggcgtcaa agtgaaggc taacttgcta tccgtagagg    7860
aagcttgcag cctgacgccc ccacattcag ccaaatccaa gtttggctat ggggcaaaag   7920
acgtccgttg ccatgccaga aaggccgtag cccacatcaa ctccgtgtgg aaagaccttc   7980
tggaagacag tgtaacacca atagacacta ccatcatggc caagaacgag gttttctgcg   8040
ttcagcctga aaggggggt cgtaagccag ctcgtctcat cgtgttcccc gacctgggcg    8100
tgcgcgtgtg cgagaagatg gccctgtacg acgtggttag caagctcccc ctggccgtga   8160
tgggaagctc ctacgattc caatactcac caggacagcg ggttgaattc ctcgtgcaag    8220
cgtggaagtc caagaagacc ccgatggggt tctcgtatga tacccgctgt tttgactcca   8280
```

-continued

```
cagtcactga gagcgacatc cgtacggagg aggcaattta ccaatgttgt gacctggacc    8340
cccaagcccg cgtggccatc aagtccctca ctgagaggct ttatgttggg ggccctctta    8400
ccaattcaag gggggaaaac tgcggctacc gcaggtgccg cgcgagcggc gtactgacaa    8460
ctagctgtgg taacaccctc acttgctaca tcaaggcccg ggcagcctgt cgagccgcag    8520
ggctccagga ctgcaccatg ctcgtgtgtg gcgacgactt agtcgttatc tgtgaaagtg    8580
cgggggtcca ggaggacgcg gcgagcctga gagccttcac ggaggctatg accaggtact    8640
ccgccccccc cggggacccc ccacaaccag aatacgactt ggagcttata acatcatgct    8700
cctccaacgt gtcagtcgcc cacgacggcg ctggaaagag ggtctactac cttacccgtg    8760
accctacaac cccctcgcg agagccgcgt gggagacagc aagacacact ccagtcaatt    8820
cctggctagg caacataatc atgtttgccc ccacactgtg ggcgaggatg atactgatga    8880
cccatttctt tagcgtcctc atagccaggg atcagcttga acaggctctt aactgtgaga    8940
tctacggagc ctgctactcc atagaaccac tggatctacc tccaatcatt caaagactcc    9000
atggcctcag cgcattttca ctccacagtt actctccagg tgaaatcaat agggtggccg    9060
catgcctcag aaaacttggg gtcccgccct tgcgagcttg gagacaccgg gcccggagcg    9120
tccgcgctag gcttctgtcc agaggaggca gggctgccat atgtggcaag tacctcttca    9180
actgggcagt aagaacaaag ctcaaactca ctccaatagc ggccgctggc cggctggact    9240
tgtccggttg gttcacggct ggctacagcg ggggagacat ttatcacagc gtgtctcatg    9300
cccggccccg ctggttctgg ttttgcctac tcctgctcgc tgcagggta ggcatctacc    9360 tcctccccaa ccgatgaagg ttggggtaaa cactccggcc tcttaagcca tttcctgttt    9420
tttttttttt tttttttttt tttttcttttt ttttttttctt tccttttcctt ctttttttcc    9480 tttcttttc ccttctttaa tggtggctcc atcttagccc tagtcacggc tagctgtgaa    9540
aggtccgtga gccgcatgac tgcagagagt gctgatactg gcctctctgc agatcatgt    9599
```

<210> SEQ ID NO 7
<211> LENGTH: 3011
<212> TYPE: PRT
<213> ORGANISM: Hepatitis C virus strain H77

<400> SEQUENCE: 7

```
Met Ser Thr Asn Pro Lys Pro Gln Arg Lys Thr Lys Arg Asn Thr Asn
  1               5                  10                  15

Arg Arg Pro Gln Asp Val Lys Phe Pro Gly Gly Gly Gln Ile Val Gly
             20                  25                  30

Gly Val Tyr Leu Leu Pro Arg Arg Gly Pro Arg Leu Gly Val Arg Ala
         35                  40                  45

Thr Arg Lys Thr Ser Glu Arg Ser Gln Pro Arg Gly Arg Arg Gln Pro
     50                  55                  60

Ile Pro Lys Ala Arg Arg Pro Glu Gly Arg Thr Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140
```

```
Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
            165                 170                 175

Phe Leu Leu Ala Leu Leu Ser Cys Leu Thr Val Pro Ala Ser Ala Tyr
        180                 185                 190

Gln Val Arg Asn Ser Ser Gly Leu Tyr His Val Thr Asn Asp Cys Pro
    195                 200                 205

Asn Ser Ser Ile Val Tyr Glu Ala Ala Asp Ala Ile Leu His Thr Pro
210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Phe Ala Gly Val Asp Ala Glu
    370                 375                 380

Thr His Val Thr Gly Gly Asn Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560
```

-continued

```
Thr Lys Val Cys Gly Ala Pro Pro Cys Val Ile Gly Val Gly Asn
                565             570             575
Asn Thr Leu Leu Cys Pro Thr Asp Cys Phe Arg Lys His Pro Glu Ala
        580             585             590
Thr Tyr Ser Arg Cys Gly Ser Gly Pro Trp Ile Thr Pro Arg Cys Met
        595             600             605
Val Asp Tyr Pro Tyr Arg Leu Trp His Tyr Pro Cys Thr Ile Asn Tyr
610             615             620
Thr Ile Phe Lys Val Arg Met Tyr Val Gly Gly Val Glu His Arg Leu
625             630             635             640
Glu Ala Ala Cys Asn Trp Thr Arg Gly Glu Arg Cys Asp Leu Glu Asp
                645             650             655
Arg Asp Arg Ser Glu Leu Ser Pro Leu Leu Leu Ser Thr Thr Gln Trp
            660             665             670
Gln Val Leu Pro Cys Ser Phe Thr Thr Leu Pro Ala Leu Ser Thr Gly
            675             680             685
Leu Ile His Leu His Gln Asn Ile Val Asp Val Gln Tyr Leu Tyr Gly
        690             695             700
Val Gly Ser Ser Ile Ala Ser Trp Ala Ile Lys Trp Glu Tyr Val Val
705             710             715             720
Leu Leu Phe Leu Leu Leu Ala Asp Ala Arg Val Cys Ser Cys Leu Trp
                725             730             735
Met Met Leu Leu Ile Ser Gln Ala Glu Ala Ala Leu Glu Asn Leu Val
            740             745             750
Ile Leu Asn Ala Ala Ser Leu Ala Gly Thr His Gly Leu Val Ser Phe
        755             760             765
Leu Val Phe Phe Cys Phe Ala Trp Tyr Leu Lys Gly Arg Trp Val Pro
        770             775             780
Gly Ala Val Tyr Ala Leu Tyr Gly Met Trp Pro Leu Leu Leu Leu
785             790             795             800
Leu Ala Leu Pro Gln Arg Ala Tyr Ala Leu Asp Thr Glu Val Ala Ala
                805             810             815
Ser Cys Gly Gly Val Val Leu Val Gly Leu Met Ala Leu Thr Leu Ser
            820             825             830
Pro Tyr Tyr Lys Arg Tyr Ile Ser Trp Cys Met Trp Trp Leu Gln Tyr
        835             840             845
Phe Leu Thr Arg Val Glu Ala Gln Leu His Val Trp Val Pro Pro Leu
850             855             860
Asn Val Arg Gly Gly Arg Asp Ala Val Ile Leu Leu Met Cys Val Val
865             870             875             880
His Pro Thr Leu Val Phe Asp Ile Thr Lys Leu Leu Leu Ala Ile Phe
                885             890             895
Gly Pro Leu Trp Ile Leu Gln Ala Ser Leu Leu Lys Val Pro Tyr Phe
            900             905             910
Val Arg Val Gln Gly Leu Leu Arg Ile Cys Ala Leu Ala Arg Lys Ile
        915             920             925
Ala Gly Gly His Tyr Val Gln Met Ala Ile Ile Lys Leu Gly Ala Leu
        930             935             940
Thr Gly Thr Tyr Val Tyr Asn His Leu Thr Pro Leu Arg Asp Trp Ala
945             950             955             960
His Asn Gly Leu Arg Asp Leu Ala Val Ala Val Glu Pro Val Val Phe
                965             970             975
Ser Arg Met Glu Thr Lys Leu Ile Thr Trp Gly Ala Asp Thr Ala Ala
```

-continued

```
                   980             985             990
Cys Gly Asp Ile Ile Asn Gly Leu Pro Val Ser Ala Arg Arg Gly Gln
            995                 1000                1005

Glu Ile Leu Leu Gly Pro Ala Asp Gly Met Val Ser Lys Gly Trp Arg
    1010                1015                1020

Leu Leu Ala Pro Ile Thr Ala Tyr Ala Gln Gln Thr Arg Gly Leu Leu
1025                1030                1035                1040

Gly Cys Ile Ile Thr Ser Leu Thr Gly Arg Asp Lys Asn Gln Val Glu
                1045                1050                1055

Gly Glu Val Gln Ile Val Ser Thr Ala Thr Gln Thr Phe Leu Ala Thr
            1060                1065                1070

Cys Ile Asn Gly Val Cys Trp Thr Val Tyr His Gly Ala Gly Thr Arg
        1075                1080                1085

Thr Ile Ala Ser Pro Lys Gly Pro Val Ile Gln Met Tyr Thr Asn Val
    1090                1095                1100

Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
        1155                1160                1165

Leu Leu Cys Pro Ala Gly His Ala Val Gly Leu Phe Arg Ala Ala Val
    1170                1175                1180

Cys Thr Arg Gly Val Ala Lys Ala Val Asp Phe Ile Pro Val Glu Asn
1185                1190                1195                1200

Leu Gly Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
        1235                1240                1245

Tyr Lys Val Leu Val Leu Asn Pro Ser Val Ala Ala Thr Leu Gly Phe
    1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
            1300                1305                1310

Ile Ile Cys Asp Glu Cys His Ser Thr Asp Ala Thr Ser Ile Leu Gly
        1315                1320                1325

Ile Gly Thr Val Leu Asp Gln Ala Glu Thr Ala Gly Ala Arg Leu Val
    1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
        1395                1400                1405
```

```
Ala Leu Gly Ile Asn Ala Val Ala Tyr Tyr Arg Gly Leu Asp Val Ser
    1410                1415                1420

Val Ile Pro Thr Ser Gly Asp Val Val Val Ser Thr Asp Ala Leu
1425                1430                1435                1440

Met Thr Gly Phe Thr Gly Asp Phe Asp Ser Val Ile Asp Cys Asn Thr
            1445                1450                1455

Cys Val Thr Gln Thr Val Asp Phe Ser Leu Asp Pro Thr Phe Thr Ile
                1460                1465                1470

Glu Thr Thr Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520

Tyr Asp Ala Gly Cys Ala Trp Tyr Glu Leu Thr Pro Ala Glu Thr Thr
                1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
        1555                1560                1565

Asp Ala His Phe Leu Ser Gln Thr Lys Gln Ser Gly Glu Asn Phe Pro
    1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Thr Cys
        1635                1640                1645

Met Ser Ala Asp Leu Glu Val Val Thr Ser Thr Trp Val Leu Val Gly
    1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
                1685                1690                1695

Asp Arg Glu Val Leu Tyr Gln Glu Phe Asp Glu Met Glu Glu Cys Ser
            1700                1705                1710

Gln His Leu Pro Tyr Ile Glu Gln Gly Met Met Leu Ala Glu Gln Phe
        1715                1720                1725

Lys Gln Lys Ala Leu Gly Leu Leu Gln Thr Ala Ser Arg His Ala Glu
    1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
                1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Gly Gln Thr Leu Leu
        1795                1800                1805

Phe Asn Ile Leu Gly Gly Trp Val Ala Ala Gln Leu Ala Ala Pro Gly
    1810                1815                1820
```

-continued

```
Ala Ala Thr Ala Phe Val Gly Ala Gly Leu Ala Gly Ala Ile Gly
1825                1830                1835                1840

Ser Val Gly Leu Gly Lys Val Leu Val Asp Ile Leu Ala Gly Tyr Gly
                1845                1850                1855

Ala Gly Val Ala Gly Ala Leu Val Ala Phe Lys Ile Met Ser Gly Glu
                1860                1865                1870

Val Pro Ser Thr Glu Asp Leu Val Asn Leu Leu Pro Ala Ile Leu Ser
                1875                1880                1885

Pro Gly Ala Leu Val Val Gly Val Val Cys Ala Ala Ile Leu Arg Arg
                1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                1925                1930                1935

Glu Ser Asp Ala Ala Ala Arg Val Thr Ala Ile Leu Ser Ser Leu Thr
                1940                1945                1950

Val Thr Gln Leu Leu Arg Arg Leu His Gln Trp Ile Ser Ser Glu Cys
                1955                1960                1965

Thr Thr Pro Cys Ser Gly Ser Trp Leu Arg Asp Ile Trp Asp Trp Ile
                1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
                2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
                2085                2090                2095

Gly Asp Phe His Tyr Val Ser Gly Met Thr Thr Asp Asn Leu Lys Cys
                2100                2105                2110

Pro Cys Gln Ile Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
                2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Met Ala Ser Ser Ser Ala Ser Gln Leu Ser Ala
                2195                2200                2205

Pro Ser Leu Lys Ala Thr Cys Thr Ala Asn His Asp Ser Pro Asp Ala
                2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
```

-continued

```
                2245                2250                2255
Asp Pro Leu Val Ala Glu Glu Asp Glu Arg Glu Val Ser Val Pro Ala
            2260                2265                2270
Glu Ile Leu Arg Lys Ser Arg Arg Phe Ala Arg Ala Leu Pro Val Trp
            2275                2280                2285
Ala Arg Pro Asp Tyr Asn Pro Pro Leu Val Glu Thr Trp Lys Lys Pro
            2290                2295                2300
Asp Tyr Glu Pro Pro Val Val His Gly Cys Pro Leu Pro Pro Pro Arg
2305                2310                2315                2320
Ser Pro Pro Val Pro Pro Arg Lys Lys Arg Thr Val Val Leu Thr
            2325                2330                2335
Glu Ser Thr Leu Ser Thr Ala Leu Ala Glu Leu Ala Thr Lys Ser Phe
            2340                2345                2350
Gly Ser Ser Ser Thr Ser Gly Ile Thr Gly Asp Asn Thr Thr Thr Ser
            2355                2360                2365
Ser Glu Pro Ala Pro Ser Gly Cys Pro Pro Asp Ser Asp Val Glu Ser
            2370                2375                2380
Tyr Ser Ser Met Pro Pro Leu Glu Gly Glu Pro Gly Asp Pro Asp Leu
2385                2390                2395                2400
Ser Asp Gly Ser Trp Ser Thr Val Ser Ser Gly Ala Asp Thr Glu Asp
            2405                2410                2415
Val Val Cys Cys Ser Met Ser Tyr Ser Trp Thr Gly Ala Leu Val Thr
            2420                2425                2430
Pro Cys Ala Ala Glu Glu Gln Lys Leu Pro Ile Asn Ala Leu Ser Asn
            2435                2440                2445
Ser Leu Leu Arg His His Asn Leu Val Tyr Ser Thr Thr Ser Arg Ser
            2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ala Ser
            2485                2490                2495
Lys Val Lys Ala Asn Leu Leu Ser Val Glu Glu Ala Cys Ser Leu Thr
            2500                2505                2510
Pro Pro His Ser Ala Lys Ser Lys Phe Gly Tyr Gly Ala Lys Asp Val
            2515                2520                2525
Arg Cys His Ala Arg Lys Ala Val Ala His Ile Asn Ser Val Trp Lys
            2530                2535                2540
Asp Leu Leu Glu Asp Ser Val Thr Pro Ile Asp Thr Thr Ile Met Ala
2545                2550                2555                2560
Lys Asn Glu Val Phe Cys Val Gln Pro Glu Lys Gly Gly Arg Lys Pro
            2565                2570                2575
Ala Arg Leu Ile Val Phe Pro Asp Leu Gly Val Arg Val Cys Glu Lys
            2580                2585                2590
Met Ala Leu Tyr Asp Val Val Ser Lys Leu Pro Leu Ala Val Met Gly
            2595                2600                2605
Ser Ser Tyr Gly Phe Gln Tyr Ser Pro Gly Gln Arg Val Glu Phe Leu
            2610                2615                2620
Val Gln Ala Trp Lys Ser Lys Lys Thr Pro Met Gly Phe Ser Tyr Asp
2625                2630                2635                2640
Thr Arg Cys Phe Asp Ser Thr Val Thr Glu Ser Asp Ile Arg Thr Glu
            2645                2650                2655
Glu Ala Ile Tyr Gln Cys Cys Asp Leu Asp Pro Gln Ala Arg Val Ala
            2660                2665                2670
```

Ile Lys Ser Leu Thr Glu Arg Leu Tyr Val Gly Gly Pro Leu Thr Asn
        2675                2680                2685

Ser Arg Gly Glu Asn Cys Gly Tyr Arg Arg Cys Arg Ala Ser Gly Val
    2690                2695                2700

Leu Thr Thr Ser Cys Gly Asn Thr Leu Thr Cys Tyr Ile Lys Ala Arg
2705                2710                2715                2720

Ala Ala Cys Arg Ala Ala Gly Leu Gln Asp Cys Thr Met Leu Val Cys
        2725                2730                2735

Gly Asp Asp Leu Val Val Ile Cys Glu Ser Ala Gly Val Gln Glu Asp
        2740                2745                2750

Ala Ala Ser Leu Arg Ala Phe Thr Glu Ala Met Thr Arg Tyr Ser Ala
        2755                2760                2765

Pro Pro Gly Asp Pro Pro Gln Pro Glu Tyr Asp Leu Glu Leu Ile Thr
    2770                2775                2780

Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
        2805                2810                2815

Trp Glu Thr Ala Arg His Thr Pro Val Asn Ser Trp Leu Gly Asn Ile
        2820                2825                2830

Ile Met Phe Ala Pro Thr Leu Trp Ala Arg Met Ile Leu Met Thr His
        2835                2840                2845

Phe Phe Ser Val Leu Ile Ala Arg Asp Gln Leu Glu Gln Ala Leu Asn
    2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
        2885                2890                2895

Tyr Ser Pro Gly Glu Ile Asn Arg Val Ala Ala Cys Leu Arg Lys Leu
    2900                2905                2910

Gly Val Pro Pro Leu Arg Ala Trp Arg His Arg Ala Arg Ser Val Arg
        2915                2920                2925

Ala Arg Leu Leu Ser Arg Gly Gly Arg Ala Ala Ile Cys Gly Lys Tyr
        2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
        2965                2970                2975

Gly Gly Asp Ile Tyr His Ser Val Ser His Ala Arg Pro Arg Trp Phe
        2980                2985                2990

Trp Phe Cys Leu Leu Leu Leu Ala Ala Gly Val Gly Ile Tyr Leu Leu
    2995                3000                3005

Pro Asn Arg
    3010

<210> SEQ ID NO 8
<211> LENGTH: 9595
<212> TYPE: DNA
<213> ORGANISM: Hepatitis C virus strain HC-J4

<400> SEQUENCE: 8
gccagccccc tgatgggggc gacactccac catgaatcac tcccctgtga ggaactactg     60
tcttcacgca gaaagcgtct agccatggcg ttagtatgag tgtcgtgcag cctccaggac    120

-continued

| | |
|---|---|
| cccccctccc gggagagcca tagtggtctg cggaaccggt gagtacaccg gaattgccag | 180 |
| gacgaccggg tcctttcttg gatcaacccg ctcaatgcct ggagatttgg gcgtgccccc | 240 |
| gcgagactgc tagccgagta gtgttgggtc gcgaaaggcc ttgtggtact gcctgatagg | 300 |
| gtgcttgcga gtgccccggg aggtctcgta gaccgtgcac catgagcacg aatcctaaac | 360 |
| ctcaaagaaa aaccaaacgt aacaccaacc gccgcccaca ggacgtcaag ttcccgggcg | 420 |
| gtggtcagat cgttggtgga gtttacctgt tgccgcgcag gggccccagg ttgggtgtgc | 480 |
| gcgcgactag gaaggcttcc gagcggtcgc aacctcgtgg aaggcgacaa cctatcccaa | 540 |
| aggctcgccg acccgagggc agggcctggg ctcagcccgg gtacccttgg ccctctatg | 600 |
| gcaatgaggg cctggggtgg gcaggatggc tcctgtcacc ccgcggctcc cggcctagtt | 660 |
| ggggccccac ggaccccgg cgtaggtcgc gtaacttggg taaggtcatc gatacccta | 720 |
| catgcggctt cgccgatctc atggggtaca ttccgctcgt cggcgccccc ctagggggcg | 780 |
| ctgccagggc cttggcacac ggtgtccggg ttctggagga cggcgtgaac tatgcaacag | 840 |
| ggaacttgcc cggttgctct ttctctatct tcctcttggc tctgctgtcc tgtttgacca | 900 |
| tcccagcttc cgcttatgaa gtgcgcaacg tgtccgggat ataccatgtc acgaacgact | 960 |
| gctccaactc aagcattgtg tatgaggcag cggacgtgat catgcatact cccgggtgcg | 1020 |
| tgccctgtgt tcaggagggt aacagctccc gttgctgggt agcgctcact cccacgctcg | 1080 |
| cggccaggaa tgccagcgtc cccactacga caatacgacg ccacgtcgac ttgctcgttg | 1140 |
| ggacggctgc tttctgctcc gctatgtacg tgggggatct ctgcggatct attttcctcg | 1200 |
| tctcccagct gttcaccttc tcgcctcgcc ggcatgagac agtgcaggac tgcaactgct | 1260 |
| caatctatcc cggccatgta tcaggtcacc gcatggcttg ggatatgatg atgaactggt | 1320 |
| cacctacaac agccctagtg gtgtcgcagt tgctccggat cccacaagct gtcgtggaca | 1380 |
| tggtggcggg ggcccactgg ggagtcctgg cgggccttgc ctactattcc atggtaggga | 1440 |
| actgggctaa ggttctgatt gtggcgctac tctttgccgg cgttgacggg gagacccaca | 1500 |
| cgacggggag ggtggccggc cacaccacct ccgggttcac gtccctttc tcatctgggg | 1560 |
| cgtctcagaa aatccagctt gtgaatacca acggcagctg gcacatcaac aggactgccc | 1620 |
| taaattgcaa tgactccctc caaactgggt tctttgccgc gctgttttac gcacacaagt | 1680 |
| tcaactcgtc cgggtgcccg gagcgcatgg ccagctgccg ccccattgac tggttcgccc | 1740 |
| agggggtgggg cccatcacc tatactaagc ctaacagctc ggatcagagg ccttattgct | 1800 |
| ggcattacgc gcctcgaccg tgtggtgtcg tacccgcgtc gcaggtgtgt ggtccagtgt | 1860 |
| attgtttcac cccaagccct gttgtggtgg ggaccaccga tcgttccggt gtccctacgt | 1920 |
| atagctgggg ggagaatgag acagacgtga tgctcctcaa caacacgcgt ccgccacaag | 1980 |
| gcaactggtt cggctgtaca tggatgaata gtactggtt cactaagacg tgcggaggtc | 2040 |
| ccccgtgtaa catcgggggg gtcggtaacc gcaccttgat ctgccccacg gactgcttcc | 2100 |
| ggaagcaccc cgaggctact tacacaaaat gtggctcggg gcctggtttg acacctaggt | 2160 |
| gcctagtaga ctaccatac aggctttggc actaccctg cactctcaat ttttccatct | 2220 |
| ttaaggttag gatgtatgtg ggggcgtgg agcacaggct caatgccgca tgcaattgga | 2280 |
| ctcgaggaga gcgctgtaac ttggaggaca gggataggtc agaactcagc ccgctgctgc | 2340 |
| tgtctacaac agagtggcag atactgccct gtgctttcac caccctaccg gctttatcca | 2400 |
| ctggtttgat ccatctccat cagaacatcg tggacgtgca ataccgtac ggtgtagggt | 2460 |
| cagcgtttgt ctccttgca atcaaatggg agtacatcct gttgcttttc cttctcctgg | 2520 |

-continued

```
cagacgcgcg cgtgtgtgcc tgcttgtgga tgatgctgct gatagcccag gctgaggccg   2580
ccttagagaa cttggtggtc ctcaatgcgg cgtccgtggc cggagcgcat ggtattctct   2640
cctttcttgt gttcttctgc gccgcctggt acattaaggg caggctggct cctggggcgg   2700
cgtatgcttt ttatggcgta tggccgctgc tcctgctcct actggcgtta ccaccacgag   2760
cttacgcctt ggaccgggag atggctgcat cgtgcggggg tgcggttctt gtaggtctgg   2820
tattcttgac cttgtcacca tactacaaag tgtttctcac taggctcata tggtggttac   2880
aatactttat caccagagcc gaggcgcaca tgcaagtgtg gtccccccc ctcaacgttc      2940 ggggaggccg cgatgccatc atcctcctca cgtgtgcggt tcatccagag ttaattttg      3000 acatcaccaa actcctgctc gccatactcg gcccgctcat ggtgctccag gctggcataa   3060
cgagagtgcc gtacttcgtg cgcgctcaag ggctcattcg tgcatgcatg ttagtgcgaa   3120
aagtcgccgg gggtcattat gtccaaatgg tcttcatgaa gctgggcgcg ctgacaggta   3180
cgtacgttta taaccatctt accccactgc gggactgggc ccacgcgggc ctacgagacc   3240
ttgcggtggc ggtagagccc gtcgtcttct ccgccatgga gaccaaggtc atcacctggg   3300
gagcagacac cgctgcgtgt ggggacatca tcttgggtct acccgtctcc gcccgaaggg   3360
ggaaggagat attttttggga ccggctgata gtctcgaagg gcaagggtgg cgactccttg   3420
cgcccatcac ggcctactcc caacaaacgc ggggcgtact tggttgcatc atcactagcc   3480
tcacaggccg ggacaagaac caggtcgaag gggaggttca agtggtttct accgcaacac   3540
aatctttcct ggcgacctgc atcaacgcg tgtgctggac tgtctaccat ggcgctggct      3600
cgaagaccct agccggtcca aaaggtccaa tcacccaaat gtacaccaat gtagacctgg   3660
acctcgtcgg ctggcaggcg ccccccgggg cgcgctccat gacaccatgc agctgtggca   3720
gctcggacct ttacttggtc acgagacatg ctgatgtcat tccggtgcgc cggcgaggcg   3780
acagcagggg aagtctactc tcccccaggc ccgtctccta cctgaaaggc tcctcgggtg   3840
gtccattgct ttgcccttcg gggcacgtcg tgggcgtctt ccgggctgct gtgtgcaccc   3900
ggggggtcgc gaaggcggtg gacttcatac ccgttgagtc tatggaaact accatgcggt   3960
ctccggtctt cacagacaac tcaaccccc cggctgtacc gcagacattc caagtggcac   4020
atctgcacgc tcctactggc agcggcaaga gcaccaaagt gccggctgcg tatgcagccc   4080
aagggtacaa ggtgctcgtc ctgaacccgt ccgttgccgc caccttaggg tttggggcgt   4140
atatgtccaa ggcacacggt atcgacccta acatcagaac tggggtaagg accattacca   4200
cgggcggctc cattacgtac tccacctatg gcaagttcct tgccgacggt ggctgttctg   4260
ggggcgccta tgacatcata atatgtgatg agtgccactc aactgactcg actaccatct   4320
tgggcatcgg cacagtcctg gaccaagcgg agacggctgg agcgcggctc gtcgtgctcg   4380
ccaccgctac acctccggga tcggttaccg tgccacaccc caatatcgag gaaataggcc   4440
tgtccaacaa tggagagatc cccttctatg gcaaagccat ccccattgag gccatcaagg   4500
gggggaggca tctcattttc tgccattcca agaagaaatg tgacgagctc gccgcaaagc   4560
tgacaggcct cggactgaac gctgtagcat attaccgggg ccttgatgtg tccgtcatac   4620
cgcctatcgg agacgtcgtt gtcgtggcaa cagacgctct aatgacgggt ttcaccggcg   4680
attttgactc agtgatcgac tgcaatacat gtgtcaccca gacagtcgac ttcagcttgg   4740 atcccaccctt caccattgag acgacgaccg tgccccaaga cgcggtgtcg cgctcgcaac   4800
ggcgaggtag aactggcagg ggtaggagtg gcatctacag gtttgtgact ccaggagaac   4860
```

```
ggccctcggg catgttcgat tcttcggtcc tgtgtgagtg ctatgacgcg ggctgtgctt   4920
ggtatgagct cacgcccgct gagacctcgg ttaggttgcg ggcttaccta aatacaccag   4980
ggttgcccgt ctgccaggac catctggagt tctgggagag cgtcttcaca ggcctcaccc   5040
acatagatgc ccacttcctg tcccagacta acaggcagg  agacaacttt ccttacctgg   5100
tggcatatca agctacagtg tgcgccaggg ctcaagctcc acctccatcg tgggaccaaa   5160
tgtggaagtg tctcatacgg ctgaaaccta cactgcacgg ccaacaccc  ctgctgtata   5220
ggctaggagc cgtccaaaat gaggtcatcc tcacacaccc cataactaaa tacatcatgg   5280
catgcatgtc ggctgacctg gaggtcgtca ctagcacctg ggtgctggta ggcggagtcc   5340
ttgcagcttt ggccgcatac tgcctgacga caggcagtgt ggtcattgtg ggcaggatca   5400
tcttgtccgg gaagccagct gtcgttcccg acagggaagt cctctaccag gagttcgatg   5460
agatggaaga gtgtgcctca caacttcctt acatcgagca gggaatgcag ctcgccgagc   5520
aattcaagca aaaggcgctc gggttgttgc aaacggccac caagcaagcg gaggctgctg   5580
ctcccgtggt ggagtccaag tggcgagccc ttgagacctt ctgggcgaag cacatgtgga   5640
atttcatcag cggaatacag tacctagcag gcttatccac tctgcctgga accccgcga   5700
tagcatcatt gatggcattt acagcttcta tcactagccc gctcaccacc caaaacaccc   5760
tcctgtttaa catcttgggg ggatgggtgg ctgcccaact cgctcctccc agcgctgcgt   5820
cagctttcgt gggcgccggc atcgccggag cggctgttgg cagcataggc cttgggaagg   5880
tgctcgtgga catcttggcg ggctatgggg caggggtagc cggcgcactc gtggccttta   5940
aggtcatgag cggcgaggtg ccctccaccg aggacctggt caacttactc cctgccatcc   6000
tctctcctgg tgccctggtc gtcggggtcg tgtgcgcagc aatactgcgt cggcacgtgg   6060
gcccgggaga ggggctgtg  cagtggatga accggctgat agcgttcgct tcgcggggta   6120
accacgtctc ccctacgcac tatgtgcctg agagcgacgc tgcagcacgt gtcactcaga   6180
tcctctctag ccttaccatc actcaactgc tgaagcggct ccaccagtgg attaatgagg   6240
actgctctac gccatgctcc ggctcgtggc taagggatgt ttgggattgg atatgcacgg   6300
tgttgactga cttcaagacc tggctccagt ccaaactcct gccgcggtta ccgggagtcc   6360
cttttcctgtc atgccaacgc gggtacaagg agtctggcg  ggggacggc  atcatgcaaa   6420
ccacctgccc atgcggagca cagatcgccg gacatgtcaa aaacggttcc atgaggatcg   6480
tagggcctag aacctgcagc aacacgtggc acggaacgtt ccccatcaac gcatacacca   6540
cgggaccttg cacaccctcc ccggcgccca actattccag ggcgctatgg cggtggctg   6600
ctgaggagta cgtggaggtt acgcgtgtgg gggatttcca ctacgtgacg ggcatgacca   6660
ctgacaacgt aaagtgccca tgccaggttc cggcccccga attcttcacg gaggtggatg   6720
gagtgcggtt gcacaggtac gctccggcgt gcaaacctct tctacgggag gacgtcacgt   6780
tccaggtcgg gctcaaccaa tacttggtcg ggtcgcagct cccatgcgag cccgaaccgg   6840
acgtaacagt gcttacttcc atgctcaccg atccctccca cattacagca gagacggcta   6900
agcgtaggct ggctagaggg tctccccct  ctttagccag ctcatcagct agccagttgt   6960
ctgcgccttc tttgaaggcg acatgcacta cccaccatga ctccccggac gctgacctca   7020
tcgaggccaa cctcttgtgg cggcaggaga tgggcggaaa catcactcgc gtggagtcag   7080
agaataaggt agtaattctg gactcttttcg aaccgcttca cgcggagggg gatgagaggg   7140
agatatccgt cgcggcggag atcctgcgaa aatccaggaa gttccctca gcgttgccca   7200
tatgggcacg cccggactac aatcctccac tgctagagtc ctggaaggac ccggactacg   7260
```

-continued

```
tccctccggt ggtacacgga tgcccattgc cacctaccaa ggctcctcca ataccacctc    7320
cacggagaaa gaggacggtt gtcctgacag aatccaatgt gtcttctgcc ttggcggagc    7380
tcgccactaa gaccttcggt agctccggat cgtcggccgt tgatagcggc acggcgaccg    7440
cccttcctga cctggcctcc gacgacggtg acaaaggatc cgacgttgag tcgtactcct    7500
ccatgccccc ccttgaaggg gagccggggg accccgatct cagcgacggg tcttggtcta    7560
ccgtgagtga ggaggctagt gaggatgtcg tctgctgctc aatgtcctat acgtggacag    7620
gcgccctgat cacgccatgc gctgcggagg aaagtaagct gcccatcaac ccgttgagca    7680
actctttgct gcgtcaccac aacatggtct acgccacaac atcccgcagc gcaagcctcc    7740
ggcagaagaa ggtcaccttt gacagattgc aagtcctgga tgatcattac cgggacgtac    7800
tcaaggagat gaaggcgaag gcgtccacag ttaaggctaa gcttctatct atagaggagg    7860
cctgcaagct gacgccccca cattcggcca atccaaatt tggctatggg gcaaaggacg    7920
tccggaacct atccagcagg gccgttaacc acatccgctc cgtgtgggag gacttgctgg    7980
aagacactga acaccaatt gacaccacca tcatggcaaa aagtgaggtt ttctgcgtcc    8040
aaccagagaa gggaggccgc aagccagctc gccttatcgt attcccagac ctgggagttc    8100
gtgtatgcga agatggcc ctttacgacg tggtctccac ccttcctcag gccgtgatgg    8160
gctcctcata cggatttcaa tactccccca agcagcgggt cgagttcctg gtgaatacct    8220
ggaaatcaaa gaaatgccct atgggcttct catatgacac ccgctgtttt gactcaacgg    8280
tcactgagag tgacattcgt gttgaggagt caatttacca atgttgtgac ttggcccccg    8340
aggccagaca ggccataagg tcgctcacag agcggcttta catcgggggt cccctgacta    8400
actcaaaagg gcagaactgc ggttatcgcc ggtgccgcgc aagtggcgtg ctgacgacta    8460
gctgcggtaa taccctcaca tgttacttga aggccactgc agcctgtcga gctgcaaagc    8520
tccaggactg cacgatgctc gtgaacggag acgaccttgt cgttatctgt gaaagcgcgg    8580
gaacccagga ggatgcggcg gccctacgag ccttcacgga ggctatgact aggtattccg    8640 cccccccgg ggatccgccc caaccagaat acgacctgga gctgataaca tcatgttcct    8700
ccaatgtgtc agtcgcgcac gatgcatctg gcaaaagggt atactacctc acccgtgacc    8760
ccaccacccc ccttgcacgg gctgcgtggg agacagctag acacactcca atcaactctt    8820
ggctaggcaa tatcatcatg tatgcgccca ccctatgggc aaggatgatt ctgatgactc    8880
actttttctc catccttcta gctcaagagc aacttgaaaa agccctggat tgtcagatct    8940
acggggcttg ctactccatt gagccacttg acctacctca gatcattgaa cgactccatg    9000
gtcttagcgc atttacactc cacagttact ctccaggtga gatcaatagg gtggcttcat    9060
gcctcaggaa acttgggggta ccaccctttgc gaacctggag acatcgggcc agaagtgtcc    9120
gcgctaagct actgtcccag gggggagggg ccgccacttg tggcagatac ctctttaact    9180
gggcagtaag gaccaagctt aaactcactc caatcccggc cgcgtcccag ctggacttgt    9240
ctggctggtt cgtcgctggt tacagcgggg gagacatata tcacagcctg tctcgtgccc    9300
gaccccgctg gtttccgttg tgcctactcc tactttctgt aggggtaggc atttacctgc    9360
tccccaaccg atgaacgggg agctaaccac tccaggcctt aagccattc ctgtttttt    9420 tttttttttt tttttttttt tctttttttt tttctttcct ttccttcttt ttttcctttc    9480 ttttccctt ctttaatggt ggctccatct tagccctagt cacggctagc tgtgaaaggt    9540
ccgtgagccg catgactgca gagagtgctg atactggcct ctctgcagat catgt    9595
```

-continued

<210> SEQ ID NO 9
<211> LENGTH: 3010
<212> TYPE: PRT
<213> ORGANISM: Hepatitis C virus strain HC-J4

<400> SEQUENCE: 9

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Ala Ser Glu Arg Ser Gln Pro Arg Gly Arg Arg Gln Pro
    50                  55                  60

Ile Pro Lys Ala Arg Arg Pro Glu Gly Arg Ala Trp Ala Gln Pro Gly
65                  70                  75                  80

Tyr Pro Trp Pro Leu Tyr Gly Asn Glu Gly Leu Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala Tyr
            180                 185                 190

Glu Val Arg Asn Val Ser Gly Ile Tyr His Val Thr Asn Asp Cys Ser
        195                 200                 205

Asn Ser Ser Ile Val Tyr Glu Ala Ala Asp Val Ile Met His Thr Pro
    210                 215                 220

Gly Cys Val Pro Cys Val Gln Glu Gly Asn Ser Ser Arg Cys Trp Val
225                 230                 235                 240

Ala Leu Thr Pro Thr Leu Ala Ala Arg Asn Ala Ser Val Pro Thr Thr
                245                 250                 255

Thr Ile Arg Arg His Val Asp Leu Leu Val Gly Thr Ala Ala Phe Cys
            260                 265                 270

Ser Ala Met Tyr Val Gly Asp Leu Cys Gly Ser Ile Phe Leu Val Ser
        275                 280                 285

Gln Leu Phe Thr Phe Ser Pro Arg Arg His Glu Thr Val Gln Asp Cys
    290                 295                 300

Asn Cys Ser Ile Tyr Pro Gly His Val Ser Gly His Arg Met Ala Trp
305                 310                 315                 320

Asp Met Met Met Asn Trp Ser Pro Thr Thr Ala Leu Val Val Ser Gln
                325                 330                 335

Leu Leu Arg Ile Pro Gln Ala Val Val Asp Met Val Ala Gly Ala His
            340                 345                 350

Trp Gly Val Leu Ala Gly Leu Ala Tyr Tyr Ser Met Val Gly Asn Trp
        355                 360                 365

Ala Lys Val Leu Ile Val Ala Leu Leu Phe Ala Gly Val Asp Gly Glu
    370                 375                 380

```
Thr His Thr Thr Gly Arg Val Ala Gly His Thr Thr Ser Gly Phe Thr
385                 390                 395                 400

Ser Leu Phe Ser Ser Gly Ala Ser Gln Lys Ile Gln Leu Val Asn Thr
            405                 410                 415

Asn Gly Ser Trp His Ile Asn Arg Thr Ala Leu Asn Cys Asn Asp Ser
        420                 425                 430

Leu Gln Thr Gly Phe Phe Ala Ala Leu Phe Tyr Ala His Lys Phe Asn
            435                 440                 445

Ser Ser Gly Cys Pro Glu Arg Met Ala Ser Cys Arg Pro Ile Asp Trp
        450                 455                 460

Phe Ala Gln Gly Trp Gly Pro Ile Thr Tyr Thr Lys Pro Asn Ser Ser
465                 470                 475                 480

Asp Gln Arg Pro Tyr Cys Trp His Tyr Ala Pro Arg Pro Cys Gly Val
                485                 490                 495

Val Pro Ala Ser Gln Val Cys Gly Pro Val Tyr Cys Phe Thr Pro Ser
            500                 505                 510

Pro Val Val Gly Thr Thr Asp Arg Ser Gly Val Pro Thr Tyr Ser
            515                 520                 525

Trp Gly Glu Asn Glu Thr Asp Val Met Leu Leu Asn Asn Thr Arg Pro
530                 535                 540

Pro Gln Gly Asn Trp Phe Gly Cys Thr Trp Met Asn Ser Thr Gly Phe
545                 550                 555                 560

Thr Lys Thr Cys Gly Gly Pro Pro Cys Asn Ile Gly Gly Val Gly Asn
                565                 570                 575

Arg Thr Leu Ile Cys Pro Thr Asp Cys Phe Arg Lys His Pro Glu Ala
            580                 585                 590

Thr Tyr Thr Lys Cys Gly Ser Gly Pro Trp Leu Thr Pro Arg Cys Leu
            595                 600                 605

Val Asp Tyr Pro Tyr Arg Leu Trp His Tyr Pro Cys Thr Leu Asn Phe
610                 615                 620

Ser Ile Phe Lys Val Arg Met Tyr Val Gly Gly Val Glu His Arg Leu
625                 630                 635                 640

Asn Ala Ala Cys Asn Trp Thr Arg Gly Glu Arg Cys Asn Leu Glu Asp
                645                 650                 655

Arg Asp Arg Ser Glu Leu Ser Pro Leu Leu Leu Ser Thr Thr Glu Trp
            660                 665                 670

Gln Ile Leu Pro Cys Ala Phe Thr Thr Leu Pro Ala Leu Ser Thr Gly
            675                 680                 685

Leu Ile His Leu His Gln Asn Ile Val Asp Val Gln Tyr Leu Tyr Gly
690                 695                 700

Val Gly Ser Ala Phe Val Ser Phe Ala Ile Lys Trp Glu Tyr Ile Leu
705                 710                 715                 720

Leu Leu Phe Leu Leu Leu Ala Asp Ala Arg Val Cys Ala Cys Leu Trp
            725                 730                 735

Met Met Leu Leu Ile Ala Gln Ala Glu Ala Ala Leu Glu Asn Leu Val
            740                 745                 750

Val Leu Asn Ala Ala Ser Val Ala Gly Ala His Gly Ile Leu Ser Phe
            755                 760                 765

Leu Val Phe Phe Cys Ala Ala Trp Tyr Ile Lys Gly Arg Leu Ala Pro
            770                 775                 780

Gly Ala Ala Tyr Ala Phe Tyr Gly Val Trp Pro Leu Leu Leu Leu Leu
785                 790                 795                 800
```

```
Leu Ala Leu Pro Pro Arg Ala Tyr Ala Leu Asp Arg Glu Met Ala Ala
                805                 810                 815

Ser Cys Gly Gly Ala Val Leu Val Gly Leu Val Phe Leu Thr Leu Ser
                820                 825                 830

Pro Tyr Tyr Lys Val Phe Leu Thr Arg Leu Ile Trp Trp Leu Gln Tyr
                835                 840                 845

Phe Ile Thr Arg Ala Glu Ala His Met Gln Val Trp Val Pro Pro Leu
                850                 855                 860

Asn Val Arg Gly Gly Arg Asp Ala Ile Ile Leu Leu Thr Cys Ala Val
865                 870                 875                 880

His Pro Glu Leu Ile Phe Asp Ile Thr Lys Leu Leu Leu Ala Ile Leu
                885                 890                 895

Gly Pro Leu Met Val Leu Gln Ala Gly Ile Thr Arg Val Pro Tyr Phe
                900                 905                 910

Val Arg Ala Gln Gly Leu Ile Arg Ala Cys Met Leu Val Arg Lys Val
                915                 920                 925

Ala Gly Gly His Tyr Val Gln Met Val Phe Met Lys Leu Gly Ala Leu
                930                 935                 940

Thr Gly Thr Tyr Val Tyr Asn His Leu Thr Pro Leu Arg Asp Trp Ala
945                 950                 955                 960

His Ala Gly Leu Arg Asp Leu Ala Val Ala Val Glu Pro Val Val Phe
                965                 970                 975

Ser Ala Met Glu Thr Lys Val Ile Thr Trp Gly Ala Asp Thr Ala Ala
                980                 985                 990

Cys Gly Asp Ile Ile Leu Gly Leu Pro Val Ser Ala Arg Arg Gly Lys
                995                 1000                1005

Glu Ile Phe Leu Gly Pro Ala Asp Ser Leu Glu Gly Gln Gly Trp Arg
                1010                1015                1020

Leu Leu Ala Pro Ile Thr Ala Tyr Ser Gln Gln Thr Arg Gly Val Leu
1025                1030                1035                1040

Gly Cys Ile Ile Thr Ser Leu Thr Gly Arg Asp Lys Asn Gln Val Glu
                1045                1050                1055

Gly Glu Val Gln Val Val Ser Thr Ala Thr Gln Ser Phe Leu Ala Thr
                1060                1065                1070

Cys Ile Asn Gly Val Cys Trp Thr Val Tyr His Gly Ala Gly Ser Lys
                1075                1080                1085

Thr Leu Ala Gly Pro Lys Gly Pro Ile Thr Gln Met Tyr Thr Asn Val
                1090                1095                1100

Asp Leu Asp Leu Val Gly Trp Gln Ala Pro Pro Gly Ala Arg Ser Met
1105                1110                1115                1120

Thr Pro Cys Ser Cys Gly Ser Ser Asp Leu Tyr Leu Val Thr Arg His
                1125                1130                1135

Ala Asp Val Ile Pro Val Arg Arg Arg Gly Asp Ser Arg Gly Ser Leu
                1140                1145                1150

Leu Ser Pro Arg Pro Val Ser Tyr Leu Lys Gly Ser Ser Gly Gly Pro
                1155                1160                1165

Leu Leu Cys Pro Ser Gly His Val Val Gly Val Phe Arg Ala Ala Val
                1170                1175                1180

Cys Thr Arg Gly Val Ala Lys Ala Val Asp Phe Ile Pro Val Glu Ser
1185                1190                1195                1200

Met Glu Thr Thr Met Arg Ser Pro Val Phe Thr Asp Asn Ser Thr Pro
                1205                1210                1215

Pro Ala Val Pro Gln Thr Phe Gln Val Ala His Leu His Ala Pro Thr
```

-continued

```
                1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Thr Leu Gly Phe
        1250                1255                1260
Gly Ala Tyr Met Ser Lys Ala His Gly Ile Asp Pro Asn Ile Arg Thr
1265                1270                1275                1280
Gly Val Arg Thr Ile Thr Thr Gly Gly Ser Ile Thr Tyr Ser Thr Tyr
                1285                1290                1295
Gly Lys Phe Leu Ala Asp Gly Cys Ser Gly Gly Ala Tyr Asp Ile
        1300                1305                1310
Ile Ile Cys Asp Glu Cys His Ser Thr Asp Ser Thr Thr Ile Leu Gly
        1315                1320                1325
Ile Gly Thr Val Leu Asp Gln Ala Glu Thr Ala Gly Ala Arg Leu Val
        1330                1335                1340
Val Leu Ala Thr Ala Thr Pro Pro Gly Ser Val Thr Val Pro His Pro
1345                1350                1355                1360
Asn Ile Glu Glu Ile Gly Leu Ser Asn Asn Gly Glu Ile Pro Phe Tyr
                1365                1370                1375
Gly Lys Ala Ile Pro Ile Glu Ala Ile Lys Gly Gly Arg His Leu Ile
        1380                1385                1390
Phe Cys His Ser Lys Lys Lys Cys Asp Glu Leu Ala Ala Lys Leu Thr
        1395                1400                1405
Gly Leu Gly Leu Asn Ala Val Ala Tyr Tyr Arg Gly Leu Asp Val Ser
        1410                1415                1420
Val Ile Pro Pro Ile Gly Asp Val Val Val Ala Thr Asp Ala Leu
1425                1430                1435                1440
Met Thr Gly Phe Thr Gly Asp Phe Asp Ser Val Ile Asp Cys Asn Thr
                1445                1450                1455
Cys Val Thr Gln Thr Val Asp Phe Ser Leu Asp Pro Thr Phe Thr Ile
                1460                1465                1470
Glu Thr Thr Thr Val Pro Gln Asp Ala Val Ser Arg Ser Gln Arg Arg
        1475                1480                1485
Gly Arg Thr Gly Arg Gly Arg Ser Gly Ile Tyr Arg Phe Val Thr Pro
        1490                1495                1500
Gly Glu Arg Pro Ser Gly Met Phe Asp Ser Ser Val Leu Cys Glu Cys
1505                1510                1515                1520
Tyr Asp Ala Gly Cys Ala Trp Tyr Glu Leu Thr Pro Ala Glu Thr Ser
                1525                1530                1535
Val Arg Leu Arg Ala Tyr Leu Asn Thr Pro Gly Leu Pro Val Cys Gln
                1540                1545                1550
Asp His Leu Glu Phe Trp Glu Ser Val Phe Thr Gly Leu Thr His Ile
        1555                1560                1565
Asp Ala His Phe Leu Ser Gln Thr Lys Gln Ala Gly Asp Asn Phe Pro
        1570                1575                1580
Tyr Leu Val Ala Tyr Gln Ala Thr Val Cys Ala Arg Ala Gln Ala Pro
1585                1590                1595                1600
Pro Pro Ser Trp Asp Gln Met Trp Lys Cys Leu Ile Arg Leu Lys Pro
                1605                1610                1615
Thr Leu His Gly Pro Thr Pro Leu Leu Tyr Arg Leu Gly Ala Val Gln
        1620                1625                1630
Asn Glu Val Ile Leu Thr His Pro Ile Thr Lys Tyr Ile Met Ala Cys
        1635                1640                1645
```

-continued

```
Met Ser Ala Asp Leu Glu Val Val Thr Ser Thr Trp Val Leu Val Gly
1650                1655                1660

Gly Val Leu Ala Ala Leu Ala Ala Tyr Cys Leu Thr Thr Gly Ser Val
1665                1670                1675                1680

Val Ile Val Gly Arg Ile Ile Leu Ser Gly Lys Pro Ala Val Val Pro
                    1685                1690                1695

Asp Arg Glu Val Leu Tyr Gln Glu Phe Asp Glu Met Glu Glu Cys Ala
                1700                1705                1710

Ser Gln Leu Pro Tyr Ile Glu Gln Gly Met Gln Leu Ala Glu Gln Phe
            1715                1720                1725

Lys Gln Lys Ala Leu Gly Leu Leu Gln Thr Ala Thr Lys Gln Ala Glu
        1730                1735                1740

Ala Ala Ala Pro Val Val Glu Ser Lys Trp Arg Ala Leu Glu Thr Phe
1745                1750                1755                1760

Trp Ala Lys His Met Trp Asn Phe Ile Ser Gly Ile Gln Tyr Leu Ala
                    1765                1770                1775

Gly Leu Ser Thr Leu Pro Gly Asn Pro Ala Ile Ala Ser Leu Met Ala
                1780                1785                1790

Phe Thr Ala Ser Ile Thr Ser Pro Leu Thr Thr Gln Asn Thr Leu Leu
            1795                1800                1805

Phe Asn Ile Leu Gly Gly Trp Val Ala Ala Gln Leu Ala Pro Pro Ser
        1810                1815                1820

Ala Ala Ser Ala Phe Val Gly Ala Gly Ile Ala Gly Ala Ala Val Gly
1825                1830                1835                1840

Ser Ile Gly Leu Gly Lys Val Leu Val Asp Ile Leu Ala Gly Tyr Gly
                    1845                1850                1855

Ala Gly Val Ala Gly Ala Leu Val Ala Phe Lys Val Met Ser Gly Glu
                1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
        1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
                    1925                1930                1935

Glu Ser Asp Ala Ala Ala Arg Val Thr Gln Ile Leu Ser Ser Leu Thr
                1940                1945                1950

Ile Thr Gln Leu Leu Lys Arg Leu His Gln Trp Ile Asn Glu Asp Cys
            1955                1960                1965

Ser Thr Pro Cys Ser Gly Ser Trp Leu Arg Asp Val Trp Asp Trp Ile
        1970                1975                1980

Cys Thr Val Leu Thr Asp Phe Lys Thr Trp Leu Gln Ser Lys Leu Leu
1985                1990                1995                2000

Pro Arg Leu Pro Gly Val Pro Phe Leu Ser Cys Gln Arg Gly Tyr Lys
                    2005                2010                2015

Gly Val Trp Arg Gly Asp Gly Ile Met Gln Thr Thr Cys Pro Cys Gly
                2020                2025                2030

Ala Gln Ile Ala Gly His Val Lys Asn Gly Ser Met Arg Ile Val Gly
            2035                2040                2045

Pro Arg Thr Cys Ser Asn Thr Trp His Gly Thr Phe Pro Ile Asn Ala
        2050                2055                2060
```

-continued

```
Tyr Thr Thr Gly Pro Cys Thr Pro Ser Pro Ala Pro Asn Tyr Ser Arg
2065                2070                2075                2080

Ala Leu Trp Arg Val Ala Ala Glu Glu Tyr Val Glu Val Thr Arg Val
            2085                2090                2095

Gly Asp Phe His Tyr Val Thr Gly Met Thr Thr Asp Asn Val Lys Cys
        2100                2105                2110

Pro Cys Gln Val Pro Ala Pro Glu Phe Phe Thr Glu Val Asp Gly Val
    2115                2120                2125

Arg Leu His Arg Tyr Ala Pro Ala Cys Lys Pro Leu Leu Arg Glu Asp
2130                2135                2140

Val Thr Phe Gln Val Gly Leu Asn Gln Tyr Leu Val Gly Ser Gln Leu
2145                2150                2155                2160

Pro Cys Glu Pro Glu Pro Asp Val Thr Val Leu Thr Ser Met Leu Thr
            2165                2170                2175

Asp Pro Ser His Ile Thr Ala Glu Thr Ala Lys Arg Arg Leu Ala Arg
        2180                2185                2190

Gly Ser Pro Pro Ser Leu Ala Ser Ser Ser Ala Ser Gln Leu Ser Ala
    2195                2200                2205

Pro Ser Leu Lys Ala Thr Cys Thr Thr His His Asp Ser Pro Asp Ala
2210                2215                2220

Asp Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Glu Pro Leu His Ala Glu Gly Asp Glu Arg Glu Ile Ser Val Ala Ala
        2260                2265                2270

Glu Ile Leu Arg Lys Ser Arg Lys Phe Pro Ser Ala Leu Pro Ile Trp
    2275                2280                2285

Ala Arg Pro Asp Tyr Asn Pro Pro Leu Leu Glu Ser Trp Lys Asp Pro
2290                2295                2300

Asp Tyr Val Pro Pro Val Val His Gly Cys Pro Leu Pro Pro Thr Lys
2305                2310                2315                2320

Ala Pro Pro Ile Pro Pro Arg Arg Lys Arg Thr Val Val Leu Thr
            2325                2330                2335

Glu Ser Asn Val Ser Ser Ala Leu Ala Glu Leu Ala Thr Lys Thr Phe
        2340                2345                2350

Gly Ser Ser Gly Ser Ser Ala Val Asp Ser Gly Thr Ala Thr Ala Leu
    2355                2360                2365

Pro Asp Leu Ala Ser Asp Asp Gly Asp Lys Gly Ser Asp Val Glu Ser
2370                2375                2380

Tyr Ser Ser Met Pro Pro Leu Glu Gly Glu Pro Gly Asp Pro Asp Leu
2385                2390                2395                2400

Ser Asp Gly Ser Trp Ser Thr Val Ser Glu Glu Ala Ser Glu Asp Val
            2405                2410                2415

Val Cys Cys Ser Met Ser Tyr Thr Trp Thr Gly Ala Leu Ile Thr Pro
        2420                2425                2430

Cys Ala Ala Glu Glu Ser Lys Leu Pro Ile Asn Pro Leu Ser Asn Ser
    2435                2440                2445

Leu Leu Arg His His Asn Met Val Tyr Ala Thr Thr Ser Arg Ser Ala
2450                2455                2460

Ser Leu Arg Gln Lys Lys Val Thr Phe Asp Arg Leu Gln Val Leu Asp
2465                2470                2475                2480

Asp His Tyr Arg Asp Val Leu Lys Glu Met Lys Ala Lys Ala Ser Thr
```

-continued

```
                2485                2490                2495
Val Lys Ala Lys Leu Leu Ser Ile Glu Glu Ala Cys Lys Leu Thr Pro
                2500                2505                2510
Pro His Ser Ala Lys Ser Lys Phe Gly Tyr Gly Ala Lys Asp Val Arg
                2515                2520                2525
Asn Leu Ser Ser Arg Ala Val Asn His Ile Arg Ser Val Trp Glu Asp
                2530                2535                2540
Leu Leu Glu Asp Thr Glu Thr Pro Ile Asp Thr Thr Ile Met Ala Lys
2545                2550                2555                2560
Ser Glu Val Phe Cys Val Gln Pro Glu Lys Gly Gly Arg Lys Pro Ala
                2565                2570                2575
Arg Leu Ile Val Phe Pro Asp Leu Gly Val Arg Val Cys Glu Lys Met
                2580                2585                2590
Ala Leu Tyr Asp Val Val Ser Thr Leu Pro Gln Ala Val Met Gly Ser
                2595                2600                2605
Ser Tyr Gly Phe Gln Tyr Ser Pro Lys Gln Arg Val Glu Phe Leu Val
                2610                2615                2620
Asn Thr Trp Lys Ser Lys Lys Cys Pro Met Gly Phe Ser Tyr Asp Thr
2625                2630                2635                2640
Arg Cys Phe Asp Ser Thr Val Thr Glu Ser Asp Ile Arg Val Glu Glu
                2645                2650                2655
Ser Ile Tyr Gln Cys Cys Asp Leu Ala Pro Glu Ala Arg Gln Ala Ile
                2660                2665                2670
Arg Ser Leu Thr Glu Arg Leu Tyr Ile Gly Gly Pro Leu Thr Asn Ser
                2675                2680                2685
Lys Gly Gln Asn Cys Gly Tyr Arg Arg Cys Arg Ala Ser Gly Val Leu
                2690                2695                2700
Thr Thr Ser Cys Gly Asn Thr Leu Thr Cys Tyr Leu Lys Ala Thr Ala
2705                2710                2715                2720
Ala Cys Arg Ala Ala Lys Leu Gln Asp Cys Thr Met Leu Val Asn Gly
                2725                2730                2735
Asp Asp Leu Val Val Ile Cys Glu Ser Ala Gly Thr Gln Glu Asp Ala
                2740                2745                2750
Ala Ala Leu Arg Ala Phe Thr Glu Ala Met Thr Arg Tyr Ser Ala Pro
                2755                2760                2765
Pro Gly Asp Pro Pro Gln Pro Glu Tyr Asp Leu Glu Leu Ile Thr Ser
                2770                2775                2780
Cys Ser Ser Asn Val Ser Val Ala His Asp Ala Ser Gly Lys Arg Val
2785                2790                2795                2800
Tyr Tyr Leu Thr Arg Asp Pro Thr Thr Pro Leu Ala Arg Ala Ala Trp
                2805                2810                2815
Glu Thr Ala Arg His Thr Pro Ile Asn Ser Trp Leu Gly Asn Ile Ile
                2820                2825                2830
Met Tyr Ala Pro Thr Leu Trp Ala Arg Met Ile Leu Met Thr His Phe
                2835                2840                2845
Phe Ser Ile Leu Leu Ala Gln Glu Gln Leu Glu Lys Ala Leu Asp Cys
                2850                2855                2860
Gln Ile Tyr Gly Ala Cys Tyr Ser Ile Glu Pro Leu Asp Leu Pro Gln
2865                2870                2875                2880
Ile Ile Glu Arg Leu His Gly Leu Ser Ala Phe Thr Leu His Ser Tyr
                2885                2890                2895
Ser Pro Gly Glu Ile Asn Arg Val Ala Ser Cys Leu Arg Lys Leu Gly
                2900                2905                2910
```

```
-continued

Val Pro Pro Leu Arg Thr Trp Arg His Arg Ala Arg Ser Val Arg Ala
        2915                2920                2925

Lys Leu Leu Ser Gln Gly Gly Arg Ala Ala Thr Cys Gly Arg Tyr Leu
        2930                2935                2940

Phe Asn Trp Ala Val Arg Thr Lys Leu Lys Leu Thr Pro Ile Pro Ala
2945                2950                2955                2960

Ala Ser Gln Leu Asp Leu Ser Gly Trp Phe Val Ala Gly Tyr Ser Gly
                2965                2970                2975

Gly Asp Ile Tyr His Ser Leu Ser Arg Ala Arg Pro Arg Trp Phe Pro
            2980                2985                2990

Leu Cys Leu Leu Leu Leu Ser Val Gly Val Gly Ile Tyr Leu Leu Pro
        2995                3000                3005

Asn Arg
    3010

<210> SEQ ID NO 10
<211> LENGTH: 24
<212> TYPE: DNA
<213> ORGANISM: Artificial Sequence
<220> FEATURE:
<223> OTHER INFORMATION: synthetic primer

<400> SEQUENCE: 10
cctagcaggg cgtgggggat ttcc                                      24

<210> SEQ ID NO 11
<211> LENGTH: 24
<212> TYPE: DNA
<213> ORGANISM: Artificial Sequence
<220> FEATURE:
<223> OTHER INFORMATION: synthetic primer

<400> SEQUENCE: 11
aggtctgcgt ccttggtagt gacc                                      24

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
ggatttcccc tgcccgtctg                                           20

<210> SEQ ID NO 13
<211> LENGTH: 20
<212> TYPE: DNA
<213> ORGANISM: Artificial Sequence
<220> FEATURE:
<223> OTHER INFORMATION: synthetic primer

<400> SEQUENCE: 13
ccccggtctt ccctacagtg                                           20
```